(12) United States Patent
Wei et al.

(10) Patent No.: US 7,384,955 B2
(45) Date of Patent: Jun. 10, 2008

(54) AZAINDOLE DERIVATIVES, PREPARATIONS THEREOF, USES THEREOF AND COMPOSITIONS CONTAINING THEM

(75) Inventors: Zhongyong Wei, Saint-Laurent (CA); Regis Dolaine, Remondel, Noyal-Chatillon-sur-Seiche (FR); Christopher Walpole, Saint-Laurent (CA); Hua Yang, Saint-Laurent (CA)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/550,663

(22) PCT Filed: Mar. 26, 2004

(86) PCT No.: PCT/SE2004/000472

§ 371 (c)(1),
(2), (4) Date: Sep. 26, 2005

(87) PCT Pub. No.: WO2004/087704

PCT Pub. Date: Oct. 14, 2004

(65) Prior Publication Data

US 2007/0027179 A1 Feb. 1, 2007

(30) Foreign Application Priority Data

Mar. 31, 2003 (SE) .................... 0300908

(51) Int. Cl.
C07D 471/02 (2006.01)
C07D 491/02 (2006.01)
C07D 498/02 (2006.01)
A01N 43/42 (2006.01)
A61K 31/44 (2006.01)

(52) U.S. Cl. ...................... 514/300; 546/113
(58) Field of Classification Search ................ 546/113; 514/300
See application file for complete search history.

(56) References Cited

U.S. PATENT DOCUMENTS

| 6,025,366 | A | 2/2000 | Walsh et al. |
| 6,384,235 | B2 | 5/2002 | Henkelmann et al. |
| 6,673,797 | B1 | 1/2004 | Matsuoka et al. |
| 6,875,770 | B2 | 4/2005 | Matsuoka et al. |
| 2002/0091124 | A1 | 7/2002 | Beckers et al. |
| 2003/0158216 | A1 | 8/2003 | Beckers et al. |

| 2005/0137202 | A1 | 6/2005 | Matsuoka et al. |

FOREIGN PATENT DOCUMENTS

| WO | 9533748 A1 | 12/1995 |
| WO | 9822457 A1 | 5/1998 |
| WO | 9951232 A1 | 10/1999 |
| WO | 9951234 A1 | 10/1999 |
| WO | 0075117 A1 | 12/2000 |
| WO | 0075145 A1 | 12/2000 |
| WO | 0102394 A1 | 1/2001 |
| WO | 0147922 A2 | 7/2001 |
| WO | 0158869 A2 | 8/2001 |
| WO | WO 01/82909 | * 8/2001 |
| WO | 0170743 A1 | 9/2001 |

OTHER PUBLICATIONS

Schulte et al., Regulatory Toxicology and Pharmacology, "Two immunotoxicity ring studies according to OECD TG 407—comparison of data on cyclosporin A and hexachlorobenzene", 2002, vol. 36, pp. 12-21.*
Fischer et al., Life Sciences, "Polychlorinated biphenyls release insulin from RINm5F cells", 1996, vol. 59, pp. 2041-2049.*
Desarbre et al., Tetrahedron, "Synthesis of 2-substituted-1H-pyrrolo[2,3-b]pyridines: preparation of 7-Azaolivacine analogue and 7-Azaindolopyridopyrimidine derivatives", 1997, vol. 53, pp. 3637-3648.*
Mahboobi et al., Journal of Medicinal Chemistry, "Synthetic 2-Aroylindole derivatives as a new class of potent tubulin-inhibitory, antimitotic agents", 2001, vol. 44, pp. 4535-4553.*

* cited by examiner

Primary Examiner—Margaret D. Seaman
Assistant Examiner—Niloofar Rahmani
(74) Attorney, Agent, or Firm—Jianzhong Shen

(57) ABSTRACT

Compounds of formula I or pharmaceutically acceptable salts thereof Formula (I) wherein Ar, $R^1$, $R^2$, $R^3$, $R^a$, $R^b$ and X are as defined in the specification as well as salts and pharmaceutical compositions including the compounds are prepared. They are useful in therapy, in particular in the management of pain (I)

12 Claims, No Drawings

AZAINDOLE DERIVATIVES, PREPARATIONS THEREOF, USES THEREOF AND COMPOSITIONS CONTAINING THEM

CROSS-REFERENCE TO RELATED APPLICATIONS

This application is a US National Stage under 35 U.S.C § 371 of International Application No. PCT/SE2004/000472, filed on 26 Mar. 2004, which claims priority under 35 U.S.C. § 119(a)-(d) to Swedish Application No. 0300908-1 filed on 31 Mar. 2003.

BACKGROUND OF THE INVENTION

1. Field of the Invention

The invention is related to compounds which are $CB_1/CB_2$ receptor ligands, pharmaceutical compositions contain these compounds, manufacturing processes thereof and uses thereof, and more particularly to compounds that are $CB_1/CB_2$ receptor agonists.

2. Discussion of Relevant Technology

Pain management has been an important field of study for many years. It has been well known that cannabinoid receptor (e.g., $CB_1$ receptors, $CB_2$ receptors) ligands, especially agonists produce relief of pain in a variety of animal models by interacting with $CB_1$ and/or $CB_2$ receptors. Generally, $CB_1$ receptors are located predominantly in the central nervous system, whereas $CB_2$ receptors are located primarily in the periphery and are primarily restricted to the cells and tissues derived from the immune system.

While the conventional $CB_1$ receptor agonists and $CB_1/CB_2$ receptor agonists, such as tetrahydrocannabinol (THC) and *Cannabis*-related drugs, are highly effective in anti-nociception models in animals, they tend to exert many undesired CNS (central nerve system) side-effects, e.g., psychoactive side effects and the abuse potential of *Cannabis*-related drugs.

Therefore, there is a need for new $CB_1/CB_2$ receptor ligands such as agonists useful in managing pain or treating other related symptoms or diseases with reduced or minimal undesirable CNS side-effects.

DISCLOSURE OF THE INVENTION

The present invention provides $CB_1/CB_2$ receptor ligands which are useful in treating pain and other related symptoms or diseases.

Definitions

Unless specified otherwise within this specification, the nomenclature used in this specification generally follows the examples and rules stated in *Nomenclature of Organic Chemistry, Sections A, B, C, D, E, F, and H*, Pergamon Press, Oxford, 1979, which is incorporated by references herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

"$CB_1/CB_2$ receptors" means $CB_1$ and/or $CB_2$ receptors.

The term "$C_{m-n}$" or "$C_{m-n}$ group" used alone or as a prefix, refers to any group having m to n carbon atoms, and having 0 to n multivalent heteroatoms selected from O, S, N and P, wherein m and n are 0 or positive integers, and n>m. For example, "$C_{1-6}$" would refer to a chemical group having 1 to 6 carbon atoms, and having 0 to 6 multivalent heteroatoms selected from O, S, N and P.

The term "hydrocarbon" used alone or as a suffix or prefix, refers to any structure comprising only carbon and hydrogen atoms up to 14 carbon atoms.

The term "hydrocarbon radical" or "hydrocarbyl" used alone or as a suffix or prefix, refers to any structure as a result of removing one or more hydrogens from a hydrocarbon.

The term "alkyl" used alone or as a suffix or prefix, refers to monovalent straight or branched chain hydrocarbon radicals comprising 1 to about 12 carbon atoms. Unless otherwise specified, "alkyl" general includes both saturated alkyl and unsaturated alkyl.

The term "alkylene" used alone or as suffix or prefix, refers to divalent straight or branched chain hydrocarbon radicals comprising 1 to about 12 carbon atoms, which serves to links two structures together.

The term "alkenyl" used alone or as suffix or prefix, refers to a monovalent straight or branched chain hydrocarbon radical having at least one carbon-carbon double bond and comprising at least 2 up to about 12 carbon atoms.

The term "alkynyl" used alone or as suffix or prefix, refers to a monovalent straight or branched chain hydrocarbon radical having at least one carbon-carbon triple bond and comprising at least 2 up to about 12 carbon atoms.

The term "cycloalkyl," used alone or as suffix or prefix, refers to a monovalent ring-containing hydrocarbon radical comprising at least 3 up to about 12 carbon atoms.

The term "cycloalkenyl" used alone or as suffix or prefix, refers to a monovalent ring-containing hydrocarbon radical having at least one carbon-carbon double bond and comprising at least 3 up to about 12 carbon atoms.

The term "cycloalkynyl" used alone or as suffix or prefix, refers to a monovalent ring-containing hydrocarbon radical having at least one carbon-carbon triple bond and comprising about 7 up to about 12 carbon atoms.

The term "aryl" used alone or as suffix or prefix, refers to a monovalent hydrocarbon radical having one or more polyunsaturated carbon rings having aromatic character, (e.g., 4n+2 delocalized electrons) and comprising 5 up to about 14 carbon atoms.

The term "arylene" used alone or as suffix or prefix, refers to a divalent hydrocarbon radical having one or more polyunsaturated carbon rings having aromatic character, (e.g., 4n+2 delocalized electrons) and comprising 5 up to about 14 carbon atoms, which serves to links two structures together.

The term "heterocycle" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The term "heteroalkyl" used alone or as a suffix or prefix, refers to a radical formed as a result of replacing one or more carbon atom of an alkyl with one or more heteroatoms selected from N, O, P and S.

The term "heteroaromatic" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s), wherein the ring-containing structure or molecule has an aromatic character (e.g., 4n+2 delocalized electrons).

The term "heterocyclic group," "heterocyclic moiety," "heterocyclic," or "heterocyclo" used alone or as a suffix or prefix, refers to a radical derived from a heterocycle by removing one or more hydrogens therefrom.

The term "heterocyclyl" used alone or as a suffix or prefix, refers a monovalent radical derived from a heterocycle by removing one hydrogen therefrom.

The term "heterocyclylene" used alone or as a suffix or prefix, refers to a divalent radical derived from a heterocycle by removing two hydrogens therefrom, which serves to links two structures together.

The term "heteroaryl" used alone or as a suffix or prefix, refers to a heterocyclyl having aromatic character.

The term "heterocylcoalkyl" used alone or as a suffix or prefix, refers to a heterocyclyl that does not have aromatic character.

The term "heteroarylene" used alone or as a suffix or prefix, refers to a heterocyclylene having aromatic character.

The term "heterocycloalkylene" used alone or as a suffix or prefix, refers to a heterocyclylene that does not have aromatic character.

The term "six-membered" used as prefix refers to a group having a ring that contains six ring atoms.

The term "five-membered" used as prefix refers to a group having a ring that contains five ring atoms.

A five-membered ring heteroaryl is a heteroaryl with a ring having five ring atoms wherein 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

The term "substituted" used as a prefix refers to a structure, molecule or group, wherein one or more hydrogens are replaced with one or more $C_{1-12}$ hydrocarbon groups, or one or more chemical groups containing one or more heteroatoms selected from N, O, S, F, Cl, Br, I, and P. Exemplary chemical groups containing one or more heteroatoms include heterocyclyl, —$NO_2$, —OR, —Cl, —Br, —I, —F, —$CF_3$, —C(=O)R, —C(=O)OH, —$NH_2$, —SH, —NHR, —$NR_2$, —SR, —$SO_3H$, —$SO_2R$, —S(=O)R, —CN, —OH, —C(=O)OR, —C(=O)$NR_2$, —NRC(=O)R, oxo (=O), imino (=NR), thio (=S), and oximino (=N—OR), wherein each "R" is a $C_{1-12}$ hydrocarbyl. For example, substituted phenyl may refer to nitrophenyl, pyridylphenyl, methoxyphenyl, chlorophenyl, aminophenyl, etc., wherein the nitro, pyridyl, methoxy, chloro, and amino groups may replace any suitable hydrogen on the phenyl ring.

The term "substituted" used as a suffix of a first structure, molecule or group, followed by one or more names of chemical groups refers to a second structure, molecule or group, which is a result of replacing one or more hydrogens of the first structure, molecule or group with the one or more named chemical groups. For example, a "phenyl substituted by nitro" refers to nitrophenyl.

The term "optionally substituted" refers to both groups, structures, or molecules that are substituted and those that are not substituted.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles, for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "alkoxy" used alone or as a suffix or prefix, refers to radicals of the general formula —O—R, wherein —R is selected from a hydrocarbon radical. Exemplary alkoxy includes methoxy, ethoxy, propoxy, isopropoxy, butoxy, t-butoxy, isobutoxy, cyclopropylmethoxy, allyloxy, and propargyloxy.

The term "aryloxy" used alone or as suffix or prefix, refers to radicals of the general formula —O—Ar, wherein —Ar is an aryl.

The term "heteroaryloxy" used alone or as suffix or prefix, refers to radicals of the general formula —O—Ar', wherein —Ar' is a heteroaryl.

The term "amine" or "amino" used alone or as a suffix or prefix, refers to radicals of the general formula —NRR', wherein R and R' are independently selected from hydrogen or a hydrocarbon radical.

"Acyl" used alone, as a prefix or suffix, means —C(=O)—R, wherein —R is an optionally substituted hydrocarbyl, hydrogen, amino or alkoxy. Acyl groups include, for example, acetyl, propionyl, benzoyl, phenyl acetyl, carboethoxy, and dimethylcarbamoyl.

Halogen includes fluorine, chlorine, bromine and iodine.

"Halogenated," used as a prefix of a group, means one or more hydrogens on the group is replaced with one or more halogens.

"RT" or "rt" means room temperature.

A first ring group being "fused" with a second ring group means the first ring and the second ring share at least two atoms therebetween.

"Link," "linked," or "linking," unless otherwise specified, means covalently linked or bonded.

When a first group, structure, or atom is "directly connected" to a second group, structure or atom, at least one atom of the first group, structure or atom forms a chemical bond with at least one atom of the second group, structure or atom.

"Saturated carbon" means a carbon atom in a structure, molecule or group wherein all the bonds connected to this carbon atom are single bond. In other words, there is no double or triple bonds connected to this carbon atom and this carbon atom generally adopts an $sp^3$ atomic orbital hybridization.

"Unsaturated carbon" means a carbon atom in a structure, molecule or group wherein at least one bond connected to this carbon atom is not a single bond. In other words, there is at least one double or triple bond connected to this carbon atom and this carbon atom generally adopts a sp or $sp^2$ atomic orbital hybridization.

DESCRIPTION OF PREFERRED EMBODIMENTS

In one aspect, the invention provides a compound of formula I, a pharmaceutically acceptable salt thereof, diastereomers, enantiomers, or mixtures thereof:

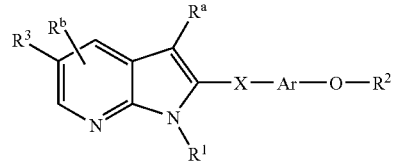

wherein
$R^1$ is a $C_{1-12}$ group;
X is a $C_{1-10}$ divalent group that separates groups connected thereto by one or two saturated carbons;
Ar is $C_{4-12}$ divalent aromatic group;
$R^2$ is optionally substituted $C_{1-6}$hydrocarbyl, optionally substituted $C_{6-10}$aryl, or optionally substituted $C_{3-6}$heteroaryl;
$R^3$ is a $C_{1-12}$ group, wherein the atom of $R^3$ that is directly connected to the six-membered ring of formula I is a nitrogen, or an unsaturated carbon, wherein the unsaturated carbon is connected to an oxygen through a double bond; and
$R^a$ and $R^b$ are —R, —$NO_2$, —OR, —Cl, —Br, —I, —F, —$CF_3$, —C(=O)R, —C(=O)OH, —$NH_2$, —SH, —NHR, —$NR_2$, —SR, —$SO_3H$, —$SO_2R$, —S(=O)R, —CN, —OH, —C(=O)OR, or —NRC(=O)R, wherein R is independently —H or $C_{1-6}$ hydrocarbyl.

Particularly, the compounds of the present invention are those of formula I, wherein
$R^1$ is optionally substituted $C_{1-10}$ hydrocarbyl; optionally substituted $C_{1-10}$acyl; optionally substituted $C_{4-8}$heteroaryl-C(=O)—; $R^4R^5N$—$C_{1-6}$alkyl; $R^4R^5NC(=O)C_{1-6}$alkyl; $R^4O$—$C_{1-6}$alkyl; $R^4OC(=O)$—$C_{1-6}$alkyl; $R^4C(=O)$—$C_{1-6}$alkyl; $R^4C(=O)NR^4$—$C_{1-6}$alkyl; $R^4R^5NSO_2$—$C_{1-6}$alkyl; $R^4CSO_2N(R^5)$—$C_{1-6}$alkyl; $R^4R^5NC(=O)N(R^6)$—$C_{1-6}$alkyl; $R^4R^5NSO_2N(R^6)$—$C_{1-6}$alkyl; optionally substituted aryl-$C_{1-6}$alkyl; optionally substituted aryl-C(=O)—$C_{1-6}$alkyl; optionally substituted heterocyclyl-$C_{1-6}$alkyl; optionally substituted heterocyclyl-C(=O)—$C_{1-6}$alkyl; and $C_{1-10}$hydrocarbylamino;
wherein $R^4$, $R^5$ and $R^6$ are independently selected from —H, $C_{1-6}$alkyl, $C_{2-6}$alkenyl, $C_{2-6}$alkynyl, or a divalent $C_{1-6}$group that together with another divalent $C_{1-6}$group forms a portion of a ring;
$R^2$ is optionally substituted $C_{1-6}$hydrocarbyl, optionally substituted $C_{6-10}$aryl, or optionally substituted $C_{3-6}$heteroaryl;
$R^3$ is selected from:

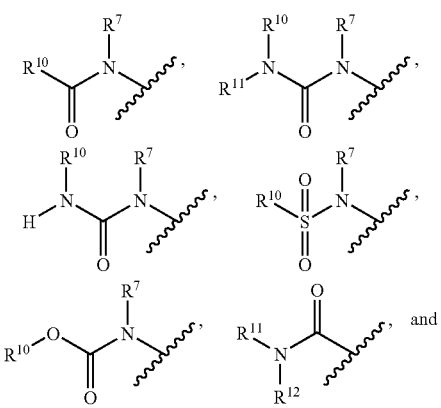

-continued

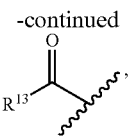

wherein

R$^7$ is selected from —H, optionally substituted C$_{1-6}$alkyl, optionally substituted C$_{2-6}$alkenyl, optionally substituted C$_{2-6}$alkynyl, optionally substituted C$_{3-6}$cycloalkyl, optionally substituted C$_{6-10}$ aryl, or optionally substituted C$_{3-6}$heteroaryl;

R$^{10}$, R$^{11}$, R$^{12}$ and R$^{13}$ are independently selected from optionally substituted C$_{1-6}$alkyl, optionally substituted C$_{2-6}$alkenyl, optionally substituted C$_{2-6}$alkynyl, optionally substituted C$_{3-6}$cycloalkyl, optionally substituted C$_{6-10}$ aryl, or optionally substituted C$_{3-6}$heteroaryl; and R$^a$ and R$^b$ are hydrogen.

More particularly, the compounds of the present invention are those of formula I, wherein R$^1$ is selected from C$_{1-8}$alkyl; C$_{2-8}$alkenyl; C$_{2-8}$alkynyl; optionally substituted aryl-C$_{1-6}$alkyl; R$^4$R$^5$NC$_{1-6}$alkyl; R$^4$OC$_{1-6}$alkyl; C$_{3-6}$cycloalkyl-C$_{1-6}$alkyl; optionally substituted C$_{3-6}$heterocycloalkyl-C$_{1-6}$alkyl; C$_{1-6}$alkylC$_{6-saryl}$; C$_{1-6}$alkyl-C(=O)—; C$_{6-8}$aryl-C(=O)—; C$_{3-8}$heteroaryl-C(=O)—; or optionally substituted C$_{3-6}$heteroaryl-C$_{1-6}$alkyl;

wherein R$^2$ is selected from C$_{1-6}$alkyl, C$_{1-6}$alkyl substituted by at least one fluorine, C$_{2-6}$alkenyl, C$_{2-6}$alkenyl substituted by at least one fluorine, C$_{2-6}$alkynyl, C$_{2-6}$alkynyl substituted by at least one fluorine, optionally substituted C$_{3-6}$cycloalkyl, optionally substituted C$_{6-10}$aryl, and optionally substituted C$_{3-6}$heteroaryl;

R$^4$, R$^5$ and R$^6$ are independently selected from the group consisting of —H, C$_{1-6}$alkyl, C$_{2-6}$alkenyl, C$_{2-6}$alkynyl, and a divalent C$_{1-6}$group that together with another divalent C$_{1-6}$group forms a portion of a ring; and X is selected from the group consisting of —NR$^6$—, —CH$_2$—CH$_2$—, —CH=CH—, —O—, —C(R$^8$)(R$^9$)—, and —S(O)$_q$—, wherein q is 0, 1 or 2, wherein R$^8$ and R$^9$ are independently C$_{1-6}$alkyl, C$_{2-6}$alkenyl, C$_{2-6}$alkynyl, C$_{1-6}$alkoxy, —OH, or —H; at most one of R$^8$ and R$^9$ is —OH.

R$^3$ is selected from:

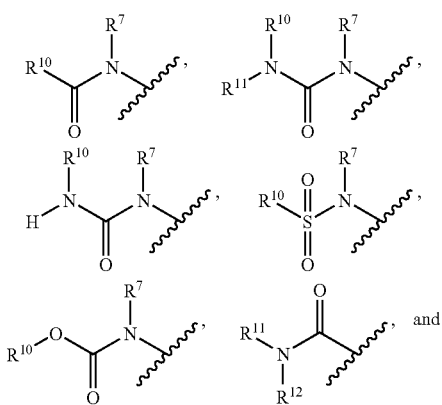

-continued

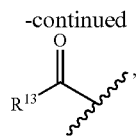

wherein

R$^7$ is selected from —H, optionally substituted C$_{1-6}$alkyl, optionally substituted C$_{2-6}$alkenyl, optionally substituted C$_{2-6}$alkynyl, optionally substituted C$_{3-6}$cycloalkyl, optionally substituted C6-10 aryl, or optionally substituted C$_{3-6}$heteroaryl;

R$^{10}$, R$^{11}$, R$^{12}$ and R$^{13}$ are independently selected from optionally substituted C$_{1-6}$alkyl, optionally substituted C$_{2-6}$alkenyl, optionally substituted C$_{2-6}$alkynyl, optionally substituted C$_{3-6}$cycloalkyl, optionally substituted C$_{6-10}$ aryl, or optionally substituted C$_{3-6}$heteroaryl; and R$^a$ and R$^b$ are hydrogen.

In a more particular embodiment, the compounds of the present invention are those of formula I, wherein R$^1$ is selected from C$_{1-6}$alkyl; C$_{2-6}$alkenyl; C$_{2-6}$ alkynyl; optionally substituted C$_{3-6}$cycloalkylmethyl; optionally substituted C$_{3-6}$heterocycloalkylmethyl;

X is —CH$_2$—;

Ar is phenylene or pyridylene;

R$^2$ is selected from —CH$_3$, —CH$_2$CH$_3$, —CH(CH$_3$)$_2$, —CH$_2$CF$_3$, CF$_3$, cyclopropyl, cyclobutyl, cyclopentyl, cyclohexyl, pyridyl and phenyl; and R$^3$ is selected from:

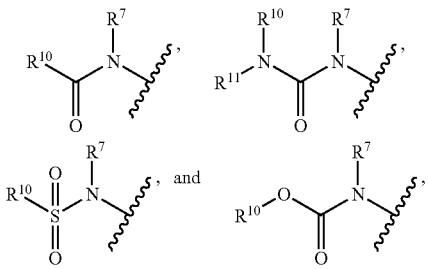

wherein, R$^7$ is selected from —H and methyl; R$^{10}$ and R$^{11}$ are independently selected from optionally substituted C$_{1-6}$alkyl, optionally substituted C$_{2-6}$alkenyl, optionally substituted C$_{2-6}$alkynyl, optionally substituted C$_{3-6}$cycloalkyl, optionally substituted C$_{6-10}$ aryl, or optionally substituted C$_{3-6}$heteroaryl.

In another more particular embodiment, the compounds of the present invention are those of formula I, wherein R$^1$ is selected from C$_{1-6}$alkyl; C$_{2-6}$alkenyl; C$_{2-6}$ alkynyl; optionally substituted C$_{3-6}$cycloalkylmethyl; optionally substituted C$_{3-6}$heterocycloalkylmethyl;

X is —CH$_2$—;

Ar is selected from the group consisting of an optionally substituted para-arylene; an optionally substituted a six-membered para-heteroarylene;

R$^2$ is selected from —CH$_3$, —CH$_2$CH$_3$, —CH(CH$_3$)$_2$, —CH$_2$CF$_3$, CF$_3$, cyclopropyl, cyclobutyl, cyclopentyl, cyclohexyl, pyridyl and phenyl; and $R^3$ is selected from:

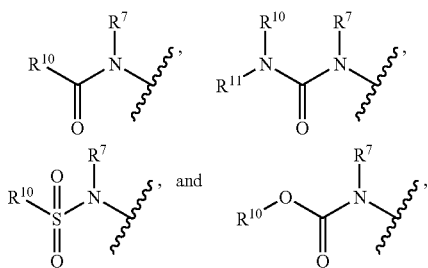

wherein, $R^7$ is selected from —H and methyl; $R^{10}$ and $R^{11}$ are selected from optionally substituted $C_{1-6}$alkyl, optionally substituted $C_{2-6}$alkenyl, optionally substituted $C_{2-6}$alkynyl, optionally substituted $C_{3-6}$cycloalkyl, optionally substituted $C_{6-10}$aryl, or optionally substituted $C_{3-6}$heteroaryl.

Most particularly, the compounds of the present invention are those of formula I, wherein $R^1$ is selected from optionally substituted $C_{3-6}$cycloalkylmethyl; and optionally substituted $C_{3-6}$heterocycloalkylmethyl;

X is —$CH_2$—;

Ar is para-phenylene or para-pyridylene;

$R^2$ is methyl, or ethyl; and $R^3$ is selected from:

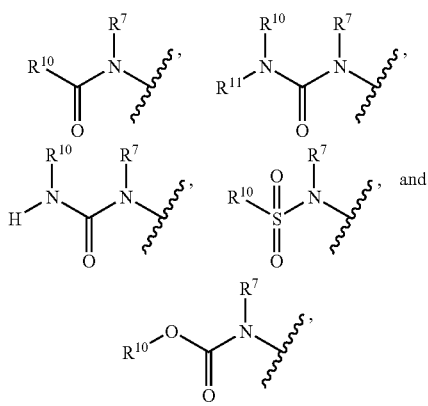

wherein, $R^7$ is selected from —H and methyl; $R^{10}$ and $R^{11}$ are selected from $C_{1-6}$alkyl, $C_{3-6}$cylcoalkyl, phenyl optionally substituted with halogen, nitro, $C_{1-3}$alkyl, —$COOR^{14}$, —OH, cyano, trifluormethyl, $C_{1-3}$alkyloxy; $C_{3-6}$heteroaryl optionally substituted with halogen, nitro, $C_{1-3}$alkyl, —$COOR^{14}$, —OH, cyano, trifluormethyl, $C_{1-3}$alkyloxy, wherein $R^{14}$ is a $C_{1-3}$alkyl.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be appreciated that certain compounds of the present invention may exist as geometrical isomers, for example E and Z isomers of alkenes. The present invention includes any geometrical isomer of a compound of Formula I. It will further be understood that the present invention encompasses tautomers of the compounds of the formula I.

It will also be understood that certain compounds of the present invention may exist in solvated, for example hydrated, as well as unsolvated forms. It will further be understood that the present invention encompasses all such solvated forms of the compounds of the formula I.

Within the scope of the invention are also salts of the compounds of the formula I. Generally, pharmaceutically acceptable salts of compounds of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound of formula I above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

We have discovered that the compounds of the invention have activity as pharmaceuticals, in particular as modulators or ligands such as agonists, partial agonists, inverse agonist or antagonists of $CB_1/CB_2$ receptors. More particularly, the compounds of the invention exhibit selective activity as agonists of the $CB_1/CB_2$ receptors, and are useful in the relief of pain, particularly chronic pain, e.g., chronic inflammatory pain, neuropathic pain, back pain, cancer pain and visceral pain. Compounds of the present invention will also be useful in treating acute pain, anxiety disorders, gastrointestinal disorders, cardiovascular disorders, multiple sclerosis, Parkinson's disease, Huntington's chorea, Alzheimer's disease and/or cancers of the immune system or cells thereof. Additionally, compounds of the present invention are useful in other disease states in which degeneration or dysfunction of $CB_1/CB_2$ receptors is present or implicated.

Thus, the invention provides a compound of formula I, or pharmaceutically acceptable salt or solvate thereof, as hereinbefore defined for use in therapy.

In a further aspect, the present invention provides the use of a compound of formula I, or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The term "therapeutic" and "therapeutically" should be contrued accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

The compounds of the present invention are useful in therapy, especially for the therapy of various pain conditions including, but not limited to: acute pain, chronic pain, neuropathic pain, back pain, cancer pain, and visceral pain.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the invention, the route of administration may be orally, intravenously or intramuscularly.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid and liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (per cent by weight), more preferably from 0.10 to 50% w,
of the compound of the invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

Within the scope of the invention is the use of any compound of formula I as defined above for the manufacture of a medicament.

Also within the scope of the invention is the use of any compound of formula I for the manufacture of a medicament for the therapy of pain.

Additionally provided is the use of any compound according to Formula I for the manufacture of a medicament for the therapy of various pain conditions including, but not limited to: acute pain, chronic pain, neuropathic pain, back pain, cancer pain, and visceral pain.

A further aspect of the invention is a method for therapy of a subject suffering from any of the conditions discussed above, whereby an effective amount of a compound according to the formula I above, is administered to a patient in need of such therapy.

Additionally, there is provided a pharmaceutical composition comprising a compound of Formula I, or a pharmaceutically acceptable salt thereof, in association with a pharmaceutically acceptable carrier.

Particularly, there is provided a pharmaceutical composition comprising a compound of Formula I, or a pharmaceutically acceptable salt thereof, in association with a pharmaceutically acceptable carrier for therapy, more particularly for therapy of pain.

Further, there is provided a pharmaceutical composition comprising a compound of Formula I, or a pharmaceutically acceptable salt thereof, in association with a pharmaceutically acceptable carrier use in any of the conditions discussed above.

In another aspect, the present invention provides a method for preparing a compound of formula II,

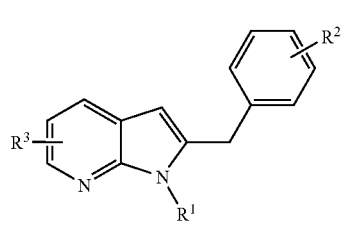

comprising the steps of
a) reacting a compound of formula III,

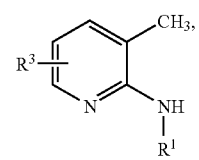

with a base having a pKa of more than 20;

b) reacting a product formed in step a) with a compound of formula IV,

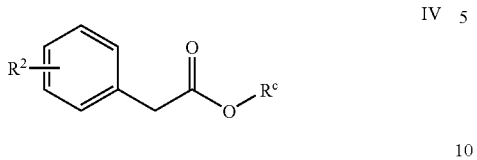

to form the compound of formula II,
wherein $R^1$, $R^2$, and $R^3$ are as previously defined, and $R^c$ is $C_{1-4}$alkyl.

Particularly, the present invention provides a method of preparing a compound of formula II, wherein the strong base having a pKa of more than 20 is t-butyl lithium or n-butyl lithium.

In a further aspect, the present invention provides a process for preparing a compound of formula V,

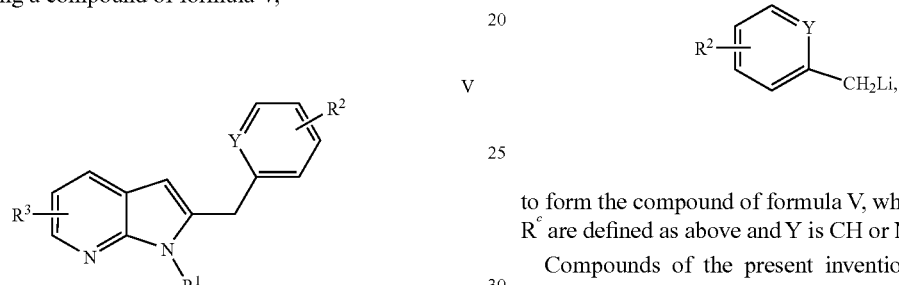

comprising the step of reacting a compound of formula VI,

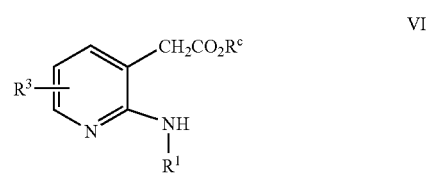

with a compound of formula VII,

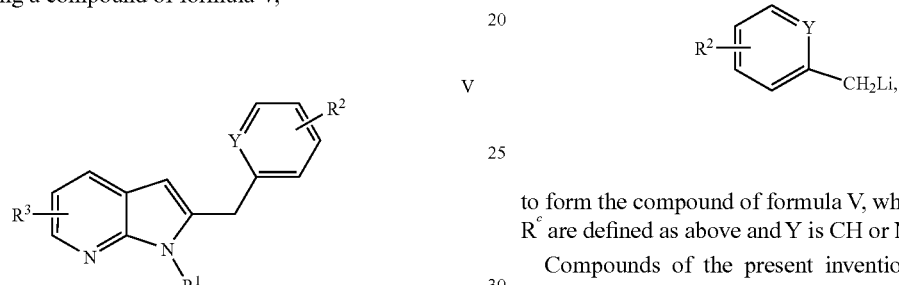

to form the compound of formula V, wherein $R^1$, $R^2$, $R^3$ and $R^c$ are defined as above and Y is CH or N.

Compounds of the present invention may be prepared according to the synthetic routes as depicted in Schemes 1 and 2 using one or more methods disclosed above.

Scheme 1

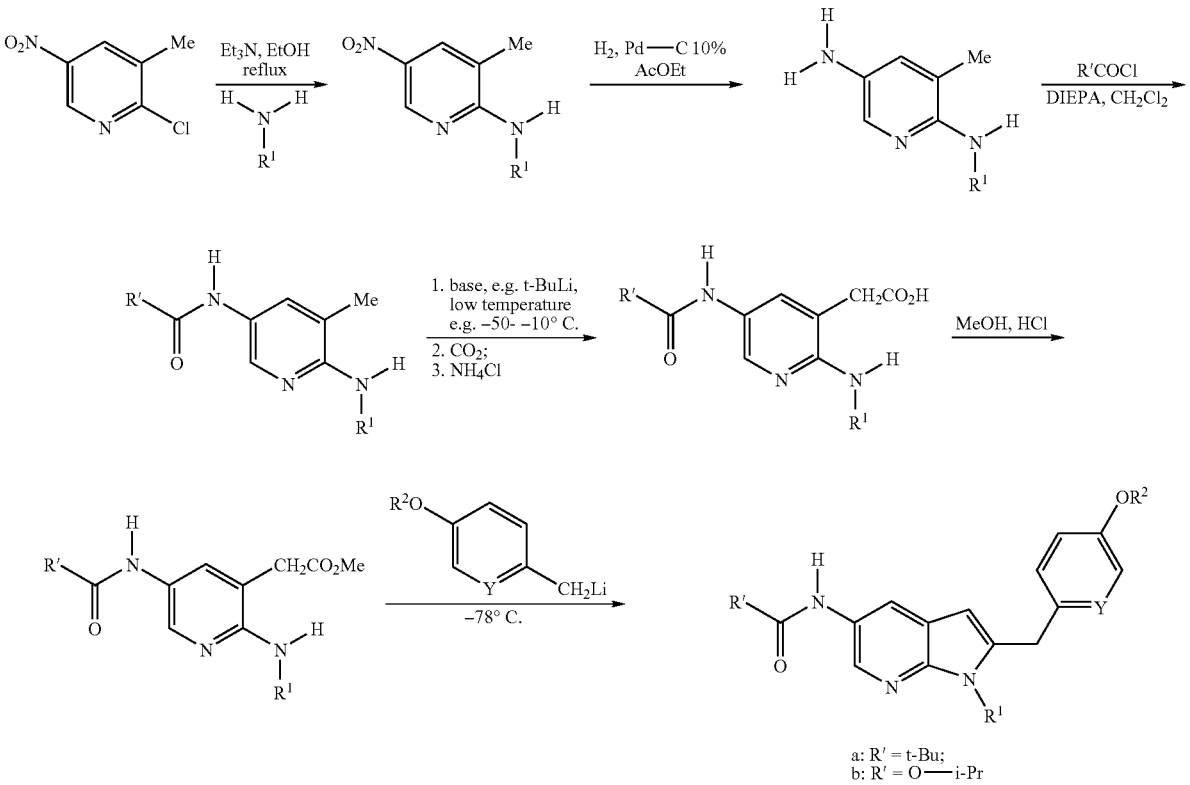

a: R' = t-Bu;
b: R' = O—i-Pr

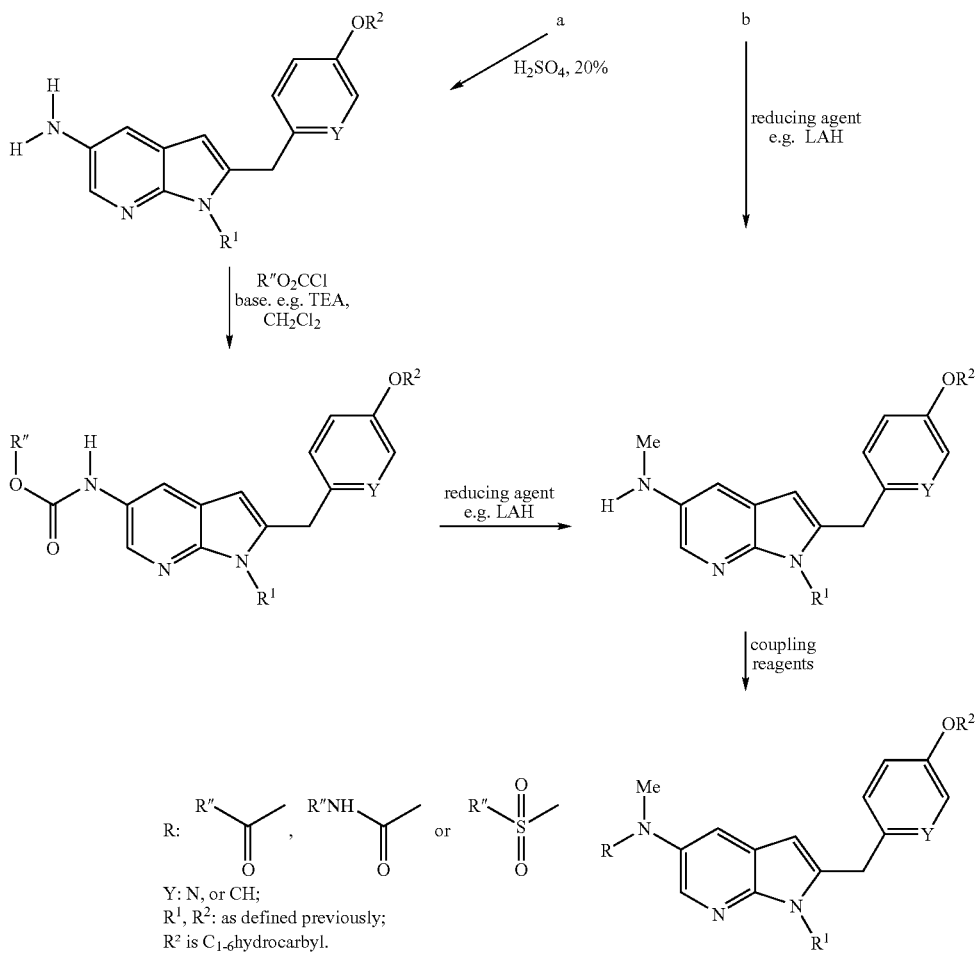
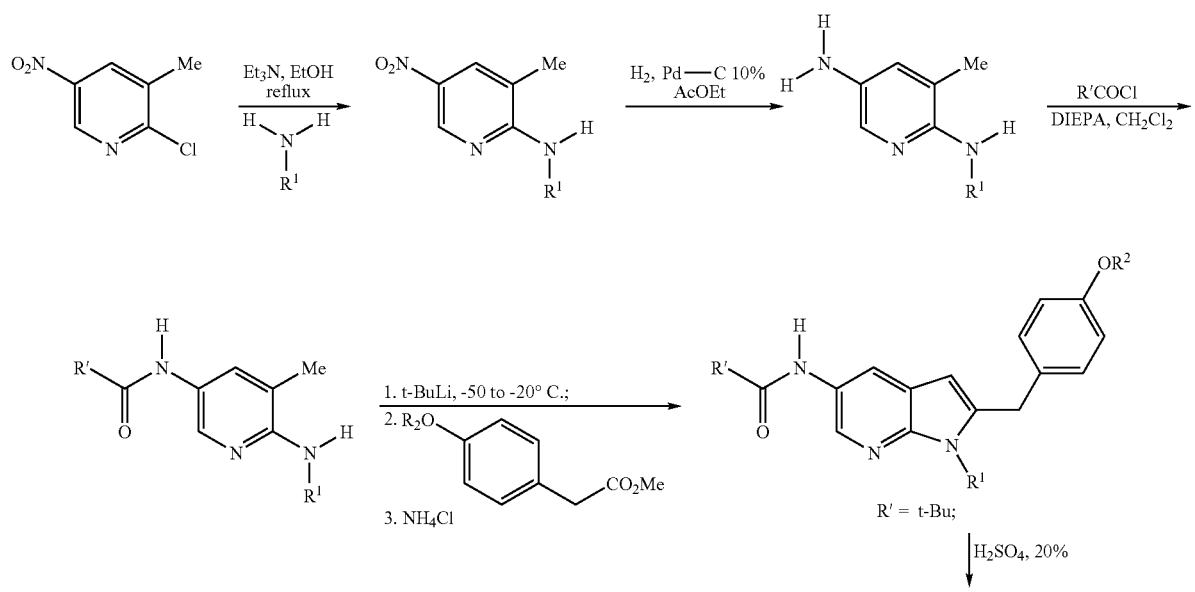
Scheme 2

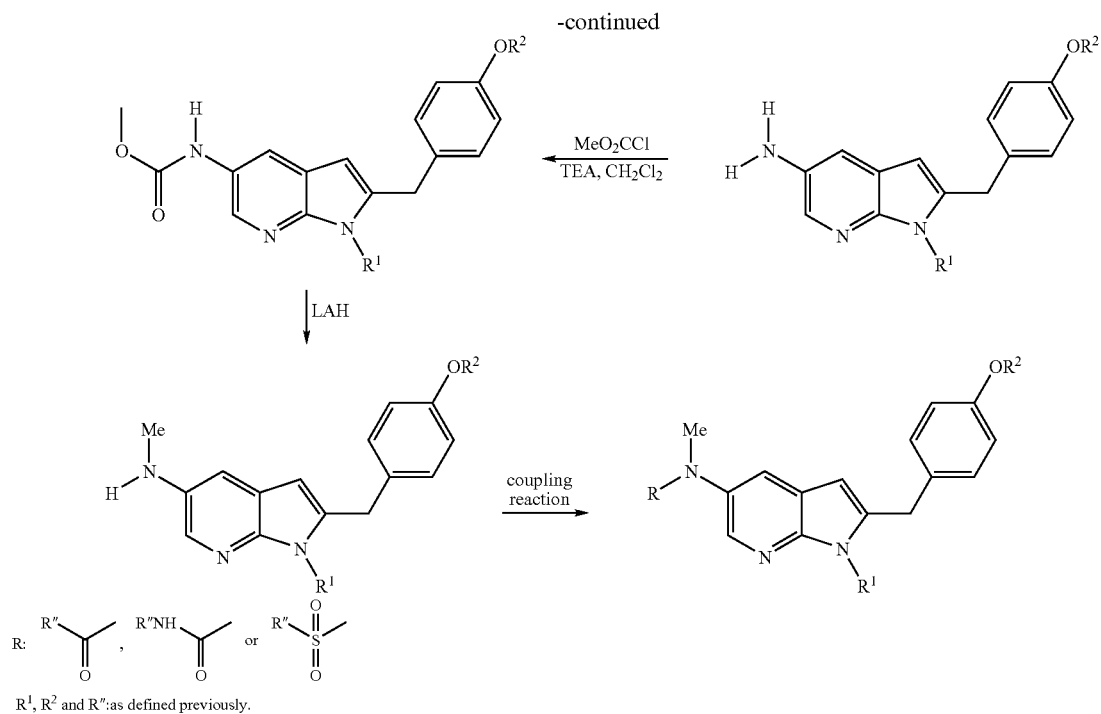
Table 1 exemplifies some of the compounds of the present invention that were made according to the schemes and methods described above. These compounds were found to be active towards human CB1/CB2 receptors based on the test results of using one or more assays described below.
Table 1. Examplary Compounds of the Invention.
| Compound No. | Structure |
| --- | --- |
| 1 | 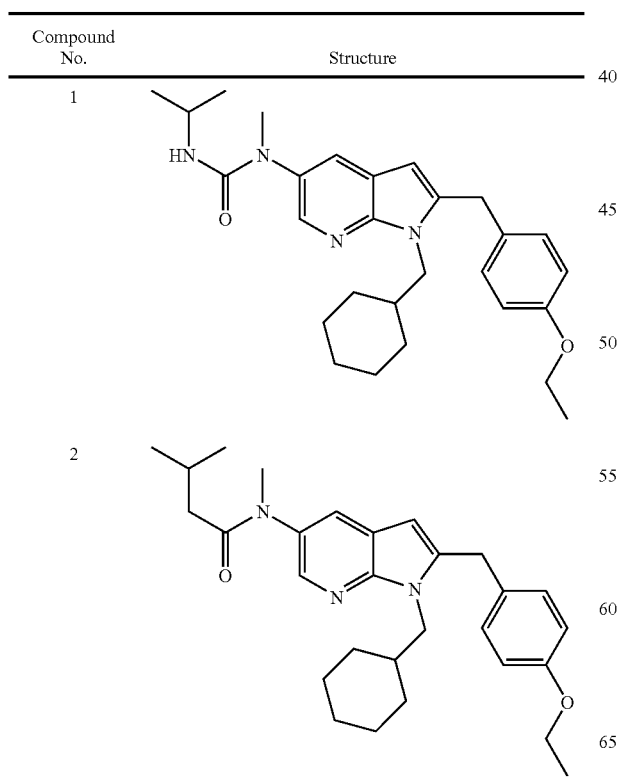 |
| 2 | 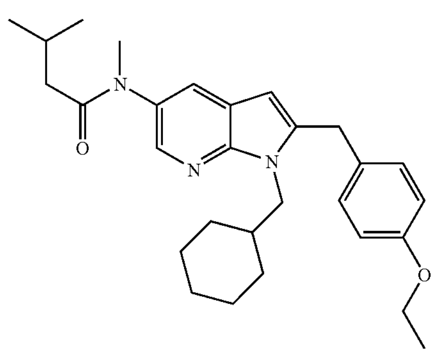 |
| 3 | 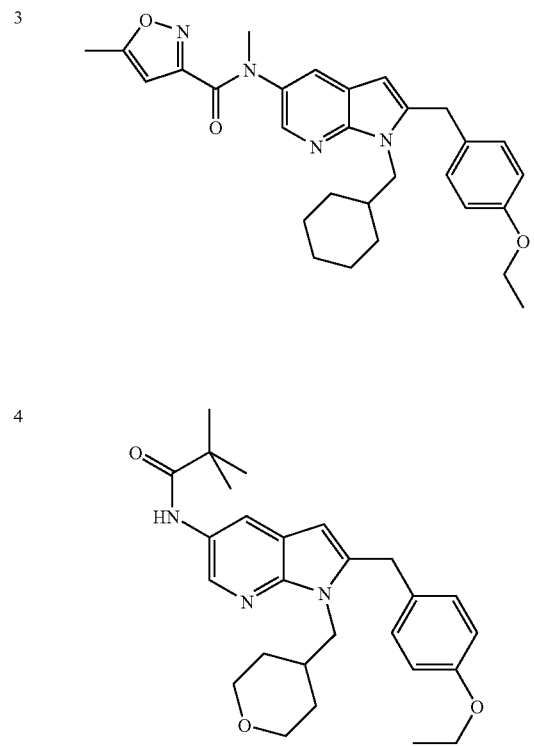 |
| 4 | |

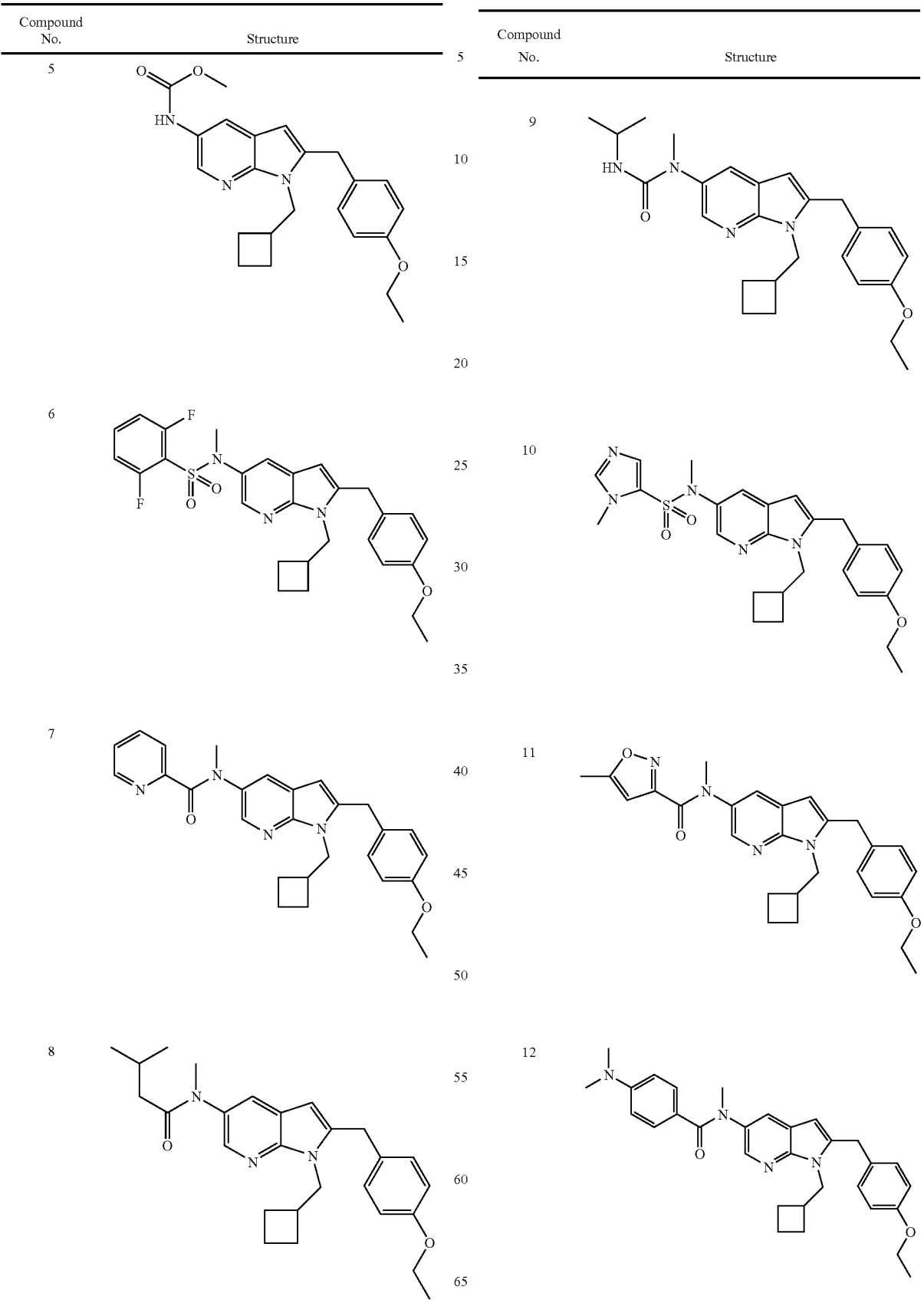

-continued
| Compound No. | Structure |
|---|---|
| 13 | 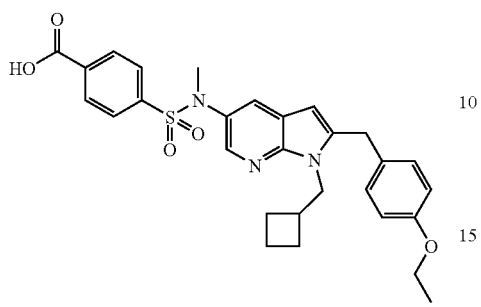 |
| 14 | 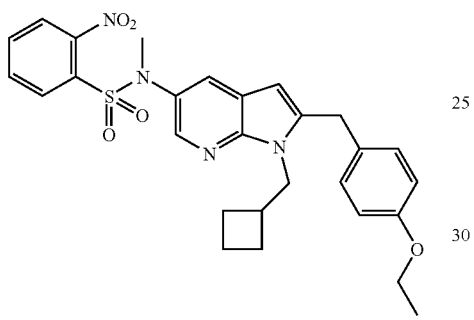 |
| 15 | 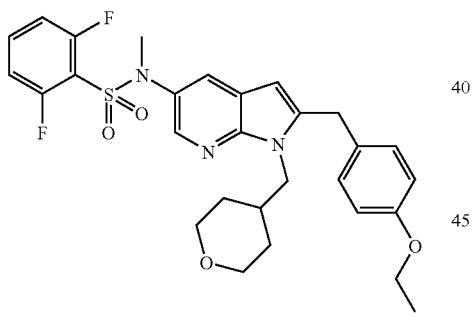 |
| 16 | 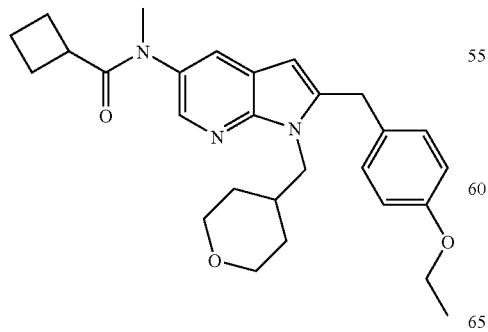 |
-continued
| Compound No. | Structure |
|---|---|
| 17 | 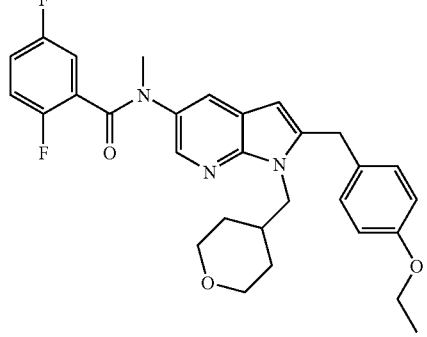 |
| 18 | 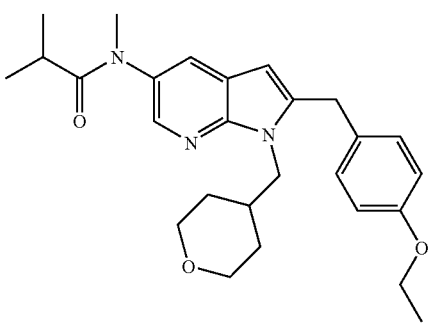 |
| 19 | 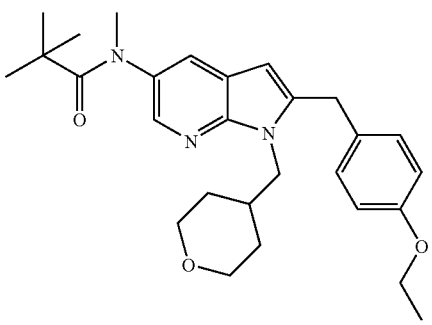 |
| 20 | 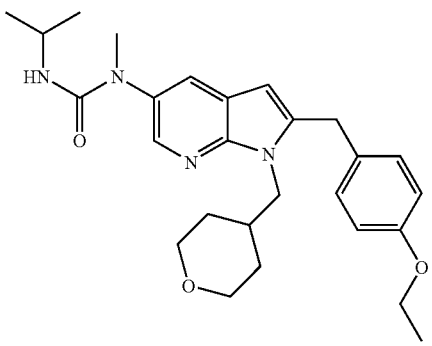 |

-continued
| Compound No. | Structure |
|---|---|
| 21 | 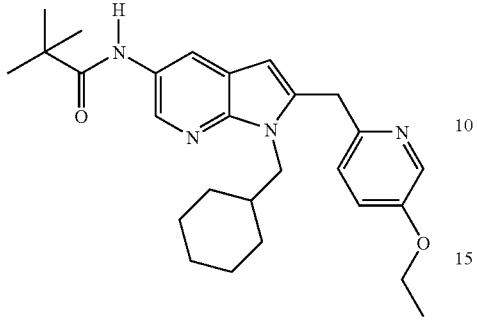 |
| 22 | 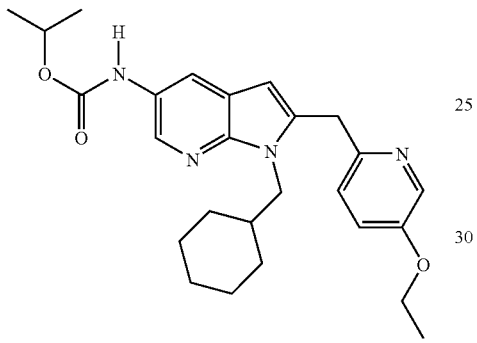 |
| 23 | 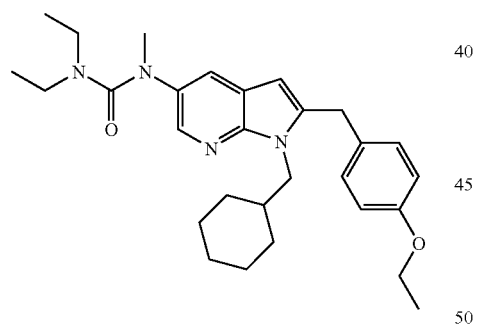 |
| 24 | 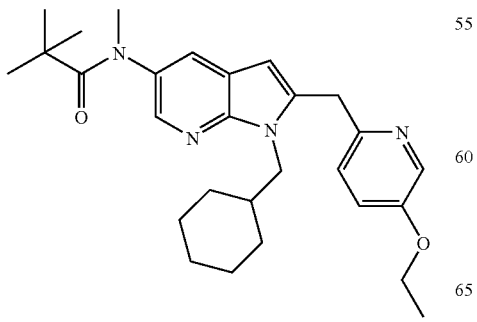 |
-continued
| Compound No. | Structure |
|---|---|
| 25 | 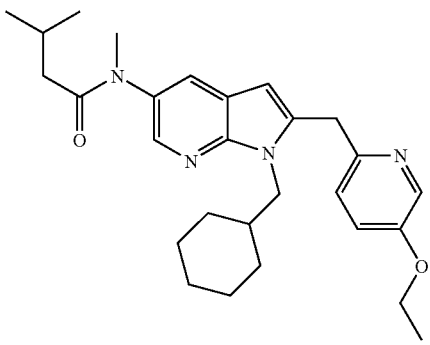 |
| 26 | 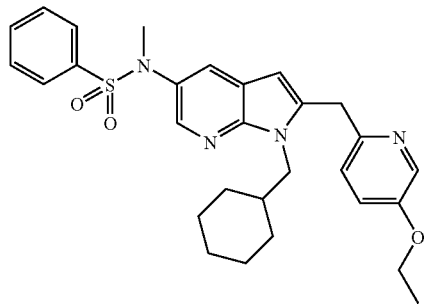 |
| 27 | 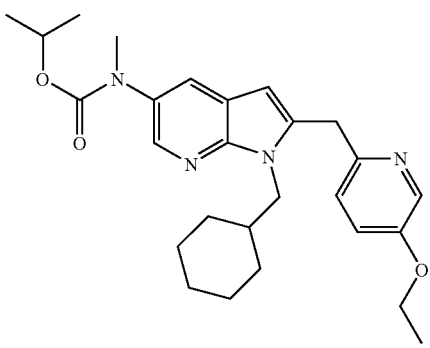 |
| 28 | 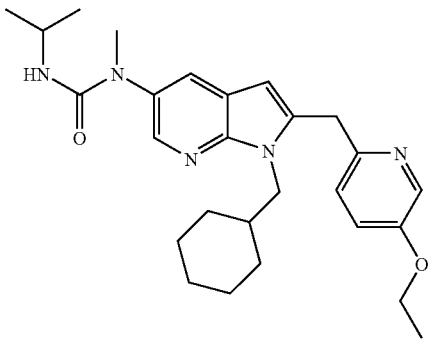 |

-continued

| Compound No. | Structure |
|---|---|
| 29 | 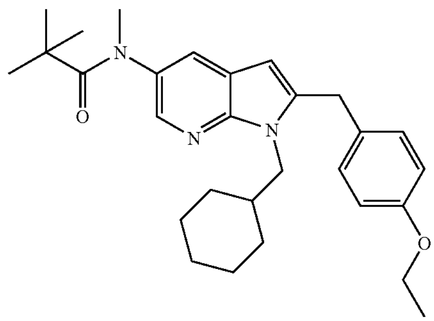 |
| 30 | 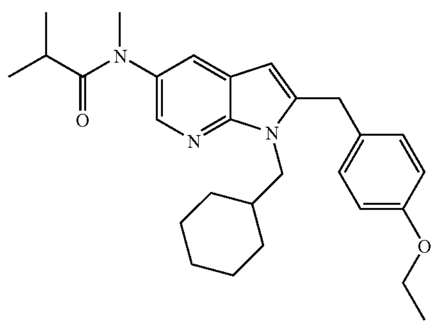 |
| 31 | 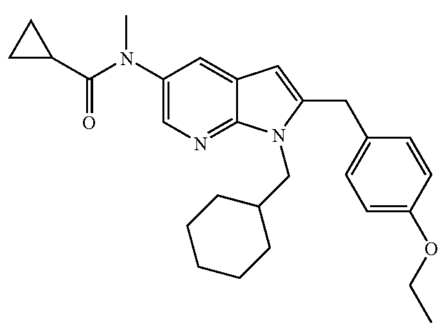 |
| 32 | 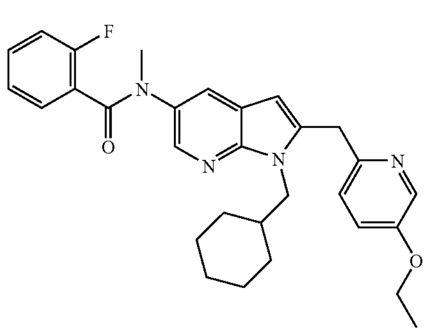 |

-continued

| Compound No. | Structure |
|---|---|
| 33 | 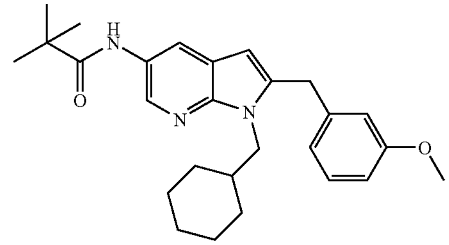 |
| 34 | 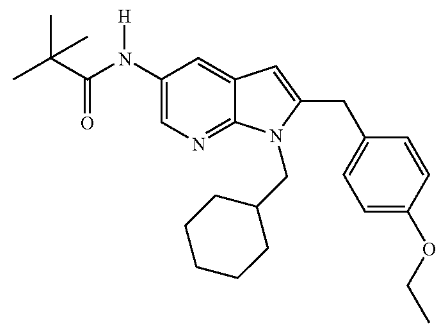 |
| 35 | 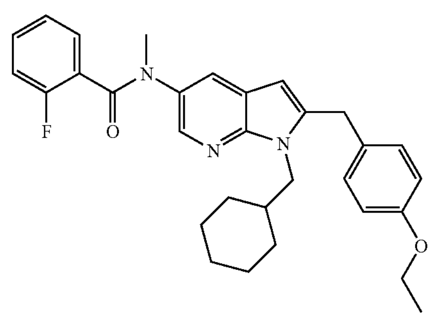 |
| 36 | 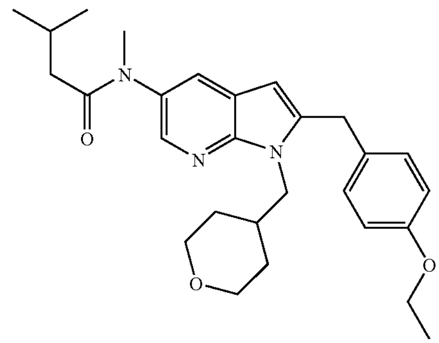 |

-continued

| Compound No. | Structure |
|---|---|
| 37 | (structure shown) |
| 38 | (structure shown) |

Biological Evaluation hCB$_1$ and hCB$_2$ Receptor Binding

Human CB$_1$ receptor from Receptor Biology (hCB1) or human CB$_2$ receptor from BioSignal (hCB2) membranes are thawed at 37° C., passed 3 times through a 25-gauge blunt-end needle, diluted in the cannabinoid binding buffer (50 mM Tris, 2.5 mM EDTA, 5 mM MgCl$_2$, and 0.5 mg/mL BSA fatty acid free, pH 7.4) and aliquots containing the appropriate amount of protein are distributed in 96-well plates. The IC$_{50}$ of the compounds of the invention at hCB$_1$ and hCB$_2$ are evaluated from 10-point dose-response curves done with $^3$H-CP55,940 at 20000 to 25000 dpm per well (0.17-0.21 nM) in a final volume of 300 µl. The total and non-specific binding are determined in the absence and presence of 0.2 µM of HU210 respectively. The plates are vortexed and incubated for 60 minutes at room temperature, filtered through Unifilters GF/B (presoaked in 0.1% polyethyleneimine) with the Tomtec or Packard harvester using 3 mL of wash buffer (50 mM Tris, 5 mM MgCl$_2$, 0.5 mg BSA pH 7.0). The filters are dried for 1 hour at 55° C. The radioactivity (cpm) is counted in a TopCount (Packard) after adding 65 µl/well of MS-20 scintillation liquid.

Based on the above assays, the dissociation constant (Ki) for a particular compound of the invention towards a particular receptor is determined using the following equation:

$$Ki=IC_{50}/(1+[rad]/Kd),$$

Wherein IC$_{50}$ is the concentration of the compound of the invention at which 50% displacement has been observed;

[rad] is a standard or reference radioactive ligand concentration at that moment; and Kd is the dissociation constant of the radioactive ligand towards the particular receptor.

Using above-mentioned assays, the Ki towards human CB1 receptors for compounds 1-38 of the invention is measured to be in the range of 29-5852 nM. The Ki towards human CB2 receptors for compounds 1-38 of the invention is measured to be in the range of 0.7-753 nM.

EXAMPLES

The invention will further be described in more detail by the following Examples which describe methods whereby compounds of the present invention may be prepared, purified, analyzed and biologically tested, and which are not to be construed as limiting the invention.

Example 1

N-[1-(cyclohexylmethyl)-2-[(4-ethoxyphenyl)methyl]-1H-pyrrolo[2,3-b]pyridin-5-yl]-2,2-dimethyl-propanamide

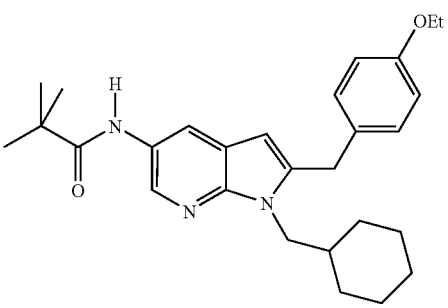

Step A. N-(Cyclohexylmethyl)-3-methyl-5-nitro-2-pyridinamine:

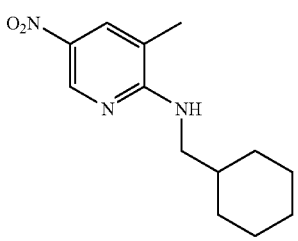

To a solution of 2-chloro-3-methyl-5-nitropyridine (3.45 g, 20 mmol) in EtOH (100 mL) and triethylamine (5 mL) was added cyclohexylmethylamine (4.52 g, 40 mmol) at room temperature. The reaction mixture was refluxed for 12 hr, allowed to cool down to room temperature. After condensation, the residue was diluted with AcOEt, washed with 1 N NH$_4$OH and brine, dried over MgSO$_4$. Removal of solvents provided the desired product (4.90 g, 98%), which was used directly in the next step. $^1$H-NMR (CDCl$_3$): δ 1.02 (m, 2H), 1.23 (m, 3H), 1.75 (m, 6H), 2.16 (s, 3H), 3.46 (m, 2H), 4.98 (brs, 1H), 8.00 (s, 1H), 8.96 (s, 1H). MS (ESI) (M+H)$^+$ 250.31

Step B. N²-(cyclohexylmethyl)-3-methyl-2,5-pyridinediamine:

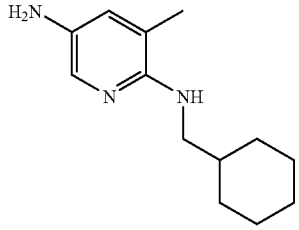

The above product was hydrogenated in ethyl acetate (150 mL) catalyzed by 10% Pd/C (200 mg) at 35-50 psi $H_2$ for 4 hr. The reaction mixture was filtered through Diatomaceous earth, and removal of solvents gave a product, which was purified by flashmaster to give the desired product (4.14 g, 96%). $^1$H-NMR (CDCl$_3$): δ 1.01 (m, 2H), 1.24 (m, 3H), 1.60 (m, 1H), 1.73 (m, 3H), 1.84 (m, 2H), 2.07 (s, 3H), 3.24 (d, J=6.8 Hz, 2H), 6.79 (s, 1H), 7.61 (s, 1H). MS (ESI) (M+H)$^+$ 220.26

Step C. N-[6-[(cycloheylmethyl)amino]-5-methyl-3-pyridinyl]-2,2-dimethyl-propanamide:

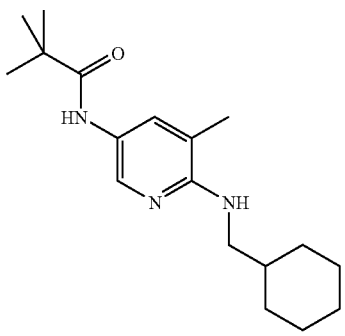

To a stirred solution of N²-(cyclohexylmethyl)-3-methyl-2,5-pyridinediamine (4.14 g, 18.9 mmol), diisopropylethylamine (5 mL) in CH$_2$Cl$_2$ (100 mL) was added dropwise trimethylacetyl chloride (2.4 g, 20 mmol) at −50° C. The reaction was allowed to warm up to 0° C. and then condensed under vacuum, diluted with AcOEt (200 mL), washed with 1N NH$_4$OH (100 mL), brine (50 mL), and dried over MgSO$_4$. Removal of solvent afforded the product as a solid (5.66 g, 99%). $^1$H-NMR (CD$_3$OD, TFA salt): δ 1.02 (m, 2H), 1.27 (s, 9H), 1.28 (m, 3H), 1.80 (m, 6H), 2.27 (s, 3H), 3.25 (d, J=7.6 Hz, 2H), 7.83 (s, 1H), 8.29 (s, 1H). MS (ESI) (M+H)$^+$303.30

Step D. N-[1-(cyclohexylmethyl)-2-[(4-ethoxyphenyl)methyl]-1H-pyrrolo[2,3-b]pyridin-5-yl]-2,2-dimethyl-propanamide:

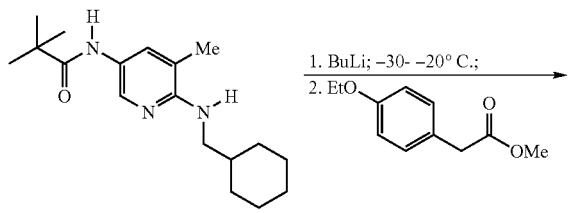

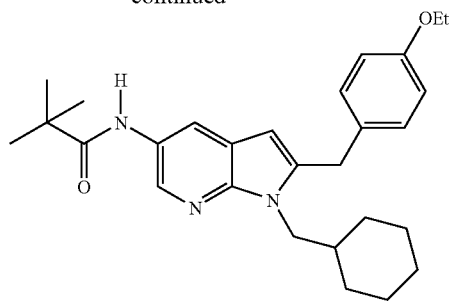

To a solution of N-[6-[(cyclohexylmethyl)amino]-5-methyl-3-pyridinyl]-2,2-dimethyl-propanamide (606 mg, 2.0 mmol) in dry THF was added a solution of BuLi (2.0 M, 4.5 mL, 9.0 mmol) at −50° C. The reaction mixture was warmed up to −20° C. and stirred for an additional 1 h at the temperature prior to addition of a solution of methyl 4-ethoxy-benzeneacetic acid ester (392 mg, 2.0 mmol) in 1 mL THF. After 30 min, The reaction mixture was quenched with aqueous NH$_4$Cl solution, and extracted with ethyl acetate (2×60 mL). The combined organic layers were washed with brine and dried over MgSO$_4$. Removal of solvents gave a product, which was purified by Falshmaster to give the desired product 14 (350 mg, 39%): $^1$H-NMR (CD$_3$OD): δ 1.08 (m, 5H), 1.32 (s, 9H), 1.35 (t, J=6.4 Hz, 3H), 1.42 (m, 2H), 1.69 (m, 4H), 4.00 (q, J=6.4 Hz, 2H), 4.02 (d, J=7.6 Hz, 2H), 4.15 (s, 2H), 6.34 (s, 1H), 6.87 (d, J=8.4 Hz, 2H), 7.14 (d, J=8.4 Hz, 2H), 8.34 (s, 1H), 8.55 (s, 1H). Anal. Calcd. for C$_{28}$H$_{37}$N$_3$O$_2$+0.50 H$_2$O: C, 73.65; H, 8.39. Found: C, 73.76; H, 8.65; Exact mass Calcd. For C$_{28}$H$_{37}$N$_3$O$_2$+1, 448.2964, found: 448.3017 (M$^+$+1).

Example 2

N-[1-(cyclohexylmethyl)-2-[(3-methoxyphenyl)methyl]-1H-pyrrolo[2,3-b]pyridin-5-yl]-2,2-dimethyl-propanamide

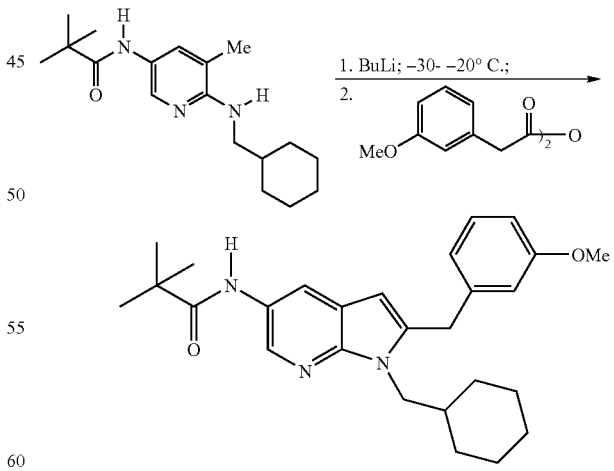

Following the procedure 1D in the Example 1, using 3-methoxyphenylacetic anhydride (314 mg, 1.0 mmol) and N-[6-[(cyclohexylmethyl)amino]-5-methyl-3-pyridinyl]-2,2-dimethyl-propanamide (303 mg, 1.0 mmol), provided the desired title compound (234 mg, 54%): $^1$H-NMR (CD$_3$OD, TFA salt): δ 1.12 (m, 5H), 1.36 (s, 9H), 1.52 (m, 2H), 1.72 (m, 4H), 3.81 (s, 3H), 4.05 (d, J=7.6 Hz, 2H), 4.20 (s, 2H), 6.36 (s, 1H), 6.92 (d, J=8.4 Hz, 2H), 7.20 (d, J=8.4 Hz, 2H), 8.29 (s, 1H), 8.51 (s, 1H). Anal. Calcd. for $C_{27}H_{35}N_3O_2$+0.70 TFA: C, 66.44; H, 7.01, N, 8.18. Found: C, 66.23; H, 7.32, N, 7.84, MS (ESI) (M+H)$^+$434.02(MH+).

Example 3

N-[1-(cyclohexylmethyl)-2-[(4-ethoxyphenyl)methyl]-1H-pyrrolo[2,3-b]pyridin-5-yl]-N-methyl-N'-(1-methylethyl)-urea

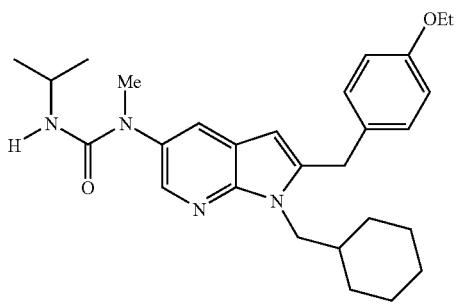

Step A. 1-(cyclohexylmethyl)-2-[(4-ethoxyphenyl)methyl]-N-methyl-1H-pyrrolo[2,3-b]pyridin-5-amine

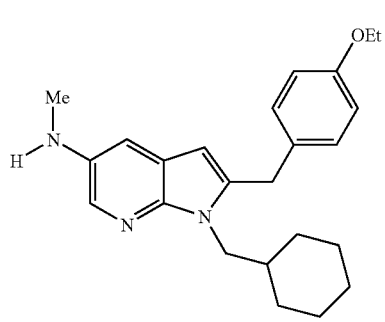

A solution of N-[1-(cyclohexylmethyl)-2-[(4-ethoxyphenyl)methyl]-1H-pyrrolo[2,3-b]pyridin-5-yl]-2,2-dimethylpropanamide (350 mg, 0.78 mmol) in dioxane (30 mL) and 20% $H_2SO_4$ (30 mL) was refluxed overnight, and then allowed to cool down to room temperature. After condensation, the residue was diluted with AcOEt, washed with 1 N $NH_4OH$ and brine, dried over $MgSO_4$. Removal of solvents provided the desired product for the next step (180 mg, 64%), which was used directly in the next step. MS (ESI) (M+H)$^+$ 364.23.

To a stirred solution of the product formed in the last step (180 mg, 0.50 mmol), diisopropylethylamine (1 mL) in $CH_2Cl_2$ (30 mL) was added dropwise methyl chloroformate (0.2 mL) at −30° C. The reaction mixture was allowed to warm up to 0° C., and then condensed under vacuum. The residue was diluted with AcOEt, washed with 1 N $NH_4OH$ and brine, dried over $MgSO_4$. Removal of solvents provided a desired product, which was used directly in the next step. $^1$H-NMR (CDCl$_3$): δ 0.86-1.08 (m, 5H), 1.40 (t, J=6.4 Hz, 3H), 1.63 (m, 6H), 3.75 (s, 3H), 3.98 (d, J=7.6 Hz, 2H), 4.00 (q, J=6.4 Hz, 2H), 4.02 (s, 2H), 6.06 (s, 1H), 6.82 (d, J=8.4 Hz, 2H), 7.08 (d, J=8.4 Hz, 2H), 8.00 (brs, 1H), 8.12 (s, 1H). Exact mass Calcd. For $C_{24}H_{31}N_3O_3$+1, 422.2444, found: 422.2592 (M$^+$+1).

To a solution of the product formed in the last step, methyl carbamate in THF was dropwise added a solution of HCl (1M, 1 mL in diethyl ether) at −20° C. After 10 min, LiAlH$_4$ (0.72 g) was added to the solution. The reaction mixture was stirred at room temperature overnight, and quenched carefully at −20° C. by adding MeOH (5 mL) and H$_2$O (3 mL), diluted with Et$_2$O (50 mL), and then added Na$_2$SO$_4$ (10 g). The resulting mixture was stirred for 2 hr at r.t. After filtration, the organic solution was concentrated in vacuo to afford a product 1-(cyclohexylmethyl)-2-[(4-ethoxyphenyl)methyl]-N-methyl-1H-pyrrolo[2,3-b]pyridin-5-amine (175 mg, 93% for two steps), which was used in the next steps without further purification. $^1$H-NMR (CDCl$_3$): δ 1.02 (m, 2H), 1.20 (m, 3H), 1.39 (t, J=6.8 Hz, 3H), 1.54 (m, 2H), 1.64 (m, 3H), 1.82 (m, 1H), 2.84 (s, 3H), 3.92 (d, J=7.6 Hz, 2H), 3.99 (q, J=6.8 Hz, 2H), 4.03 (s, 2H), 5.96 (s, 1H), 6.83 (d, J=8.4 Hz, 2H), 7.05 (d, J=2.4 Hz, 1H), 7.10 (d, J=8.4 Hz, 2H), 7.80 (d, J=2.4 Hz, 1H). MS (ESI) (M+H)$^+$378.25.

Step B. N-[1-(cyclohexylmethyl)-2-[(4-ethoxyphenyl)methyl]-1H-pyrrolo[2,3-b]pyridin-5-yl]-N-methyl-N'-(1-methylethyl)-urea

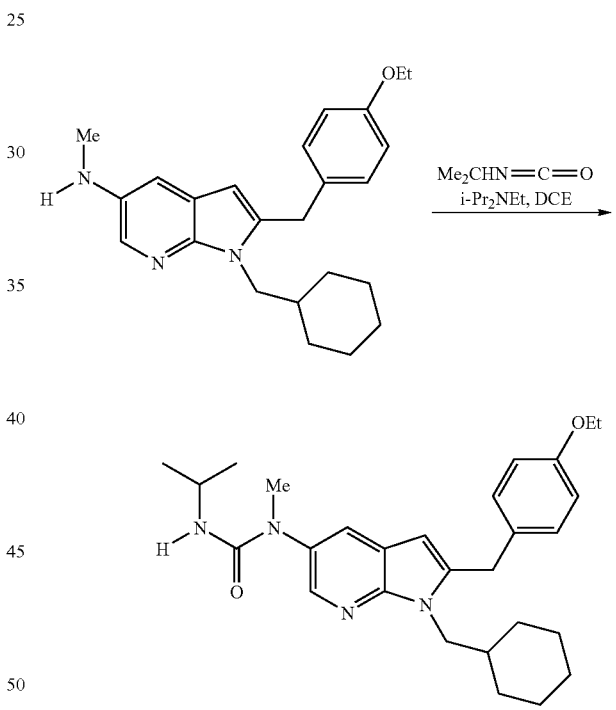

A solution of 1-(cyclohexylmethyl)-2-[(4-ethoxyphenyl)methyl]-N-methyl-1H-pyrrolo[2,3-b]pyridin-5-amine (400 mg, 1.06 mmol), isopropyl isocyanate (425 mg, 5 mmol) and iPr$_2$NEt (1.0 mL) in ClCH$_2$CH$_2$Cl (30 mL) was refluxed for 1 h, and then concentrated. The resulting residue was purified by preparative HPLC to give its TFA salt (204 mg, 33%). $^1$H-NMR (CD$_3$OD, TFA salt): δ 1.03 (d, J=6.4 Hz, 6H), 1.08 (m, 5H), 1.34 (t, J=6.8 Hz, 3H), 1.46 (m, 2H), 1.64 (m, 3H), 1.76 (m, 1H), 3.23 (s, 3H), 3.88 (m, 1H), 3.98 (q, J=7.0 Hz, 2H), 3.98 (d, J=7.6 Hz, 2H), 4.12 (s, 2H), 6.24 (s, 1H), 6.83 (d, J=8.8 Hz, 2H), 7.10 (d, J=8.8 Hz, 2H), 7.84 (d, J=2.4 Hz, 1H), 8.06 (d, J=2.4 Hz, 1H). Exact mass Calcd. For $C_{27}H_{38}N_4O_2$+1, 463.3073, found: 463.3055 (M$^+$+1).

Example 4

N-[1-(cyclohexylmethyl)-2-[(4-ethoxyphenyl)methyl]-1H-pyrrolo[2,3-b]pyridin-5-yl]-N,3-dimethylbutanamide

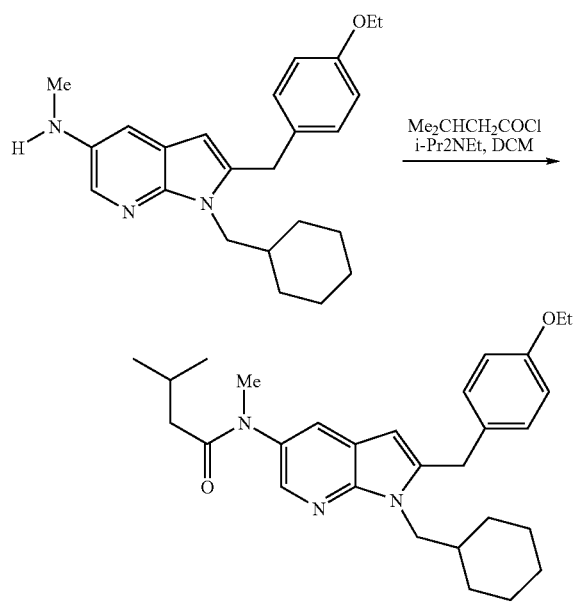

To a solution of 1-(cyclohexylmethyl)-2-[(4-ethoxyphenyl)methyl]-N-methyl-1H-pyrrolo[2,3-b]pyridin-5-amine (30 mg, 0.08 mmol) and iPr$_2$NEt (0.5 mL) in CH$_2$Cl$_2$ (10 mL) was added isovaleryl chloride (24 mg, 0.2 mmol) at 0° C. The reaction mixture was stirred at room temperature overnight, and then concentrated. The resulting residue was purified by preparative HPLC to give its TFA salt (20 mg, 43%). $^1$H-NMR (CD$_3$OD, TFA salt): δ 0.78 (d, J=6.8 Hz, 6H), 1.07 (m, 5H), 1.34 (t, J=6.8 Hz, 3H), 1.46 (m, 2H), 1.62 (m, 3H), 1.78 (m, 1H), 1.94 (d, J=6.8 Hz, 2H), 2.00 (m, 1H), 3.26 (s, 3H), 3.98 (q, J=7.0 Hz, 2H), 4.00 (d, J=7.6 Hz, 2H), 4.12 (s, 2H), 6.21 (s, 1H), 6.83 (d, J=8.8 Hz, 2H), 7.11 (d, J=8.8 Hz, 2H), 7.775 (d, J=2.4 Hz, 1H), 8.03 (d, J=2.4 Hz, 1H). MS (ESI) (M+H)$^+$462.07(MH+).

Example 5

N-[1-(cyclohexylmethyl)-2-[(4-ethoxyphenyl)methyl]-1H-pyrrolo[2,3-b]pyridin-5-yl]-N,2-dimethylpropanamide

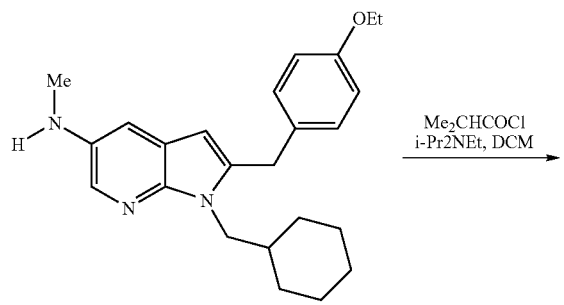

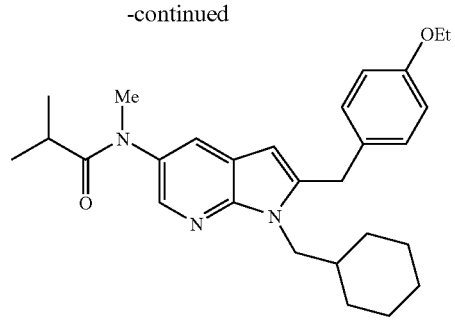

Following the procedure in Example 4, using isobutyryl chloride (21 mg, 0.2 mmol) and 1-(cyclohexylmethyl)-2-[(4-ethoxyphenyl)methyl]-N-methyl-1H-pyrrolo[2,3-b]pyridin-5-amine (30 mg, 0.08 mmol), provided the desired compound as its TFA salt (22 mg, 49%). $^1$H-NMR (CD$_3$OD, TFA salt): δ 0.98 (d, J=6.8 Hz, 6H), 1.10 (m, 5H), 1.35 (t, J=6.8 Hz, 3H), 1.48 (m, 2H), 1.64 (m, 3H), 1.78 (m, 1H), 2.46 (m, 1H), 3.26 (s, 3H), 3.99 (q, J=7.0 Hz, 2H), 4.00 (d, J=7.6 Hz, 2H), 4.13 (s, 2H), 6.24 (s, 1H), 6.84 (d, J=8.8 Hz, 2H), 7.11 (d, J=8.8 Hz, 2H), 7.85 (d, J=2.4 Hz, 1H), 8.09 (d, J=2.4 Hz, 1H). Exact mass Calcd. For C$_{27}$H$_{37}$N$_3$O$_2$+1, 448.2964, found: 448.3062 (M$^+$+1).

Example 6

N-[1-(cyclohexylmethyl)-2-[(4-ethoxyphenyl)methyl]-1H-pyrrolo[2,3-b]pyridin-5-yl]-N-methyl-cyclopropanecarboxamide

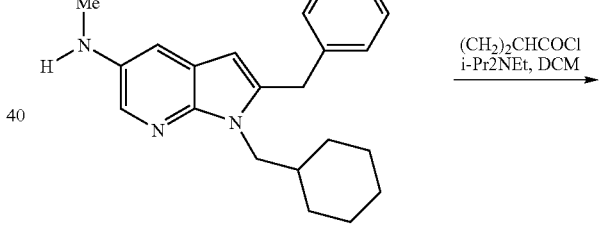

Following the procedure in Example 4, using cyclopropanecarbonyl chloride (21 mg, 0.2 mmol) and 1-(cyclohexylmethyl)-2-[(4-ethoxyphenyl)methyl]-N-methyl-1H-pyrrolo[2,3-b]pyridin-5-amine (30 mg, 0.08 mmol), provided the desired compound as its TFA salt (24 mg, 54%). $^1$H-NMR (CD$_3$OD, TFA salt): δ 0.63 (m, 2H), 0.90 (m, 2H), 1.08 (m, 6H), 1.35 (t, J=6.8 Hz, 3H), 1.48 (m, 2H), 1.64 (m, 3H), 1.78 (m, 1H), 3.29 (s, 3H), 3.99 (q, J=7.0 Hz, 2H), 4.00 (d, J=7.6 Hz, 2H), 4.11 (s, 2H), 6.24 (s, 1H), 6.84 (d, J=8.8 Hz, 2H), 7.11 (d, J=8.8 Hz, 2H), 7.90 (d, J=2.4 Hz, 1H), 8.15 (d, J=2.4 Hz, 1H). Exact mass Calcd. For C$_{27}$H$_{35}$N$_3$O$_2$+1, 446.2808, found: 446.2904 (M$^+$+1).

Example 7

N-[1-(cyclohexylmethyl)-2-[(4-ethoxyphenyl)methyl]-1H-pyrrolo[2,3-b]pyridin-5-yl]-N,2,2-trimethyl-propanamide

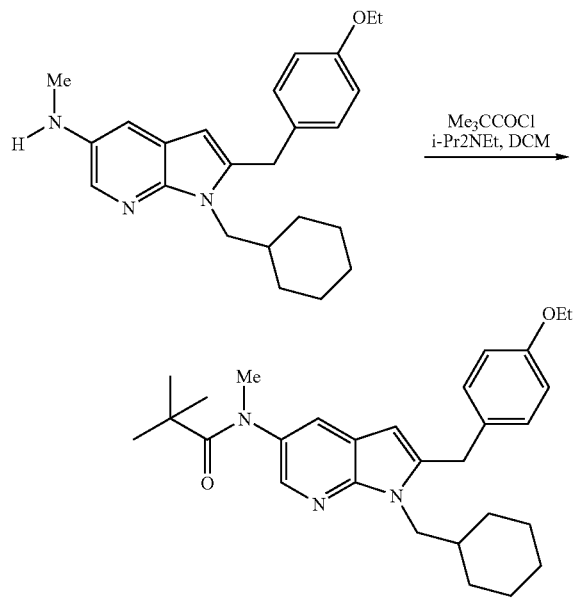

Following the procedure in Example 4, using trimethylacetyl chloride (24 mg, 0.2 mmol) and 1-(cyclohexylmethyl)-2-[(4-ethoxyphenyl)methyl]-N-methyl-1H-pyrrolo[2,3-b]pyridin-5-amine (30 mg, 0.08 mmol), provided the desired compound as its TFA salt (25 mg, 54%). $^1$H-NMR (CD$_3$OD, TFA salt): δ 1.04 (s, 9H), 1.08 (m, 5H), 1.35 (t, J=7.0 Hz, 3H), 1.44 (m, 2H), 1.63 (m, 3H), 1.76 (m, 1H), 3.27 (s, 3H), 3.99 (q, J=7.0 Hz, 2H), 4.02 (d, J=7.6 Hz, 2H), 4.13 (s, 2H), 6.25 (s, 1H), 6.85 (d, J=8.8 Hz, 2H), 7.13 (d, J=8.8 Hz, 2H), 7.89 (d, J=2.4 Hz, 1H), 8.11 (d, J=2.4 Hz, 1H). Exact mass Calcd. For C$_{24}$H$_{39}$N$_3$O$_2$+1, 462.3121, found: 462.3208 (M$^+$+1).

Example 8

N-[1-(cyclohexylmethyl)-2-[(4-ethoxyphenyl)methyl]-1H-pyrrolo[2,3-b]pyridin-5-yl]-N',N'-diethyl-N-methyl-urea

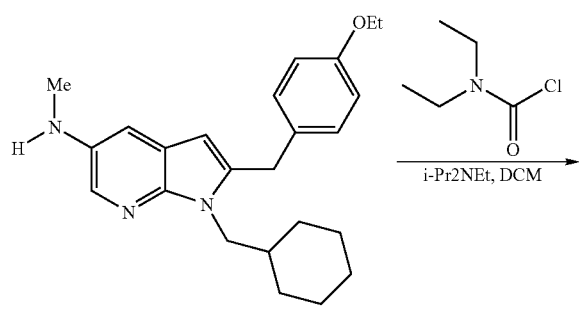

-continued

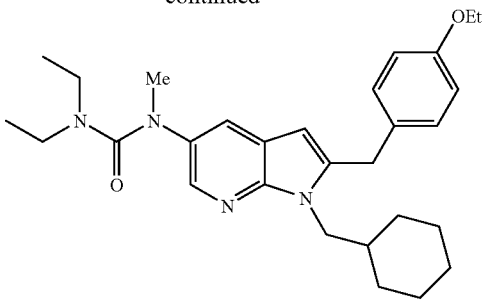

Following the procedure in Example 4, using diethylcarbamyl chloride (27 mg, 0.2 mmol) and 1-(cyclohexylmethyl)-2-[(4-ethoxyphenyl)methyl]-N-methyl-1H-pyrrolo[2,3-b]pyridin-5-amine (30 mg, 0.08 mmol), provided the desired compound as its TFA salt (28 mg, 59%). $^1$H-NMR (CD$_3$OD, TFA salt): δ 0.83 (t, J=7.0 Hz, 6H), 1.09 (m, 5H), 1.35 (t, J=7.0 Hz, 3H), 1.42 (m, 2H), 1.62 (m, 3H), 1.75 (m, 1H), 3.15 (q, J=7.0 Hz, 4H), 3.15 (s, 3H), 3.99 (q, J=7.0 Hz, 2H), 4.00 (d, J=7.6 Hz, 2H), 4.11 (s, 2H), 6.22 (s, 1H), 6.84 (d, J=8.8 Hz, 2H), 7.11 (d, J=8.8 Hz, 2H), 7.82 (d, J=2.4 Hz, 1H), 8.00 (d, J=2.4 Hz, 1H). MS (ESI) (M+H)$^+$477.2

Example 9

N-[1-(cyclohexylmethyl)-2-[(4-ethoxyphenyl)methyl]-1H-pyrrolo[2,3-b]pyridin-5-yl]-N,5-dimethyl-3-isoxazolecarboxamide

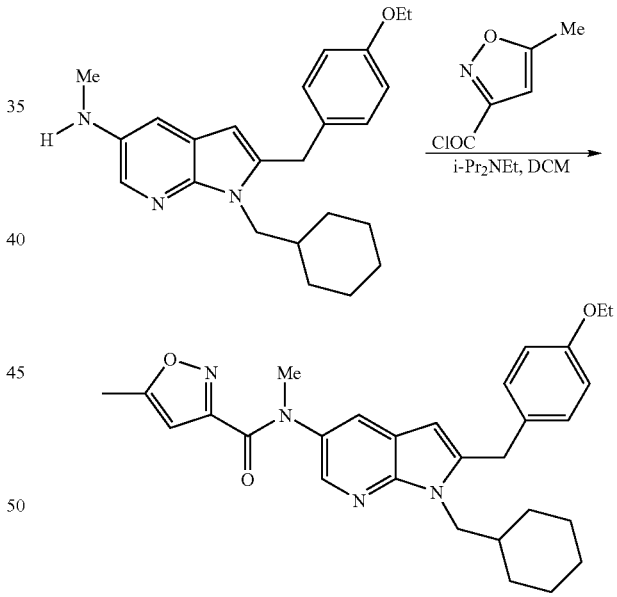

Following the procedure in Example 4, using 5-methyl-3-isoxazolecarbonyl chloride (50 mg, 0.33 mmol) and 1-(cyclohexylmethyl)-2-[(4-ethoxyphenyl)methyl]-N-methyl-1H-pyrrolo[2,3-b]pyridin-5-amine (60 mg, 0.16 mmol), provided the desired compound as its TFA salt (20 mg, 21%). $^1$H-NMR (CD$_3$OD, TFA salt): δ 1.03 (m, 5H), 1.33 (t, J=6.8 Hz, 3H), 1.38 (m, 2H), 1.62 (m, 4H), 2.20 (s, 3H), 3.45 (s, 3H), 3.94 (q, J=7.0 Hz, 2H), 3.97 (d, J=7.6 Hz, 2H), 4.07 (s, 2H), 5.93 (s, 1H), 6.12 (s, 1H), 6.82 (d, J=8.4 Hz, 2H), 7.09 (d, J=8.4 Hz, 2H), 7.75 (d, J=2.0 Hz, 1H), 7.95 (d, J=2.0 Hz, 1H). Anal. Calcd. for C$_{29}$H$_{34}$N$_4$O$_3$+0.50 TFA: C, 66.28; H, 6.40; N, 10.31. Found: C, 66.24; H, 6.34; N, 10.22; Exact mass Calcd. For C$_{29}$H$_{34}$N$_4$O$_3$+1, 487.2709, found: 487.2712 (M$^+$+1).

Example 10

N-[1-(cyclohexylmethyl)-2-[(4-ethoxyphenyl)methyl]-1H-pyrrolo[2,3-b]pyridin-5-yl]-2-fluoro-N-methyl-benzamide

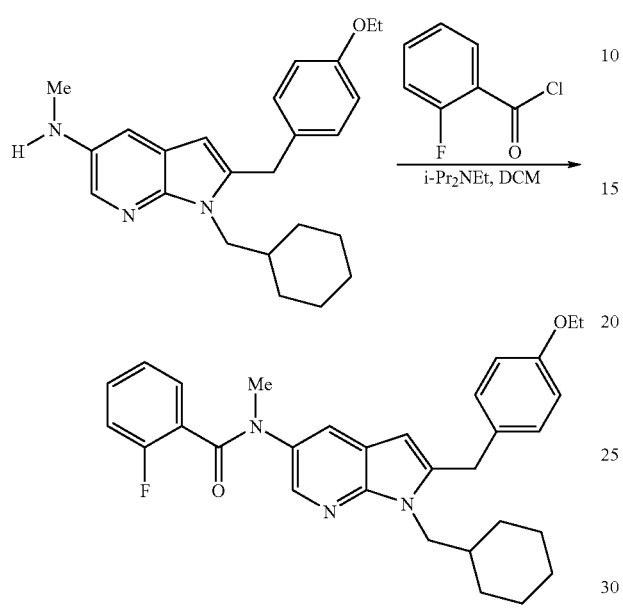

Following the procedure in Example 4, using 2-fluorobenzoyl chloride (50 mg, 0.31 mmol) and 1-(cyclohexylmethyl)-2-[(4-ethoxyphenyl)methyl]-N-methyl-1H-pyrrolo[2,3-b]pyridin-5-amine (60 mg, 0.16 mmol), provided the desired compound as its TFA salt (30 mg, 31%). $^1$H-NMR (CD$_3$OD, TFA salt): δ 0.88 ((m, 2H), 1.04 (m, 3H), 1.30 (m, 2H), 1.34 (t, J=6.8 Hz, 3H), 1.60 (m, 4H), 3.48 (s, 3H), 3.87 (d, J=8.0 Hz, 2H), 3.97 (q, J=7.2 Hz, 2H), 4.03 (s, 2H), 6.04 (s, 1H), 6.82 (m, 3H), 6.99 (m, 1H), 7.06 (d, J=8.4 Hz, 2H), 7.18 (m, 1H), 7.26 (m, 1H), 7.70 (d, J=1.2 Hz, 1H), 7.86 (d, J=1.2 Hz, 1H). Anal. Calcd. for C$_{31}$H$_{34}$FN$_3$O$_2$+0.10 TFA: C, 73.33; H, 6.73; N, 8.22. Found: C, 72.93; H, 6.71; N, 8.19; Exact mass Calcd. For C$_{31}$H$_{34}$FN$_3$O$_2$+1, 500.2713, found: 500.2757 (M$^+$+1).

Example 11

N-[1-(cyclohexylmethyl)-2-[(5-ethoxy-2-pyridinyl)methyl]-1H-pyrrolo[2,3-b]pyridin-5-yl]-2,2-dimethyl-propanamide

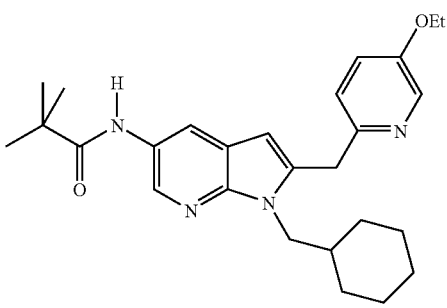

Step A. 2-[(cyclohexylmethyl)amino]-5-[(2,2-dimethyl-1-oxopronyl)amino]-3-pyridineacetic acid:

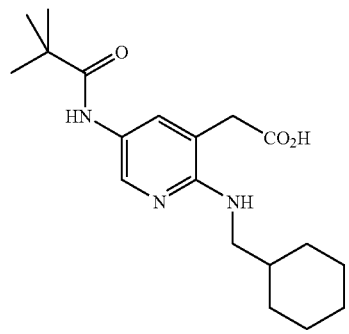

To a solution of N-[6-[(cyclohexylmethyl)amino]-5-methyl-3-pyridinyl]-2,2-dimethyl-propanamide (303 mg, 1.0 mmol) in dry THF (20 mL) was added t-butyllithium (3.0 mL, 1.7 M, 5.1 mmol) at −50° C. After warming up to −10° C., CO$_2$ was introduced into the reaction mixture. After 10 min, the reaction mixture was quenched with aqueous NH$_4$Cl solution, and extracted with ethyl acetate (2×100 mL). The combined organic layers were washed with brine and dried over MgSO$_4$. Removal of solvents gave a product, which was consistent with the MS of the desired compound. The product was subject to the next step directly without purification.

Step B. Methyl-2-[(cyclohexylmethyl)amino]-5-[(2,2-dimethyl-1-oxopropyl)amino]-3-pyridineacetate:

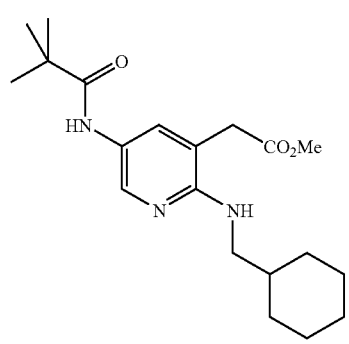

To a solution of the product 2-[(cyclohexylmethyl)amino]-5-[(2,2-dimethyl-1-oxopropyl)amino]-3-pyridineacetic acid in dry MeOH (7.5 mL) was added 4N HCl solution (in dioxane, 2.5 mL) at 0° C. The reaction mixture was stirred overnight at r.t, and then condensed under vacuum, diluted with AcOEt (50 mL), washed with 1N NH$_4$OH (100 mL), brine (50 mL), and dried over MgSO$_4$. Removal of solvent afforded desired title product (325 mg, 90%). $^1$H-NMR (CDCl$_3$): δ 0.98 (m, 2H), 1.19 (m, 3H), 1.24 (s, 9H), 1.58 (m, 1H), 1.67 (m, 3H), 1.76 (m, 2H), 3.20 (d, J=6.8 Hz, 2H), 3.39 (s, 2H), 3.63 (s, 3H), 4.98 (brs, 1H), 7.24 (brs, 1H), 7.680 (s, 1H), 7.92 (s, 1H).

Step C. N-[1-(cyclohexylmethyl)-2-[(5-ethoxy-2-pyridinyl)methyl]-1H-pyrrolo[2,3-b]pyridin-5-yl]-2,2-dimethyl-propanamide

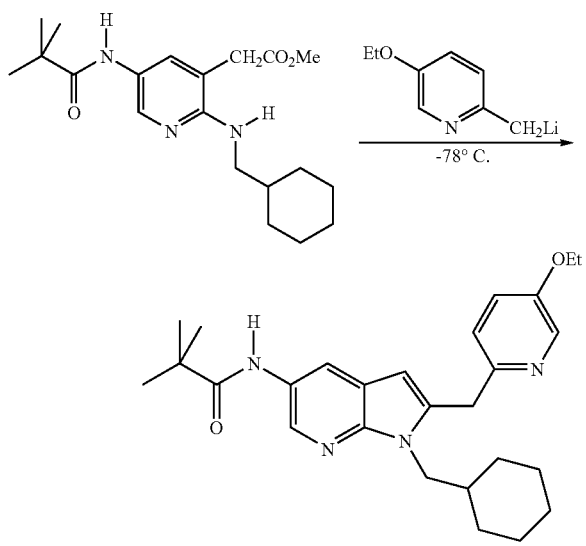

Intermediate 1

To a solution of 5-ethoxy-2-methyl-pyridine (274 mg, 2.0 mmol) in dry THF was added a solution of t-BuLi (1.7 M, 1.2 mL, 2.04 mmol) at −78° C. After stirring for about 3 min., a solution of Intermediate 1 (180 mg, 0.5 mmol) in 1.5 mL THF was added into the reaction mixture at −78° C. The resulting mixture was stirred for an additional 30 min, and then quenched with aqueous NH$_4$Cl solution, and extracted with ethyl acetate (2×50 mL). The combined organic layers were washed with brine and dried over MgSO$_4$. Removal of solvents gave a product, which was purified by Gilson to give the desired product as its TFA salts (95 mg, 28%): $^1$H-NMR (CD3OD, TFA salt): δ 1.12 (m, 5H), 1.31 (s, 9H), 1.48 (t, J=7.2 Hz, 3H), 1.52 (m, 2H), 1.70 (m, 3H), 1.82 (m, 1H), 4.08 (d, J=7.6 Hz, 2H), 4.25 (q, J=6.8 Hz, 2H), 4.53 (s, 2H), 6.13 (s, 1H), 7.72 (d, J=8.8 Hz, 1H), 7.99 (dd, J=8.8, 2.8 Hz, 1H), 8.08 (d, J=2.4 Hz, 1H), 8.30 (d, J=2.4 Hz, 1H), 8.45 (d, J=2.8 Hz, 1H). MS (ESI) (M+H)$^+$ 449.2

Example 12

[1-(cyclohexylmethyl)-2-[(5-ethoxy-2-pyridinyl)methyl]-1H-pyrrolo[2,3-b]pyridin-5-yl]-, 1-methylethyl ester carbamic acid

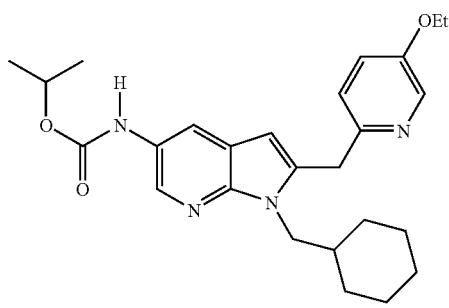

Step A. 1-Methylethyl [6-[(cyclohexylmethyl)amino]-5-methyl-3-pyridinyl]-carbamic acid ester

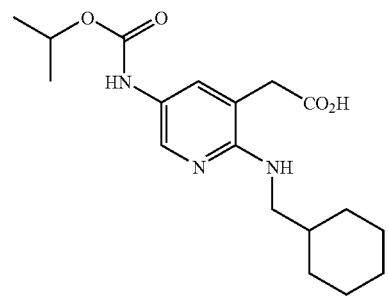

Following the same method as described for preparing the compound in Example 1 step C, using 2.75 g (12.6 mmol) of N$^2$-(cyclohexyl methyl)-3-methyl-2,5-pyridinediamine and isopropyl chloroformate (1 M in toluene, 13 ml, 13 mmol), provided the title compound (3.87 g, 100%). 1H-NMR (CD$_3$OD): δ 1.00 (m, 2H), 1.20 (m, 3H), 1.26 (d, J=6.4 Hz, 6H), 1.58 (m, 1H), 1.72 (m, 3H), 1.80 (m, 2H), 2.06 (s, 3H), 3.24 (d, J=6.8 Hz, 2H), 4.98 (m, 1H), 6.29 (brs, 1H), 7.50 (s, 1H), 7.83 (s, 1H). MS (ESI) (M+H)$^+$: 305.30.

Step B. 2-[(cyclohexylmethyl)amino]-5-[[(1-methyletboxy)carbonyl]amino]-3-pyridineacetic acid methyl ester

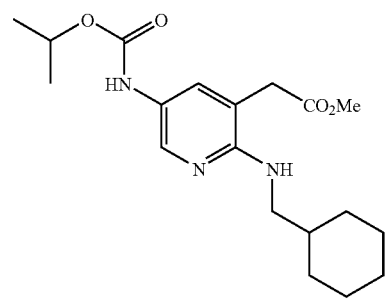

Following the same method as described for the synthesis of the compound in Example 11, step A, using starting material 1-methylethyl [6-[(cyclohexylmethyl)amino]-5-methyl-3-pyridinyl]-carbamic acid ester (1.22 g, 4.0 mmol, in dry THF 960 mL)) and t-butyllithium (9.5 mL, 1.7 M, 16.0 mmol), provided the title compound.

Step C. 2-[(cyclohexylmethyl)amino]-5-[[(1-methylethoxy)carbonyl]amino]-3-pridineacetic acid methyl ester Following the same method as described for preparing methyl-2-[(cyclohexylmethyl)amino]-5-[(2,2-dimethyl-1-oxopropyl)amino]-3-pyridineacetate (Example 11, Step B). Using the product from the last step as the starting material, provided a product, which was purified by Gilson followed by work up to give the product (765 mg, 53%). $^1$H-NMR (CD$_3$OD): δ 1.00 (m, 2H), 1.20 (m, 3H), 1.26 (d, J=6.4 Hz, 6H), 1.58 (m, 1H), 1.72 (m, 3H), 1.80 (m, 2H), 3.24 (d, J=6.8

Hz, 2H), 3.44 (s, 2H), 3.67 (s, 3H), 4.05 (brs, 1H), 4.98 (m, 1H), 6.32 (brs, 1H), 7.60 (s, 1H), 7.90 (s, 1H).

Step D. [1-(cyclohexylmethyl)-2-[(5-ethoxy-2-pyridinyl)methyl]-1H-pyrrolo[2,3-b]pyridin-5-yl]-, 1-methylethyl ester carbamic acid

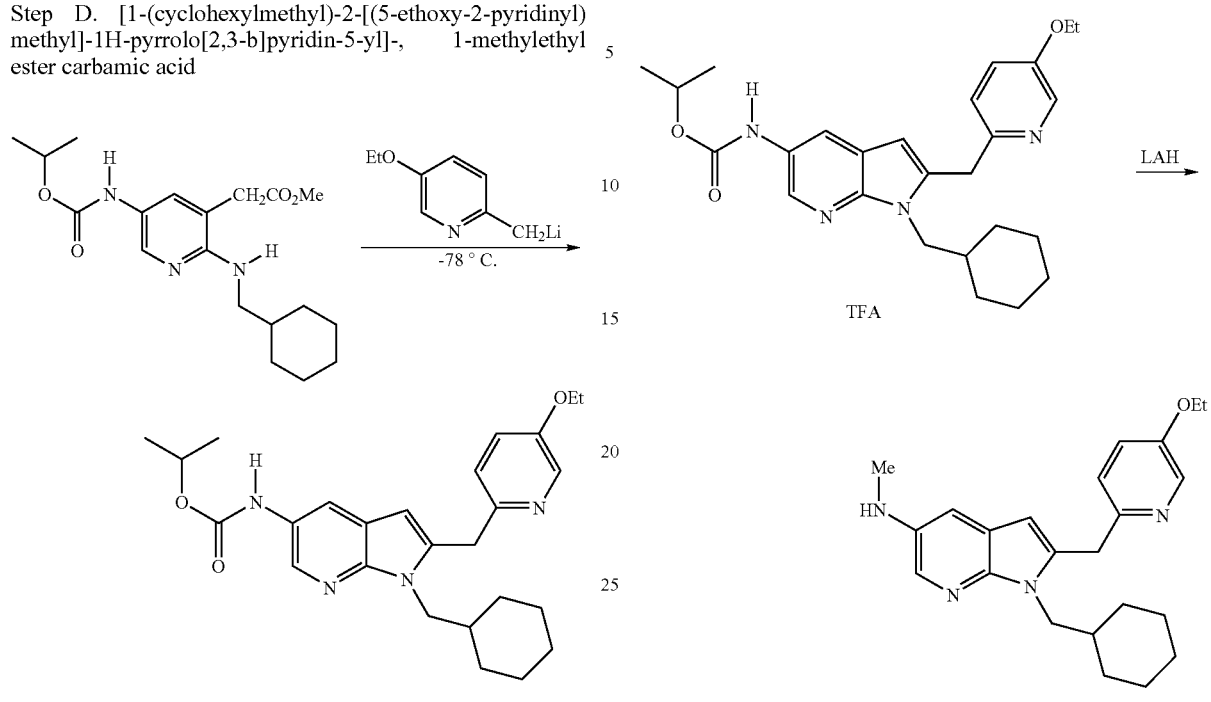

Method as described for N-[1-(cyclohexylmethyl)-2-[(5-ethoxy-2-pyridinyl)methyl]-1H-pyrrolo[2,3-b]pyridin-5-yl]-2,2-dimethyl-propanamide (Example 11, Step C), but using 5-ethoxy-2-methyl-pyridine (1.37 g, 10.0 mmol) and 2-[(cyclohexylmethyl)amino]-5-[[(1-methylethoxy)carbonyl]amino]-3-pridineacetic acid methyl ester (726 mg, 2.0 mmol), provided the title compound as its TFA salt (546 mg, 40%). $^1$H-NMR (CD$_3$OD, TFA salt): δ 1.11 (m, 5H), 1.29 (d, J=6.0 Hz, 6H), 1.46 (t, J=7.00 Hz, 3H), 1.50 (m, 2H), 1.72 (m, 3H), 1.81 (m, 1H), 4.08 (d, J=8.0 Hz, 2H), 4.25 (q, J=6.8 Hz, 2H), 4.55 (s, 2H), 4.93 (m, 1H), 6.13 (s, 1H), 7.74 (d, J=8.8 Hz, 1H), 8.02 (dd, J=8.8, 2.8 Hz, 1H), 8.09 (s, 1H), 8.26 (s, 1H), 8.47 (d, J=2.8 Hz, 1H). MS (ESI) (M+H)$^+$451.2.

Example 13

N-[1-(cyclohexylmethyl)-2-[(5-ethoxy-2-pyridinyl)methyl]-1H-pyrrolo[2,3-b]pyridin-5-yl]-N,2,2-trimethyl-propanamide To a solution of [1-(cyclohexylmethyl)-2-[(5-ethoxy-2-pyridinyl)methyl]-1H-pyrrolo[2,3-b]pyridin-5-yl]-, 1-methylethyl ester carbamic acid (520 mg, 0.77 mmol) in THF was added LiAlH$_4$ (1.44 g) at −20 ° C. The reaction mixture was stirred at room temperature overnight, and quenched carefully at −20° C. by adding MeOH (5 mL) and H$_2$O (3 mL), diluted with Et$_2$O (50 mL), and then added Na$_2$SO$_4$ (10 g). The resulting mixture was stirred for 2 hr at r.t. After filtration, the organic solution was concentrated in vacuo to afford a product (263 mg, 90%), which was used in the next steps without further purification. $^1$H-NMR (CDCl3): δ 1.08 (m, 5H), 1.35 (t, J=7.2 Hz, 3H), 1.42 (m, 2H), 1.62 (m, 3H), 1.75 (m, 1H), 3.15 (s, 3H), 3.99 (q, J=7.2 Hz, 2H), 4.00 (d, J=7.2 Hz, 2H), 4.11 (s, 2H), 6.22 (s, 1H), 6.84 (d, J=8.4 Hz, 1H), 7.11 (d, J=8.4 Hz, 1H), 7.60 (brs, 1H), 7.82 (s, 1H), 8.00 (s, 1H). MS (ESI) (M+H)$^+$379.94.

Step B. N-[1-(cyclohexylmethyl)-2-[(5-ethoxy-2-pyridinyl)methyl]-1H-pyrrolo[2,3-b]pyridin-5-yl]-N,2,2-trimethyl-propanamide

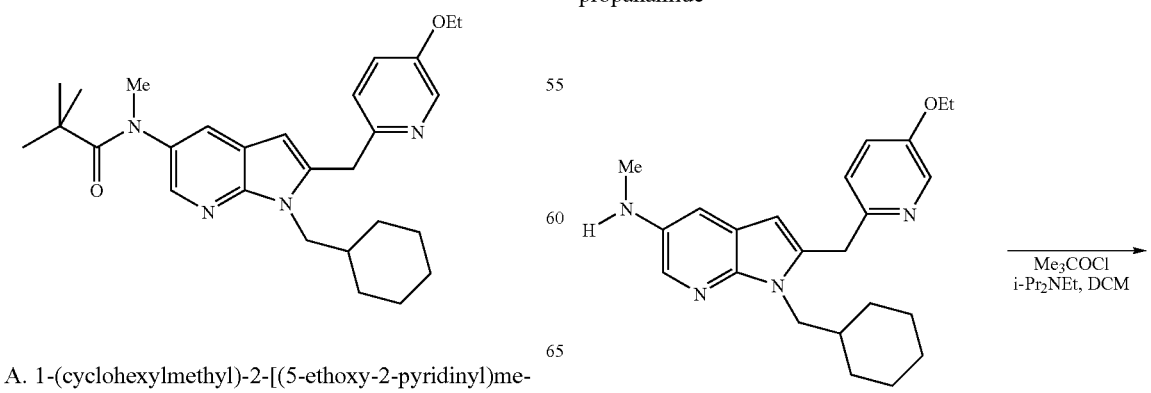

Step A. 1-(cyclohexylmethyl)-2-[(5-ethoxy-2-pyridinyl)methyl]-N-methyl-1H-pyrrolo[2,3-b]pyridin-5-amine

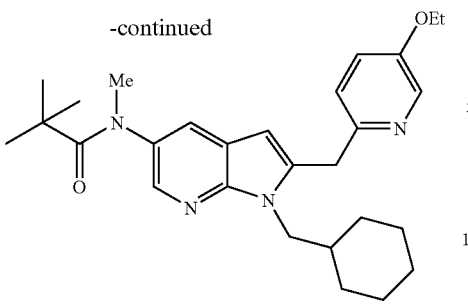

Following the procedure in Example 7, using 1-(cyclohexylmethyl)-2-[(5-ethoxy-2-pyridinyl)methyl]-N-methyl-1H-pyrrolo[2,3-b]pyridin-5-amine (30 mg, 0.08 mmol) and trimethylacetyl chloride (24 mg, 0.2 mmol), provided the desired compound as its TFA salt (15 mg, 27%). $^1$H-NMR (CD$_3$OD, TFA salt): δ 1.01 (s, 9H), 1.12 (m, 5H), 1.46 (t, J=7.2 Hz, 3H), 1.50 (m, 2H), 1.72 (m, 3H), 1.84 (m, 1H), 3.25 (s, 3H), 4.13 (d, J=7.2 Hz, 2H), 4.25 (q, J=7.2 Hz, 2H), 4.55 (s, 2H), 6.16 (s, 1H), 7.72 (d, J=8.8 Hz, 1H), 7.82 (d, J=2.4 Hz, 1H), 7.97 (dd, J=8.8, 2.8 Hz, 1H), 8.14 (d, J=2.4 Hz, 1H). 8.45 (d, J=2.8 Hz, 1H). MS (ESI) (M+H)$^+$463.2

Example 14

N-[1-(cyclohexylmethyl)-2-[(5-ethoxy-2-pyridinyl)methyl]-1H-pyrrolo[2,3-b]pyridin-5-yl]-N,3-dimethyl-butanamide

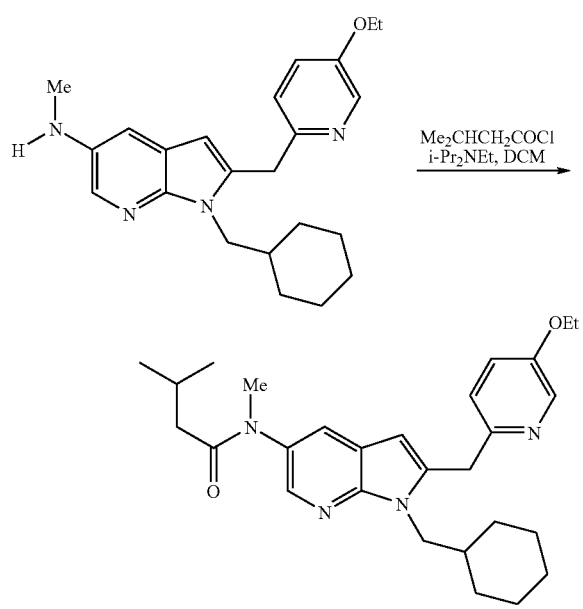

Following the procedure in Example 4, using 1-(cyclohexylmethyl)-2-[(5-ethoxy-2-pyridinyl)methyl]-N-methyl-1H-pyrrolo[2,3-b]pyridin-5-amine (30 mg, 0.08 mmol) and isobutyryl chloride (24 mg, 0.2 mmol), provided the desired compound as its TFA salt (12 mg, 22%). $^1$H-NMR (CD$_3$OD, TFA salt): δ 0.79 (d, J=6.4 Hz, 6H), 1.12 (m, 5H), 1.46 (t, J=7.2 Hz, 3H), 1.54 (m, 2H), 1.68 (m, 3H), 1.84 (m, 1H), 1.93 (d, J=6.8 Hz, 2H), 2.01 (m, 1H), 3.28 (s, 3H), 4.13 (d, J=7.6 Hz, 2H), 4.25 (q, J=6.8 Hz, 2H), 4.56 (s, 2H), 6.18 (s, 1H), 7.72 (d, J=9.2 Hz, 1H), 7.80 (d, J=2.4 Hz, 1H), 7.98 (dd, J=9.2, 2.8 Hz, 1H), 8.12 (d, J=2.4 Hz, 1H). 8.46 (d, J=2.8 Hz, 1H). MS (ESI) (M+H)$^+$463.2

Example 15

N-[1-(cyclohexylmethyl)-2-[(5-ethoxy-2-pyridinyl)methyl]-1H-pyrrolo[2,3-b]pyridin-5-yl]-N-methyl-N'-(1-methylethyl)-urea

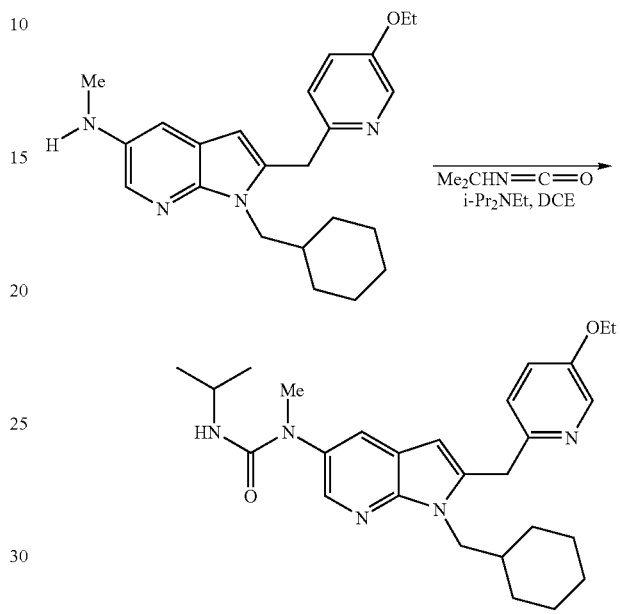

Following the procedure B in Example 3, using 1-(cyclohexylmethyl)-2-[(5-ethoxy-2-pyridinyl)methyl]-N-methyl-1H-pyrrolo[2,3-b]pyridin-5-amine (30 mg, 0.08 mmol) and isopropyl isocyanate (43 mg, 0.5 mmol), provided the desired compound as its TFA salt (20 mg, 36%). $^1$H-NMR (CD$_3$OD, TFA salt): δ 1.06 (d, J=6.4 Hz, 6H), 1.12 (m, 5H), 1.46 (t, J=7.2 Hz, 3H), 1.54 (m, 2H), 1.68 (m, 3H), 1.84 (m, 1H), 3.25 (s, 3H), 3.88 (m, 1H), 4.11 (d, J=7.6 Hz, 2H), 4.25 (q, J=7.2 Hz, 2H), 4.58 (s, 2H), 6.18 (s, 1H), 7.75 (d, J=8.8 Hz, 1H), 7.83 (d, J=2.4 Hz, 1H), 8.04 (dd, J=8.8, 2.8 Hz, 1H), 8.14 (d, J=2.4 Hz, 1H). 8.49 (d, J=2.8 Hz, 1H).

Example 16

N-[2-[(4-ethoxyphenyl)methyl]-1-[(tetrahydro-2H-pyran-4-yl)methyl]-1H-pyrrolo[2,3-b]pyridin-5-yl]-2,2-dimethyl-propanamide

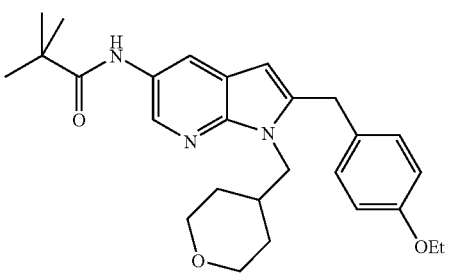

Step A. 2,2-dimethyl-N-[5-methyl-6-[[(tetrahydro-2H-pyran-4-yl)methyl]amino]-3-pyridinyl]-propanamide

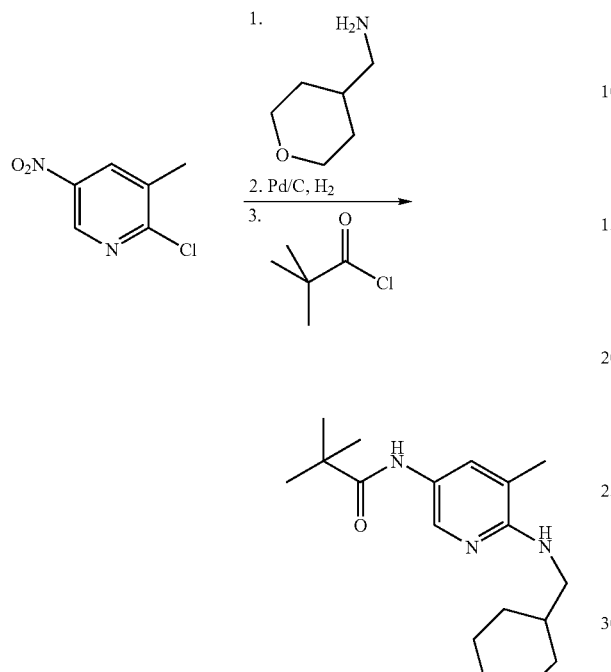

To a solution of 2-chloro-3-methyl-5-nitropyridine (5.0 g, 29.0 mmol) in ethanol (100 ml) at room temperature was added triethylamine (8.0 ml, 58.0 mmol) followed by 4-aminomethyl tetrahydropyran (3.7 g, 31.9 mmol). The reaction mixture was refluxed overnight. Subsequently, the mixture was cooled to room temperature and concentrated in vacuo.

The residue was taken up into ethyl acetate (75 ml) and palladium on carbon (120 mgs, 10% grade, 0.1 mmol) was added. The suspension was placed in Parr apparatus and shaken for 72 hours under a hydrogen atmosphere (35 psi). The suspension was then brought to normal atmosphere and filtered on Diatomaceous earth. The filtrate was concentrated in vacuo.

This residue was taken up into dichloromethane (125 ml) at −78° C. to which was added diisopropyl ethylamine (6.1 ml, 34.8 mmol) followed by pivaloyl chloride (3.73 ml, 30.3 mmol). The mixture was stirred for two hours at 0° C. and then quenched with 2M NaOH aqueous solution (50 ml). The phases were separated and the aqueous phase was back-extracted with additional dichloromethane (125 ml). The organic phases were combined, dried with MgSO$_4$, filtered and concentrated in vacuo. The residue was purified using silica gel flash chromatography ([3% MeOH+0.5% NH$_4$OHaq] in CH$_2$Cl$_2$) to provide 8.1 g of the title compound 2,2-dimethyl-N-[5-methyl-6-[[(tetrahydro-2H-pyran-4-yl)methyl]amino]-3-pyridinyl]-propanamide. 1H NMR (400 MHz, CHLOROFORM-D) δ ppm 1.29 (s, 9 H) 1.36 (m, 2 H) 1.67 (m, 2 H) 1.88 (m, 1 H) 2.04 (d, J=10.55 Hz, 3 H) 3.36 (m, 4 H) 3.97 (m, 2 H) 4.12 (m, 1 H) 7.12 (s, 1 H) 7.63 (d, J=1.76 Hz, 1 H) 7.86 (d, J=2.73 Hz, 1 H). MS (ESI) (M+H)$^+$: 306.

Step B. N-[2-[(4-ethoxyphenyl)methyl]-1-[(tetrahydro-2H-pyran-4-yl)methyl]-1H-pyrrolo[2,3-b]pyridin-5-yl]-2,2-dimethyl-propanamide

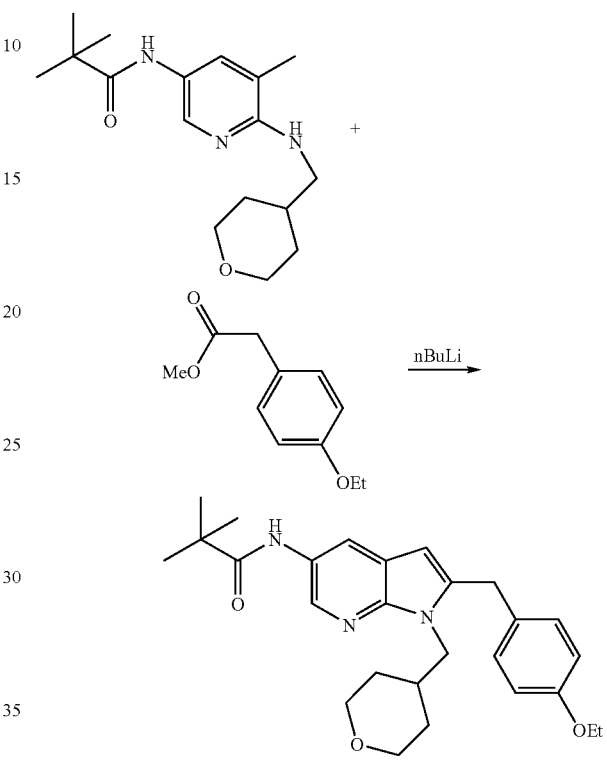

To a solution of 2,2-dimethyl-N-[5-methyl-6-[[(tetrahydro-2H-pyran-4-yl)methyl]amino]-3-pyridinyl]-propanamide (2.0 g, 6.55 mmol) in THF (70 ml) at −78° C. was added n-butyl lithium (11.5 ml of 2.0 M solution in cyclohexane, 23.0 mmol). The mixture was stirred for one hour at −20° C. and then cooled to −78° C. To this reaction mixture was cannulated a solution of methyl 4-ethoxy-benzeneacetate (1.72 g, 7.88 mmol) in THF (50 ml) at −78° C. After stirring for 3 hours at room temperature, the mixture was quenched with NaHCO$_3$ saturated aqueous solution (200 ml) and diluted with EtOAc (100 ml). The phases were separated and the aqueous phase was back-extracted with additional EtOAc (100 ml). The organic phases were combined, dried with MgSO$_4$, filtered and concentrated in vacuo. The residue was purified using silica gel flash chromatography ([3% MeOH+0.5% NH$_4$OHaq] in CH$_2$Cl$_2$) to provide 750 mg of the title compound N-[2-[(4-ethoxyphenyl)methyl]-1-[(tetrahydro-2H-pyran-4-yl)methyl]-1H-pyrrolo[2,3-b]pyridin-5-yl]-2,2-dimethyl-propanamide. 1H NMR (400 MHz, CHLOROFORM-D) δ ppm 1.31 (m, 2 H) 1.34 (s, 9 H) 1.40 (t, J=7.03 Hz, 3 H) 1.56 (m, 2 H) 2.04 (m, 1 H) 3.22 (m, 2 H) 3.35 (m, 2 H) 3.90 (t, J=3.32 Hz, 2 H) 4.00 (m, 2 H) 4.06 (s, 2 H) 6.12 (s, 1 H) 6.83 (m, 2 H) 7.07 (d, J=8.79 Hz, 2 H) 7.32 (m, 1 H) 8.09 (d, J=2.34 Hz, 1 H) 8.15 (d, J=2.34 Hz, 1 H). MS (ESI) (M+H)$^+$: 451.

Example 17

N-[2-[(4-ethoxyphenyl)methyl]-1-[(tetrahydro-2H-pyran-4-yl)methyl]-1H-pyrrolo[2,3-b]pyridin-5-yl]-2,6-difluoro-N-methyl-benzenesulfonamide

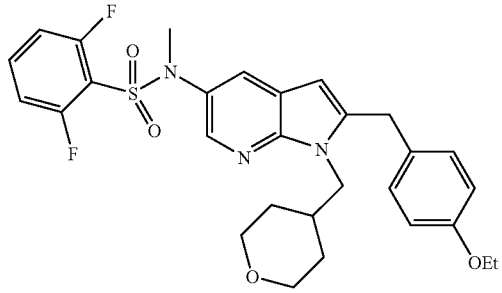

Step A. [2-[(4-ethoxyphenyl)methyl]-1-[(tetrahydro-2H-pyran-4-yl)methyl]-1H-pyrrolo[2,3-b]pyridin-5-yl]-carbamic acid methyl ester

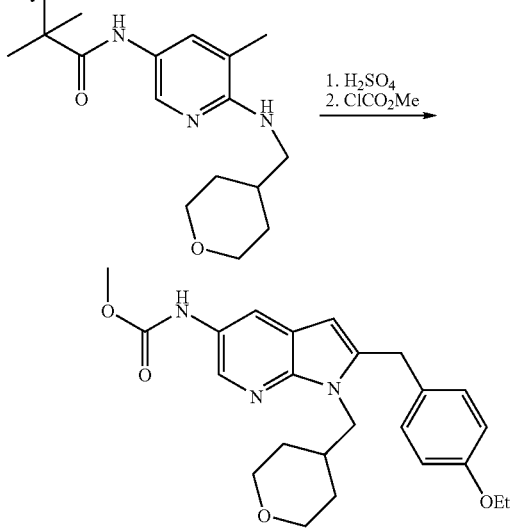

N-[2-[(4-ethoxyphenyl)methyl]-1-[(tetrahydro-2H-pyran-4-yl)methyl]-1H-pyrrolo[2,3-b]pyridin-5-yl]-2,2-dimethyl-propanamide (1.3 g, 3.0 mmol) was dissolved into a mixture of dioxane (25 mL) and 20% sulfuric acid aqueous solution (25 mL) at room temperature. The solution was brought to 120° C. After stirring for 6 hours, the mixture was cooled to room temperature and concentrated in vacuo. The residue was brought to pH 8 by addition of 2M NaOH aqueous solution (200 mL). The mixture was extracted twice with EtOAc (100 mL). The organic phases were combined, dried with MgSO$_4$, filtered and concentrated in vacuo.

The residue was taken up into dichloromethane (50 mL) and the mixture cooled to −30° C. To this solution was added diisopropyl ethylamine (1.1 mL, 6.2 mmol) followed by a solution of methylchloroformate (231 μL, 3.0 mmol) in dichloromethane (25 mL) at −78° C. The reaction was allowed to warm to 0° C. After stirring for 3 hours, the reaction was quenched with 2M Na$_2$CO$_3$ aqueous solution (50 mL). The phases were separated and the aqueous phase was back-extracted with additional dichloromethane (50 mL). The organic phases were combined, dried with MgSO$_4$, filtered and concentrated in vacuo. The residue was purified using silica gel flash chromatography ([3% MeOH+0.5% NH$_4$OHaq] in CH$_2$Cl$_2$) to provide 374 mg of the title compound [2-[(4-ethoxyphenyl)methyl]-1-[(tetrahydro-2H-pyran-4-yl)methyl]-1H-pyrrolo[2,3-b]pyridin-5-yl]-carbamic acid methyl ester. $^1$H NMR (400 MHz, CHLOROFORM-D) δ 1.29 (m, 2 H), 1.39 (t, J=6.93 Hz, 3 H), 1.56 (m, 2 H), 2.06 (m, 1 H), 3.35 (td, J=11.81, 2.15 Hz, 2 H), 3.77 (s, 3 H), 3.89 (m, 2 H), 3.95 (m, 2 H), 3.99 (m, 2 H), 4.05 (s, 2 H), 5.72 (s, 1 H), 6.09 (s, 1 H), 6.83 (m, 2 H), 7.07 (d, J=8.79 Hz, 2 H), 8.08 (d, J=2.34 Hz, 1 H), 8.14 (d, J=2.34 Hz, 1 H). MS (ESI) (M+H)$^+$: 425.

Step B. 2-[(4-ethoxyphenyl)methyl]-N-methyl-1-[(tetrahydro-2H-pyran-4-yl)methyl]-1H-pyrrolo[2,3-b]pyridin-5-amine

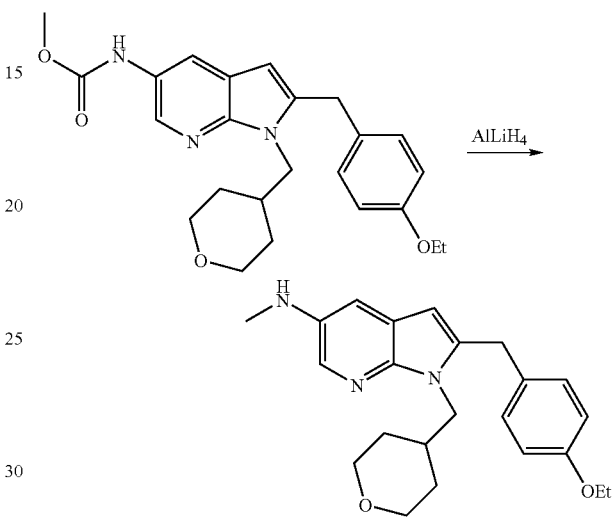

To a solution of [2-[(4-ethoxyphenyl)methyl]-1-[(tetrahydro-2H-pyran-4-yl)methyl]-1H-pyrrolo[2,3-b]pyridin-5-yl]-carbamic acid methyl ester (153 mg, 0.36 mmol) in THF (25 ml) at 0° C. was added lithium aluminum hydride (35 mg, 0.90 mmol). The mixture was stirred for 48 hours at room temperature. The reaction was then cooled to 0° C. and quenched by dropwise addition of water (35 □L), followed by 4M NaOH aqueous solution (35 μL) and water (105 μL). After stirring at room temperature for 30 minutes, the suspension was filtered over Diatomaceous earth and concentrated in vacuo to give 100 mgs of colorless oil. $^1$H NMR (400 MHz, CHLOROFORM-D) δ 1.40 (m, 5 H), 1.59 (m, 2 H), 2.05 (m, 1 H), 2.87 (s, 3 H), 3.36 (m, 2 H), 3.66 (m, 2 H), 4.01 (m, 6 H), 5.99 (s, 1 H), 6.83 (d, J=8.79 Hz, 2 H), 6.98 (s, 1 H), 7.05 (d, J=2.54 Hz, 1 H), 7.10 (d, J=8.79 Hz, 2 H), 7.79 (d, J=2.54 Hz, 1 H). MS (ESI) (M+H)$^+$: 380.

Step C. N-[2-[(4-ethoxyphenyl)methyl]-1-[(tetrahydro-2H-pyran-4-yl)methyl]-1H-pyrrolo[2,3-b]pyridin-5-yl]-2,6-difluoro-N-methyl-benzenesulfonamide

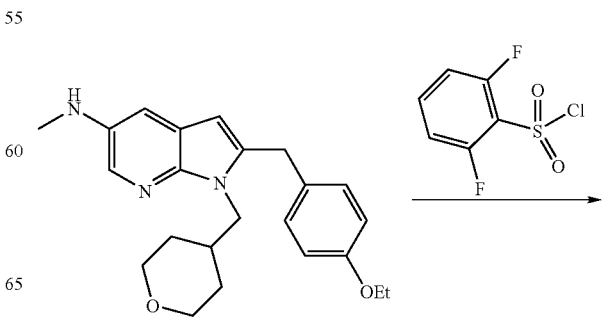

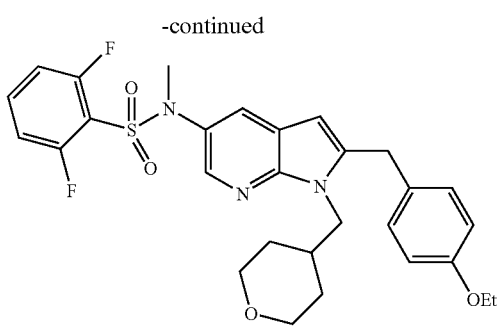

To a solution of 2-[(4-ethoxyphenyl)methyl]-N-methyl-1-[(tetrahydro-2H-pyran-4-yl)methyl]-1H-pyrrolo[2,3-b]pyridin-5-amine (51 mg, 0.13 mmol) in dichloromethane (5 mL) at 0° C. was added diisopropylethylamine (68 µL, 0.39 mmol) followed by 2,6-difluorobenzenesulfonyl chloride (57 mg, 0.27 mmol). The mixture was stirred overnight at room temperature. The reaction was then quenched by 2 M Na$_2$CO$_3$ aqueous solution (10 mL). The phases were separated and the aqueous phase was back-extracted with additional dichloromethane (10 mL). The organic phases were combined, dried with MgSO$_4$, filtered and concentrated in vacuo. The residue was purified using HPLC (10 to 70% [0.1% TFA in AcCN solution] in 0.1% TFA aqueous solution) to provide 36 mg of the TFA salt of N-[2-[(4-ethoxyphenyl)methyl]-1-[(tetrahydro-2H-pyran-4-yl)methyl]-1H-pyrrolo[2,3-b]pyridin-5-yl]-2,6-difluoro-N-methyl-benzenesulfonamide. $^1$H NMR (400 MHz, METHANOL-D$_4$) δ 1.20 (m, 4 H), 1.26 (t, J=7.03 Hz, 3 H), 1.82 (m, 1 H), 3.09 (m, 2 H), 3.31 (s, 3 H), 3.73 (m, 2 H), 3.90 (m, 2 H), 3.94 (d, J=7.81 Hz, 2 H), 4.02 (s, 2 H), 6.04 (s, 1 H), 6.75 (d, J=8.79 Hz, 2 H), 7.01 (m, 4 H), 7.55 (m, 2 H), 7.89 (d, J=2.34 Hz, 1 H). MS (ESI) (M+H)$^+$: 557.

Example 18

N-[2-[(4-ethoxyphenyl)methyl]-1-[(tetrahydro-2H-pyran-4-yl)methyl]-1H-pyrrolo[2,3-b]pyridin-5-yl]-N-methyl-cyclobutanecarboxamide

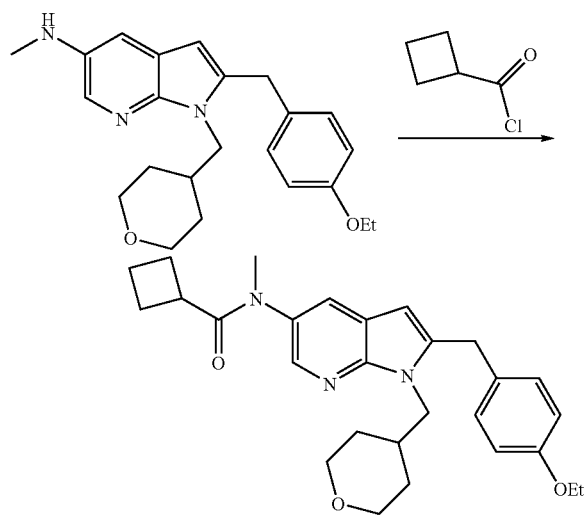

To a solution of 2-[(4-ethoxyphenyl)methyl]-N-methyl-1-[(tetrahydro-2H-pyran-4-yl)methyl]-1H-pyrrolo[2,3-b]pyridin-5-amine (54 mg, 0.14 mmol) in dichloromethane (5 mL) at 0° C. was added diisopropylethylamine (74 µL, 0.42 mmol) followed by cyclobutanecarbonyl chloride (33 µL, 0.28 mmol). The mixture was stirred overnight at room temperature. The reaction was then quenched by 2M Na$_2$CO$_3$ aqueous solution (10 mL). The phases were separated and the aqueous phase was back-extracted with additional dichloromethane (10 mL). The organic phases were combined, dried with MgSO$_4$, filtered and concentrated in vacuo. The residue was purified using HPLC (10 to 70% [0.1% TFA in AcCN solution] in 0.1% TFA aqueous solution) to provide 25 mg of the TFA salt of N-[2-[(4-ethoxyphenyl)methyl]-1-[(tetrahydro-2H-pyran-4-yl)methyl]-1H-pyrrolo[2,3-b]pyridin-5-yl]-N-methyl-cyclobutanecarboxamide. $^1$H NMR (400 MHz, METHANOL-D$_4$) δ 1.26 (m, 5 H), 1.61 (m, 4 H), 1.89 (m, 1 H), 2.13 (m, 2 H), 2.95 (m, 2 H), 3.11 (m, 2 H), 3.16 (s, 3 H), 3.75 (m, 2 H), 3.91 (q, J=6.96 Hz, 2 H), 3.98 (d, J=7.42 Hz, 2 H), 4.04 (m, 1 H), 4.06 (s, 2 H), 6.14 (s, 1 H), 6.77 (d, J=8.59 Hz, 2 H), 7.05 (d, J=8.59 Hz, 2 H), 7.62 (d, J=2.34 Hz, 1 H), 7.90 (d, J=2.34 Hz, 1 H). MS (ESI) (M+H)$^+$: 463.

Example 19

N-[2-[(4-ethoxyphenyl)methyl]-1-[(tetrahydro-2H-pyran-4-yl)methyl]-1H-pyrrolo[2,3-b]pyridin-5-yl]-2,5-difluoro-N-methyl-benzamide

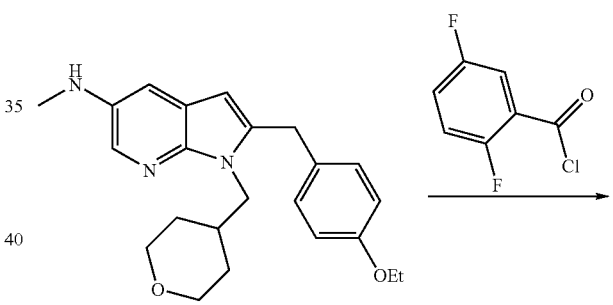

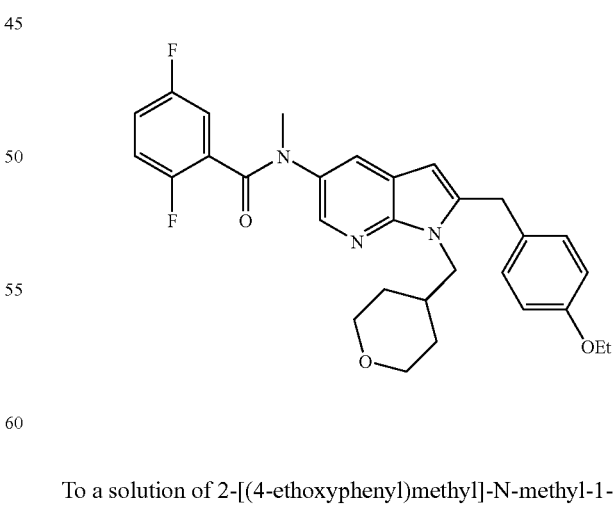

To a solution of 2-[(4-ethoxyphenyl)methyl]-N-methyl-1-[(tetrahydro-2H-pyran-4-yl)methyl]-1H-pyrrolo[2,3-b]pyridin-5-amine (52 mg, 0.14 mmol) in dichloromethane (5 mL) at 0° C. was added diisopropylethylamine (70 µL, 0.41 mmol) followed by 2,5-difluorophenylcarbonyl chloride (35 µL, 0.27 mmol). The mixture was stirred overnight at room temperature. The reaction was then quenched by 2 M Na₂CO₃ aqueous solution (10 mL). The phases were separated and the aqueous phase was back-extracted with additional dichloromethane (10 mL). The organic phases were combined, dried with MgSO₄, filtered and concentrated in vacuo. The residue was purified using HPLC (10 to 70% [0.1% TFA in AcCN solution] in 0.1% TFA aqueous solution) to provide 28 mg of the TFA salt of N-[2-[(4-ethoxyphenyl)methyl]-1-[(tetrahydro-2H-pyran-4-yl)methyl]-1H-pyrrolo[2,3-b]pyridin-5-yl]-2,5-difluoro-N-methyl-benzamide. ¹H NMR (400 MHz, METHANOL-D₄) δ 1.17 (m, 4 H), 1.26 (t, J=6.93 Hz, 3 H), 1.75 (m, 1 H), 3.05 (m, 2 H), 3.40 (s, 3 H), 3.69 (m, 2 H), 3.90 (m, 4 H), 3.99 (s, 2 H), 6.03 (s, 1 H), 6.75 (d, J=8.59 Hz, 2 H), 6.78 (m, 1 H), 6.83 (m, 1 H), 7.01 (d, J=8.59 Hz, 2 H), 7.04 (m, 1 H), 7.66 (d, J=2.15 Hz, 1 H), 7.85 (d, J=2.15 Hz, 1 H). MS (ESI) (M+H)⁺: 521.

Example 20

N-[2-[(4-ethoxyphenyl)methyl]-1-[(tetrahydro-2H-pyran-4-yl)methyl]-1H-pyrrolo[2,3-b]pyridin-5-yl]-N,2-dimethyl-propanamide

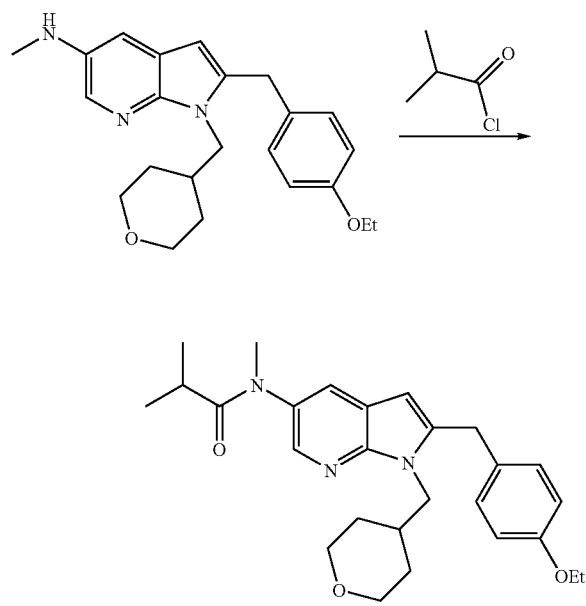

To a solution of 2-[(4-ethoxyphenyl)methyl]-N-methyl-1-[(tetrahydro-2H-pyran-4-yl)methyl]-1H-pyrrolo[2,3-b]pyridin-5-amine (50 mg, 0.13 mmol) in dichloromethane (5 ml) at 0° C. was added diisopropylethylamine (68 μL, 0.39 mmol) followed by isobutanoyl chloride (28 μL, 0.26 mmol). The mixture was stirred overnight at room temperature. The reaction was then quenched by 2M Na₂CO₃ aqueous solution (10 mL). The phases were separated and the aqueous phase was back-extracted with additional dichloromethane (10 mL). The organic phases were combined, dried with MgSO₄, filtered and concentrated in vacuo. The residue was purified using HPLC (10 to 70% [0.1% TFA in AcCN solution] in 0.1% TFA aqueous solution) to provide 28 mg of the TFA salt of N-[2-[(4-ethoxyphenyl)methyl]-1-[(tetrahydro-2H-pyran-4-yl)methyl]-1H-pyrrolo[2,3-b]pyridin-5-yl]-N,2-dimethyl-propanamide. ¹H NMR (400 MHz, METHANOL-D₄) δ 0.71 (d, J=6.64 Hz, 6 H) 1.19 (m, 2 H) 1.26 (m, 5 H) 1.90 (m, 1 H) 2.39 (m, 1 H) 3.11 (m, 2 H) 3.17 (s, 3 H) 3.76 (m, 2 H) 3.91 (m, 2 H) 3.98 (d, J=7.42 Hz, 2 H) 4.06 (s, 2 H) 6.16 (s, 1 H) 6.77 (d, J=7.82 Hz, 2 H) 7.05 (d, J=7.82 Hz, 2 H) 7.71 (s, 1 H) 7.98 (s, 1 H). MS (ESI) (M+H)⁺: 451.

Example 21

N-[2-[(4ethoxyphenyl)methyl]-1-[(tetrahydro-2H-pyran-4-yl)methyl]-1H-pyrrolo[2,3-b]pyridin-5-yl]-N,2,2-trimethyl-propanamide

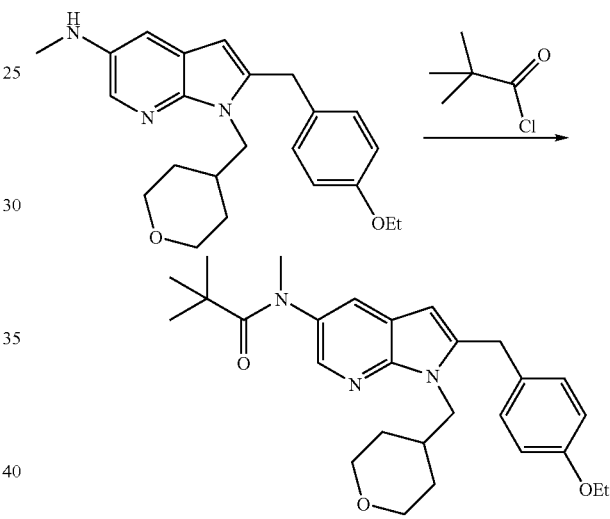

To a solution of 2-[(4-ethoxyphenyl)methyl]-N-methyl-1-[(tetrahydro-2H-pyran-4-yl)methyl]-1H-pyrrolo[2,3-b]pyridin-5-amine (53 mg, 0.14 mmol) in dichloromethane (5 ml) at 0° C. was added diisopropylethylamine (73 μL, 0.42 mmol) followed by 2,2-dimethylpropanoyl chloride (34 μL, 0.28 mmol). The mixture was stirred overnight at room temperature. The reaction was then quenched by 2M Na₂CO₃ aqueous solution (10 mL). The phases were separated and the aqueous phase was back-extracted with additional dichloromethane (10 mL). The organic phases were combined, dried with MgSO₄, filtered and concentrated in vacuo. The residue was purified using HPLC (10 to 70% [0.1% TFA in AcCN solution] in 0.1% TFA aqueous solution) to provide 20 mg of the TFA salt of N-[2-[(4-ethoxyphenyl)methyl]-1-[(tetrahydro-2H-pyran-4-yl)methyl]-1H-pyrrolo[2,3-b]pyridin-5-yl]-N,2,2-trimethyl-propanamide. ¹H NMR (400 MHz, METHANOL-D₄) δ 0.92 (s, 9 H) 1.25 (m, 7 H) 1.87 (m, 1 H) 3.10 (m, 2 H) 3.15 (s, 3 H) 3.75 (m, 2 H) 3.91 (q, J=6.96 Hz, 2 H) 3.99 (d, J=7.42 Hz, 2 H) 4.06 (s, 2 H) 6.14 (s, 1 H) 6.77 (d, J=8.79 Hz, 2 H) 7.06 (d, J=8.79 Hz, 2 H), 7.70 (d, J=2.34 Hz, 1 H) 7.97 (d, J=2.34 Hz, 1 H). MS (ESI) M+H)⁺: 465

Example 22

N-[2-[(4-ethoxyphenyl)methyl]-1[(tetrahydro-2H-pyran-4-yl)methyl]-1H-pyrrolo[2,3-b]pyridin-5-yl]-N-methyl-N'-(1-methylethyl)-urea

Example 23

N-[2-[(4-ethoxyphenyl)methyl]-1-[(tetrahydro-2H-pyran-4-yl)methyl]-1H-pyrrolo[2,3-b]pyridin-5-yl]-N,3-dimethyl-butanamide

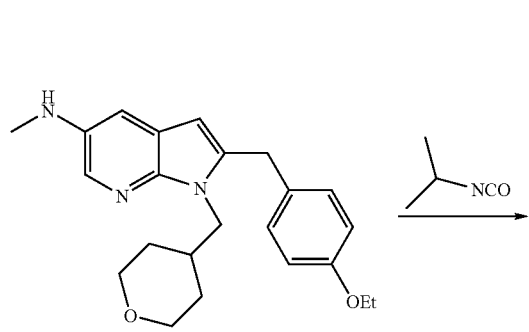

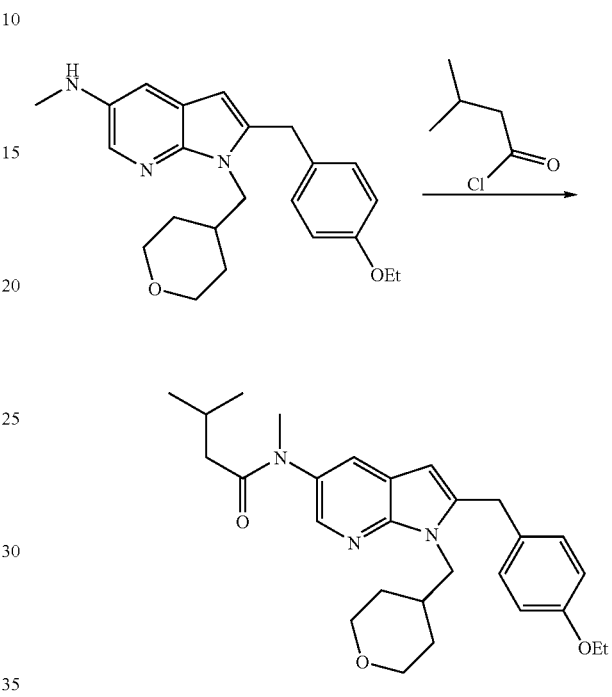

To a solution of 2-[(4-ethoxyphenyl)methyl]-N-methyl-1-[(tetrahydro-2H-pyran-4-yl)methyl]-1H-pyrrolo[2,3-b]pyridin-5-amine (710 mg, 1.87 mmol) in dichloromethane (5 mL) at 0° C. was added diisopropylethylamine (977 μL, 5.61 mmol) followed by isopropylisocyanate (367 μL, 3.74 mmol). The mixture was stirred overnight at room temperature. The reaction was then quenched by 2M $Na_2CO_3$ aqueous solution (100 mL). The phases were separated and the aqueous phase was back-extracted with additional dichlorometliane (100 mL). The organic phases were combined, dried with $MgSO_4$, filtered and concentrated in vacuo. The residue was purified using HPLC (10 to 70% [0.1% TFA in AcCN solution] in 0.1% TFA aqueous solution) to provide 461 mg of the TFA salt of N-[2-[(4-ethoxyphenyl)methyl]-1-[(tetrahydro-2H-pyran-4-yl)methyl]-1H-pyrrolo[2,3-b]pyridin-5-yl]-N-methyl-N'-(1-methylethyl)-urea. $^1$H NMR (400 MHz, CHLOROFORM-D) δ 1.02 (d, J=6.44 Hz, 6 H) 1.40 (t, J=6.93 Hz, 3 H) 1.45 (m, 4 H) 2.13 (m, 2 H) 3.26 (m, 2 H), 3.27 (s, 3 H) 3.94 (m, 2 H) 4.01 (q, J=6.93 Hz, 2 H) 4.05 (d, J=6.93 Hz, 2 H) 4.09 (s, 2 H) 6.14 (s, 1 H) 6.86 (m, 3 H) 7.10 (d, J=8.59 Hz, 2 H) 7.65 (d, J=2.34 Hz, 1 H) 8.13 (d, J=2.34 Hz, 1 H). MS (ESI) (M+H)$^+$: 466

To a solution of 2-[(4-ethoxyphenyl)methyl]-N-methyl-1-[(tetrahydro-2H-pyran-4-yl)methyl]-1H-pyrrolo[2,3-b]pyridin-5-amine (68 mg, 0.18 mmol) in dichloromethane (5 ml) at 0° C. was added diisopropylethylamine (94 μL, 0.54 mmol) followed by isovaleryl chloride (44 μL, 0.36 mmol). The mixture was stirred overnight at room temperature. The reaction was then quenched by 2M $Na_2CO_3$ aqueous solution (10 mL). The phases were separated and the aqueous phase was back-extracted with additional dichloromethane (10 mL). The organic phases were combined, dried with $MgSO_4$, filtered and concentrated in vacuo. The residue was purified using reversed phase silica gel flash chromatography (10 to 70% [0.1% TFA in AcCN solution] in 0.1% TFA aqueous solution) to provide 33 mg of the TFA salt of N-[2-[(4-ethoxyphenyl)methyl]-1-[(tetrahydro-2H-pyran-4-yl)methyl]-1H-pyrrolo[2,3-b]pyridin-5-yl]-N,3-dimethyl-butanamide.
$^1$H NMR (400 MHz, METHANOL-D$_4$) δ 0.71 (d, J=6.44 Hz, 6 H) 1.26 (t, J=6.93 Hz, 3 H) 1.33 (m, 4 H) 1.85 (m, 2 H) 1.89 (m, 2 H) 3.20 (s, 3 H) 3.74 (m, 2 H) 3.90 (q, J=6.93 Hz, 2 H) 3.98 (d, J=7.23 Hz, 2 H) 4.04 (m, 2 H) 4.06 (s, 2 H) 6.14 (s, 1 H) 6.76 (d, J=8.59 Hz, 2 H) 7.05 (d, J=8.59 Hz, 2 H) 7.66 (d, J=2.34 Hz, 1 H) 7.93 (d, J=2.34 Hz, 1 H). MS (ESI) (M+H)$^+$: 465.

Example 24

N-[1-(cyclobutylmethyl)-2-[(4-ethoxyphenyl)methyl]-1H-pyrrolo[2,3-b]pyridin-5-yl]-2,2-dimethyl-propanamide

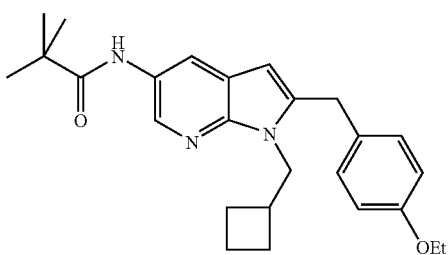

Step A: N-[6-[(cyclobutylmethyl)amino]-5-methyl-3-pyridinyl]-2,2-dimethyl-propanamide

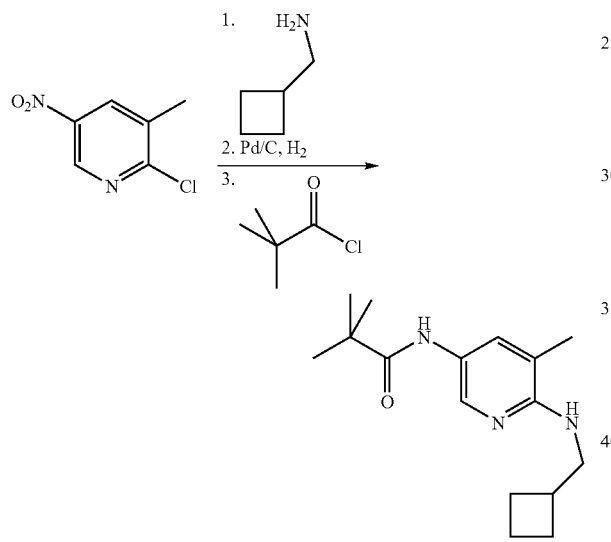

To a solution of 2-chloro-3-methyl-5-nitropyridine (5.1 g, 29.7 mmol) in ethanol (100 mL) at room temperature was added triethylamine (8.3 ml, 59.4 mmol) followed by cyclobutyl methylamine (2.8 g, 32.7 mmol). The reaction mixture was refluxed overnight. Subsequently, the mixture was cooled to room temperature and concentrated in vacuo.

The residue was taken up into ethyl acetate (75 ml) and palladium on carbon (120 mg, 10% grade, 0.1 mmol) was added. The suspension was placed in Parr apparatus and shaken for 72 hours under a hydrogen atmosphere (35 psi). The suspension was then brought to normal atmosphere and filtered on Diatomaceous earth. The filtrate was concentrated in vacuo.

This residue was taken up into dichloromethane (125 mL) at −78° C. to which was added diisopropyl ethylamine (6.2 mL, 35.6 mmol) followed by pivaloyl chloride (3.84 ml, 31.2 mmol). The mixture was stirred for two hours at 0° C. and then quenched with 2M NaOH aqueous solution (50 mL). The phases were separated and the aqueous phase was back-extracted with additional dichloromethane (125 mL). The organic phases were combined, dried with MgSO$_4$, filtered and concentrated in vacuo. The residue was purified using silica gel flash chromatography ([3% MeOH+0.5% NH$_4$OHaq] in CH$_2$Cl$_2$) to provide 6.75 g of the title compound N-[6-[(cyclobutylmethyl)amino]-5-methyl-3-pyridinyl]-2,2-dimethyl-propanamide. $^1$H NMR (400 MHz, CHLOROFORM-D) δ 1.29 (s, 9 H) 1.74 (m, 2 H) 1.91 (m, 2 H) 2.05 (s, 3 H) 2.09 (m, 2 H) 2.57 (m, 1 H) 3.45 (dd, J=7.42, 5.27 Hz, 2 H) 3.96 (s, 1 H) 7.09 (s, 1 H) 7.65 (d, J=2.54 Hz, 1 H) 7.85 (d, J=2.54 Hz, 1 H). MS (ESI) (M+H)$^+$: 276.

Step B. N-[1-(cyclobutylmethyl)-2-[(4-ethoxyphenyl)methyl]-1H-pyrrolo[2,3-b]pyridin-5-yl]-2,2-dimethyl-propanamide

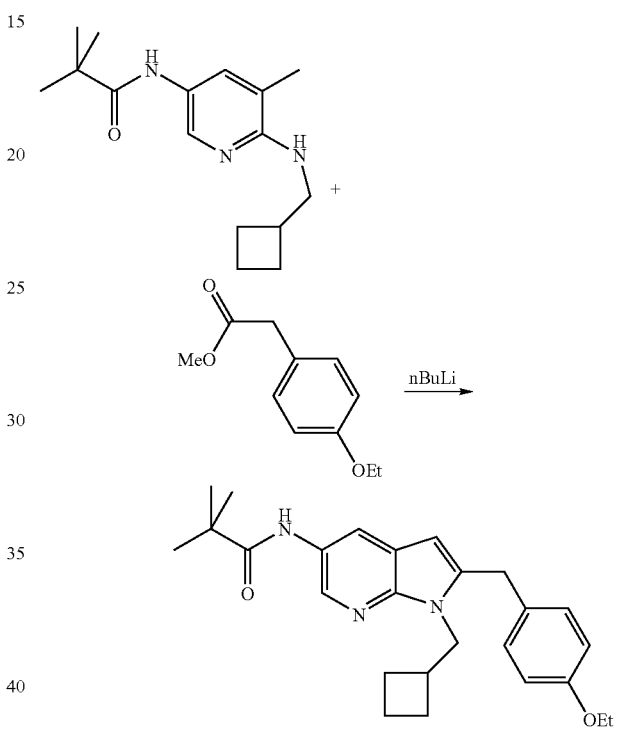

To a solution of N-[6-[(cyclobutylmethyl)amino]-5-methyl-3-pyridinyl]-2,2-dimethyl-propanamide (2.0 g, 7.26 mmol) in THF (70 ml) at −78° C. was added n-butyl lithium (12.7 mL of 2.0 M solution in cyclohexane, 25.4 mmol). The mixture was stirred for one hour at −20° C. and then cooled to −78° C. To this reaction mixture was cannulated to a solution of methyl 4-ethoxy-benzeneacetate (2.3 g, 11.6 mmol) in THF (50 mL) at −78° C. After stirring for 3 hours at room temperature, the mixture was quenched with NaHCO$_3$ saturated aqueous solution (200 ml) and diluted with EtOAc (100 mL). The phases were separated and the aqueous phase was back-extracted with additional EtOAc (100 mL). The organic phases were combined, dried with MgSO$_4$, filtered and concentrated in vacuo. The residue was purified using silica gel flash chromatography ([3% MeOH+0.5% NH$_4$OHaq] in CH$_2$Cl$_2$) to provide 650 mg of the title compound N-[1-(cyclobutylmethyl)-2-[(4-ethoxyphenyl)methyl]-1H-pyrrolo[2,3-b]pyridin-5-yl]-2,2-dimethyl-propanamide. $^1$H NMR (400 MHz, DMSO-D$_6$) δ 1.21 (s, 9 H) 1.29 (t, J=7.03 Hz, 3 H) 1.77 (m, 6 H) 2.69 (m, 1 H) 3.97 (q, J=7.03 Hz, 2 H) 4.06 (s, 2 H) 4.15 (d, J=7.23 Hz, 2 H) 5.99 (s, 1 H) 6.86 (d, J=8.59 Hz, 2 H) 7.14 (d, J=8.59 Hz, 2 H) 7.98 (d, J=2.34 Hz, 1 H) 8.21 (d, J=2.34 Hz, 1 H) 9.21 (s, 1 H). MS (ESI) (M+H)$^+$: 421.

Example 25

[1-(cyclobutylmethyl)-2-[(4-ethoxyphenyl)methyl]-1H-pyrrolo[2,3-b]pyridin-5-yl]-, methyl ester carbamic acid

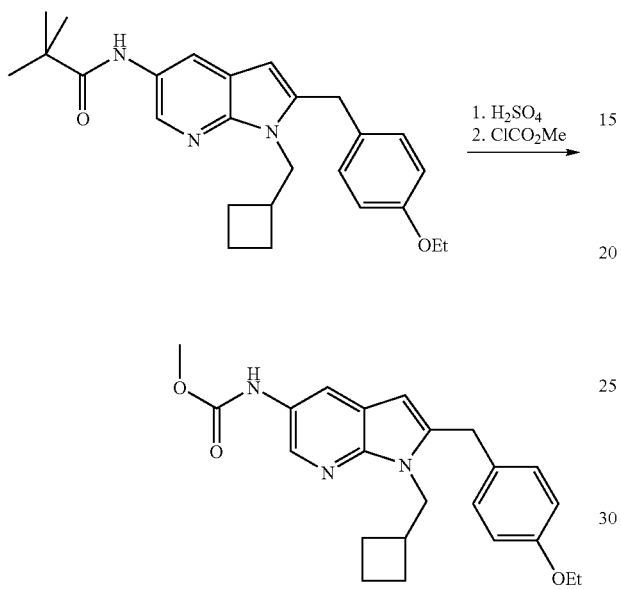

N-[1-(cyclobutylmethyl)-2-[(4-ethoxyphenyl)methyl]-1H-pyrrolo[2,3-b]pyridin-5-yl]-2,2-dimethyl-propanamide (872.4 mg, 2.1 mmol) was dissolved into a mixture of dioxane (25 mL) and 20% sulfuric acid aqueous solution (25 mL) at room temperature. The solution was brought to 120° C. After stirring for 6 hours, the mixture was cooled to room temperature and concentrated in vacuo. The residue was brought to pH 8 by addition of 2M NaOH aqueous solution (200 mL). The mixture was extracted twice with EtOAc (100 mL). The organic phases were combined, dried with MgSO$_4$, filtered and concentrated in vacuo.

The residue was taken up into dichloromethane (50 mL) and the mixture cooled to −30° C. To this solution was added diisopropyl ethylamine (905 µL, 5.2 mmol) followed by a solution of methylchloroformate (193 µL, 2.5 mmol) in dichloromethane (25 mL) at −78° C. The reaction was allowed to warm to 0° C. After stirring for 3 hours, the reaction was quenched with 2M Na$_2$CO$_3$ aqueous solution (50 mL). The phases were separated and the aqueous phase was back-extracted with additional dichloromethane (50 mL). The organic phases were combined, dried with MgSO$_4$, filtered and concentrated in vacuo. The residue was purified using silica gel flash chromatography ([3% MeOH+0.5% NH$_4$OHaq] in CH$_2$Cl$_2$) to provide 701 mg of the title compound [1-(cyclobutylmethyl)-2-[(4-ethoxyphenyl)methyl]-1H-pyrrolo[2,3-b]pyridin-5-yl]-methyl ester carbamic acid. 1H NMR (400 MHz, CHLOROFORM-D) δ 1.37 (t, J=6.93Hz, 3 H) 1.78 (m, 6 H) 2.66 (m, 1 H) 3.75 (s, 3 H) 3.89 (q, J=6.93 Hz, 2 H) 4.01 (s, 2 H) 4.11 (d, J=7.23 Hz, 2 H) 5.44 (s, 1 H) 6.08 (s, 1 H) 6.85 (m, 2 H) 7.09 (m, 2 H) 8.05 (d, J=2.35 Hz, 1 H) 8.13 (d, J=2.35 Hz, 1 H) MS (ESI) (M+H)$^+$: 395.

Example 26

N-[1-(cyclobutylmethyl)-2-[(4-ethoxyphenyl)methyl]-1H-pyrrolo[2,3-b]pyridin-5-yl]-2,6-difluoro-N-methyl-benzenesulfonamide

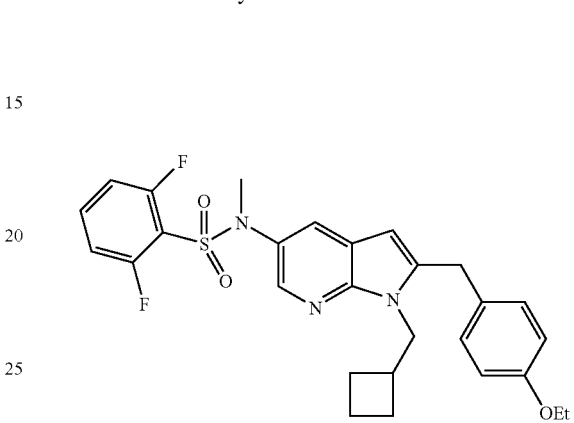

Step A. 1-(cyclobutylmethyl)-2-[(4-ethoxyphenyl)methyl]-1H-pyrrolo[2,3-b]pyridin-5-amine To a solution of [1-(cyclobutylmethyl)-2-[(4-ethoxyphenyl)methyl]-1H-pyrrolo[2,3-b]pyridin-5-yl]-methyl ester carbamic acid (701 mg, 1.78 mmol) in THF (25 mL) at 0° C. was added lithium aluminum hydride (300 mg, 7.90 mmol). The mixture was stirred for 48 hours at room temperature. The reaction was then cooled to 0° C. and quenched by dropwise addition of water (300 µL), followed by 4M NaOH aqueous solution (300 µL) and water (900 µL). After stirring at room temperature for 30 minutes, the suspension was filtered over Diatomaceous earth and concentrated in vacuo to give 517 mgs of colorless oil. MS (ESI) (M+H)$^+$: 350.

Step B. N-[1-(cyclobutylmethyl)-2-[(4-ethoxyphenyl)methyl]-1H-pyrrolo[2,3-b]pyridin-5-yl]-2,6-difluoro-N-methyl-benzenesulfonamide

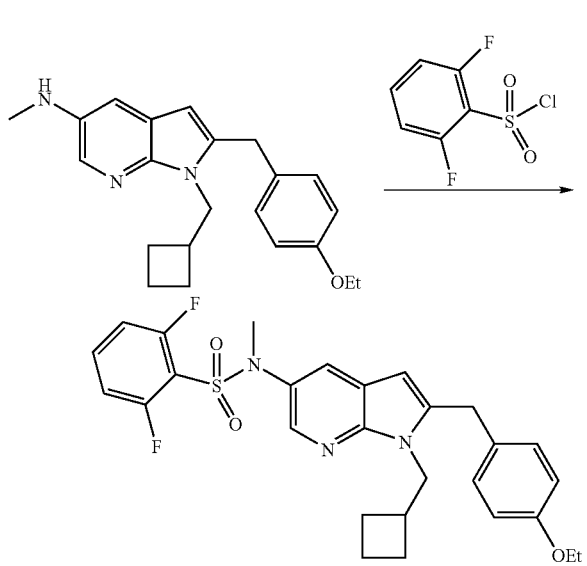

To a solution 1-(cyclobutylmethyl)-2-[(4-ethoxyphenyl)methyl]-1H-pyrrolo[2,3-b]pyridin-5-amine (50 mg, 0.14 mmol) in dichloromethane (5 mL) at 0° C. was added diisopropylethylamine (75 µL, 0.43 mmol) followed by 2,6-difluorobenzenesulfonyl chloride (61 mg, 0.29 mmol). The mixture was stirred overnight at room temperature. The reaction was then quenched by 2M $Na_2CO_3$ aqueous solution (10 mL). The phases were separated and the aqueous phase was back-extracted with additional dichloromethane (10 mL). The organic phases were combined, dried with $MgSO_4$, filtered and concentrated in vacuo. The residue was purified using HPLC (10 to 70% [0.1% TFA in AcCN solution] in 0.1% TFA aqueous solution) to provide 24 mg of the TFA salt of N-[1-(cyclobutylmethyl)-2-[(4-ethoxyphenyl)methyl]-1H-pyrrolo[2,3-b]pyridin-5-yl]-2,6-difluoro-N-methyl-benzenesulfonamide. $^1$H NMR (400 MHz, METHANOL-$D_4$) δ 1.35 (t, J=7.03 Hz, 3 H) 1.82 (m, 6 H) 2.71 (m, 1 H) 3.40 (s, 3 H) 3.99 (q, J=7.03 Hz, 2 H) 4.08 (s, 2 H) 4.17 (d, J=7.23 Hz, 2 H) 6.05 (s, 1 H) 6.84 (m, 2 H) 7.09 (m, 4 H) 7.64 (m, 2 H) 7.97 (d, J=2.34 Hz, 1 H). MS (ESI) (M+H)$^+$: 527.

Example 27

N-[1-(cyclobutylmethyl)-2-[(4-ethoxyphenyl)methyl]-1H-pyrrolo[2,3-b]pyridin-5-yl]-N-methyl-2-pyridinecarboxamide

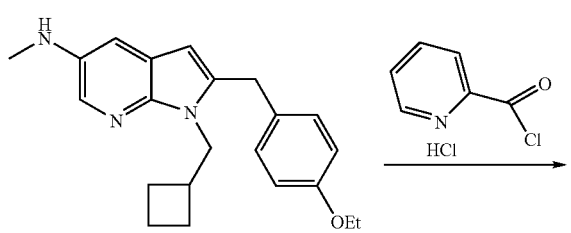

-continued

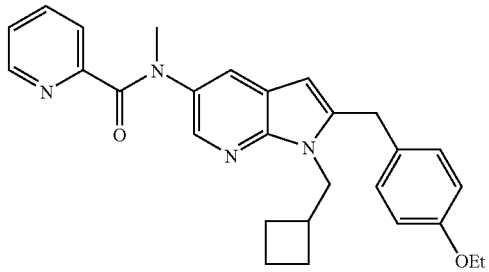

To a solution of 1-(cyclobutylmethyl)-2-[(4-ethoxyphenyl)methyl]-1H-pyrrolo[2,3-b]pyridin-5-amine (42 mg, 0.12 mmol) in dichloromethane (5 ml) at 0° C. was added diisopropylethylamine (84 µL, 0.48 mmol) followed by 2-pyridinecarbonyl chloride, hydrochloride salt (43 mg, 0.24 mmol). The mixture was stirred overnight at room temperature. The reaction was then quenched by 2M $Na_2CO_3$ aqueous solution (10 mL). The phases were separated and the aqueous phase was back-extracted with additional dichloromethane (10 mL). The organic phases were combined, dried with $MgSO_4$, filtered and concentrated in vacuo. The residue was purified using HPLC (10 to 70% [0.1% TFA in AcCN solution] in 0.1% TFA aqueous solution) to provide 21 mg of the TFA salt of N-[1-(cyclobutylmethyl)-2-[(4-ethoxyphenyl)methyl]-1H-pyrrolo[2,3-b]pyridin-5-yl]-N-methyl-2-pyridinecarboxamide. $^1$H NMR (400 MHz, METHANOL-$D_4$) δ 1.32 (t, J=6.93 Hz, 3 H) 1.68 (m, 6 H) 2.53 (m, 1 H) 3.42 (s, 3 H) 3.89 (m, 2 H) 3.94 (s, 2 H) 4.04 (q, J=6.93 Hz, 2 H) 5.90 (s, 1 H) 6.74 (m, 2 H) 6.95 (m, 2 H) 7.09 (m, 1 H) 7.32 (m, 1 H) 7.55 (m, 1 H) 7.59 (m, 1 H) 7.76 (m, 1 H) 8.16 (s, 1 H). MS (ESI) (M+H)$^+$: 456.

Example 28

N-[1-(cyclobutylmethyl)-2-[(4-ethoxyphenyl)methyl]-1H-pyrrolo[2,3-b]pyridin-5-yl]-N,3-dimethylbutanamide

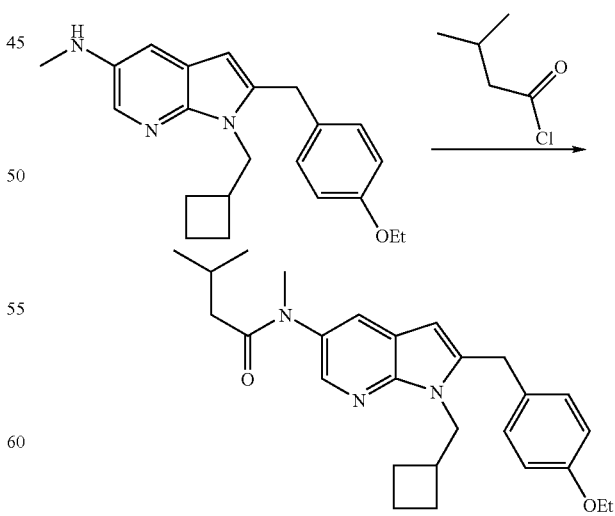

To a solution of 1-(cyclobutylmethyl)-2-[(4-ethoxyphenyl)methyl]-1H-pyrrolo[2,3-b]pyridin-5-amine (71 mg, 0.20 mmol) in dichloromethane (5 mL) at 0° C. was added diisopropylethylamine (107 µL, 0.61 mmol) followed by isovaleryl chloride (50 µL, 0.41 mmol). The mixture was stirred overnight at room temperature. The reaction was then quenched by 2 M Na$_2$CO$_3$ aqueous solution (10 mL). The phases were separated and the aqueous phase was back-extracted with additional dichloromethane (10 mL). The organic phases were combined, dried with MgSO$_4$, filtered and concentrated in vacuo. The residue was purified using reversed phase silica gel flash chromatography (10 to 70% [0.1% TFA in AcCN solution] in 0.1% TFA aqueous solution) to provide 20 mg of the TFA salt of N-[1-(cyclobutylmethyl)-2-[(4-ethoxyphenyl)methyl]-1H-pyrrolo[2,3-b]pyridin-5-yl]-N,3-dimethyl-butanamide. $^1$H NMR (400 MHz, METHANOL-D$_4$) δ 0.69 (d, J=6.64 Hz, 6 H) 1.25 (t, J=6.93 Hz, 3 H) 1.72 (m, 6 H) 1.80 (m, 1 H) 1.91 (d, J=6.64 Hz, 2 H) 2.64 (d, J=7.23 Hz, 1 H) 3.17 (s, 3 H) 3.89 (q, J=6.93 Hz, 2 H) 4.02 (s, 2 H) 4.11 (d, J=7.23 Hz, 2 H) 6.05 (s, 1 H) 6.75 (m, 2 H) 7.02 (d, J=8.59 Hz, 2 H) 7.62 (d, J=2.15 Hz, 1 H) 7.91 (d, J=2.15 Hz, 1 H). MS (ESI) (M+H)$^+$: 435.

Example 29

N-[1-(cyclobutylmethyl)-2-[(4-ethoxyphenyl)methyl]-1H-pyrrolo[2,3-b]pyridin-5-yl]-N-methyl-N'-(1-methylethyl)-urea

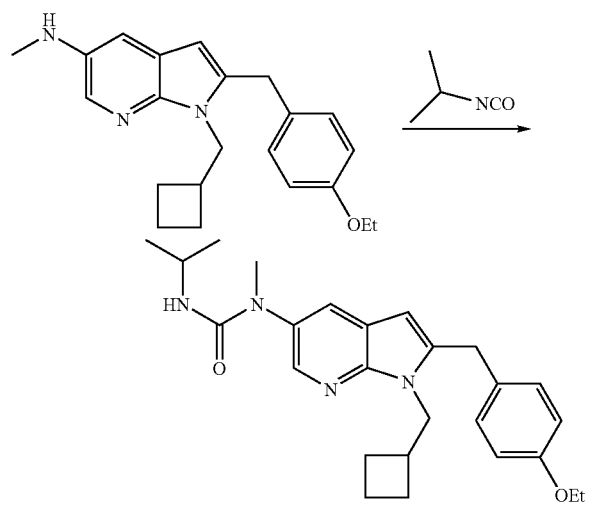

To a solution of 1-(cyclobutylmethyl)-2-[(4-ethoxyphenyl)methyl]-1H-pyrrolo[2,3-b]pyridin-5-amine (71 mg, 0.20 mmol) in dichloromethane (5 ml) at 0° C. was added diisopropylethylamine (107 µL, 0.61 mmol) followed by isopropylisocyanate (41 µL, 0.41 mmol). The mixture was stirred overnight at room temperature. The reaction was then quenched by 2 M Na$_2$CO$_3$ aqueous solution (10 mL). The phases were separated and the aqueous phase was back-extracted with additional dichloromethane (10 mL). The organic phases were combined, dried with MgSO$_4$, filtered and concentrated in vacuo. The residue was purified using reversed phase silica gel flash chromatography (10 to 70% [0.1% TFA in AcCN solution] in 0.1% TFA aqueous solution) to provide 18 mg of the TFA salt of N-[1-(cyclobutylmethyl)-2-[(4-ethoxyphenyl)methyl]-1H-pyrrolo[2,3-b]pyridin-5-yl]-N-methyl-N'-(1-methylethyl)-urea. $^1$H NMR (400 MHz, METHANOL-D$_4$) δ 0.93 (d, J=6.64 Hz, 6 H) 1.25 (t, J=6.96 Hz, 3 H) 1.72 (m, 4 H) 1.80 (m, 2 H) 2.66 (m, 1 H) 3.13 (s, 3 H) 3.77 (m, 1 H) 3.89 (q, J=6.96 Hz, 2 H) 4.02 (s, 2 H) 4.09 (d, J=7.23 Hz, 2 H) 6.07 (s, 1 H) 6.74 (d, J=8.79 Hz, 2 H) 7.01 (d, J=8.79 Hz, 2 H) 7.66 (d, J=2.34 Hz, 1 H) 7.93 (d, J=2.34 Hz, 1 H). MS (ESI) (M+H)$^+$: 436.

Example 30

N-[1-(cyclobutylmethyl)-2-[(4-ethoxyphenyl)methyl]-1H-pyrrolo[2,3-b]pyridin-5-yl]-N,1-dimethyl-1H-imidazole-5-sulfonamide

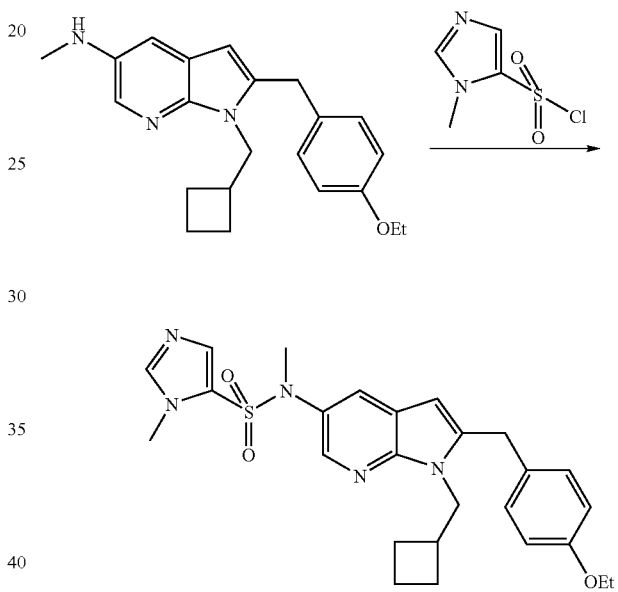

To a solution of 1-(cyclobutylmethyl)-2-[(4-ethoxyphenyl)methyl]-1H-pyrrolo[2,3-b]pyridin-5-amine (43 mg, 0.12 mmol) in dichloromethane (5 ml) at 0° C. was added diisopropylethylamine (84 µL, 0.48 mmol) followed by the hydrochloride salt of 1-methyl 1H-imidazole-5-sulfonyl chloride (52 mg, 0.24 mmol). The mixture was stirred overnight at room temperature. The reaction was then quenched by 2M Na$_2$CO$_3$ aqueous solution (10 mL). The phases were separated and the aqueous phase was back-extracted with additional dichloromethane (10 mL). The organic phases were combined, dried with MgSO$_4$, filtered and concentrated in vacuo. The residue was purified using HPLC (10 to 70% [0.1% TFA in AcCN solution] in 0.1% TFA aqueous solution) to provide 14 mg of the TFA salt of N-[1-(cyclobutylmethyl)-2-[(4-ethoxyphenyl)methyl]-1H-pyrrolo[2,3-b]pyridin-5-yl]-N,1-dimethyl-1H-imidazole-5-sulfonamide. $^1$H NMR (400 MHz, METHANOL-D$_4$) δ 1.25 (m, 3 H) 1.75 (m, 6 H) 2.62 (s, 1 H) 3.25 (s, 3 H) 3.63 (m, 3 H) 3.90 (q, J=7.03 Hz, 2 H) 3.99 (s, 2 H) 4.06 (d, J=7.23 Hz, 2 H) 5.98 (s, 1 H) 6.75 (m, 2 H) 7.00 (d, J=8.59 Hz, 2 H) 7.38 (d, J=1.17 Hz, 1 H) 7.49 (d, J=2.34 Hz, 1 H) 7.68 (s, 1 H) 7.84 (d, J=2.34 Hz, 1 H). MS (ESI) (M+H)$^+$: 495

Example 31

N-[1-(cyclobutylmethyl)-2-[(4-ethoxyphenyl)methyl]-1H-pyrrolo[2,3-b]pyridin-5-yl]-N,5-dimethyl-3-isoxazolecarboxamide

Example 32

N-[1-(cyclobutylmethyl)-2-[(4-ethoxyphenyl)methyl]-1H-pyrrolo[2,3-b]pyridin-5-yl]-4-(dimethylamino)-N-methyl-benzamide

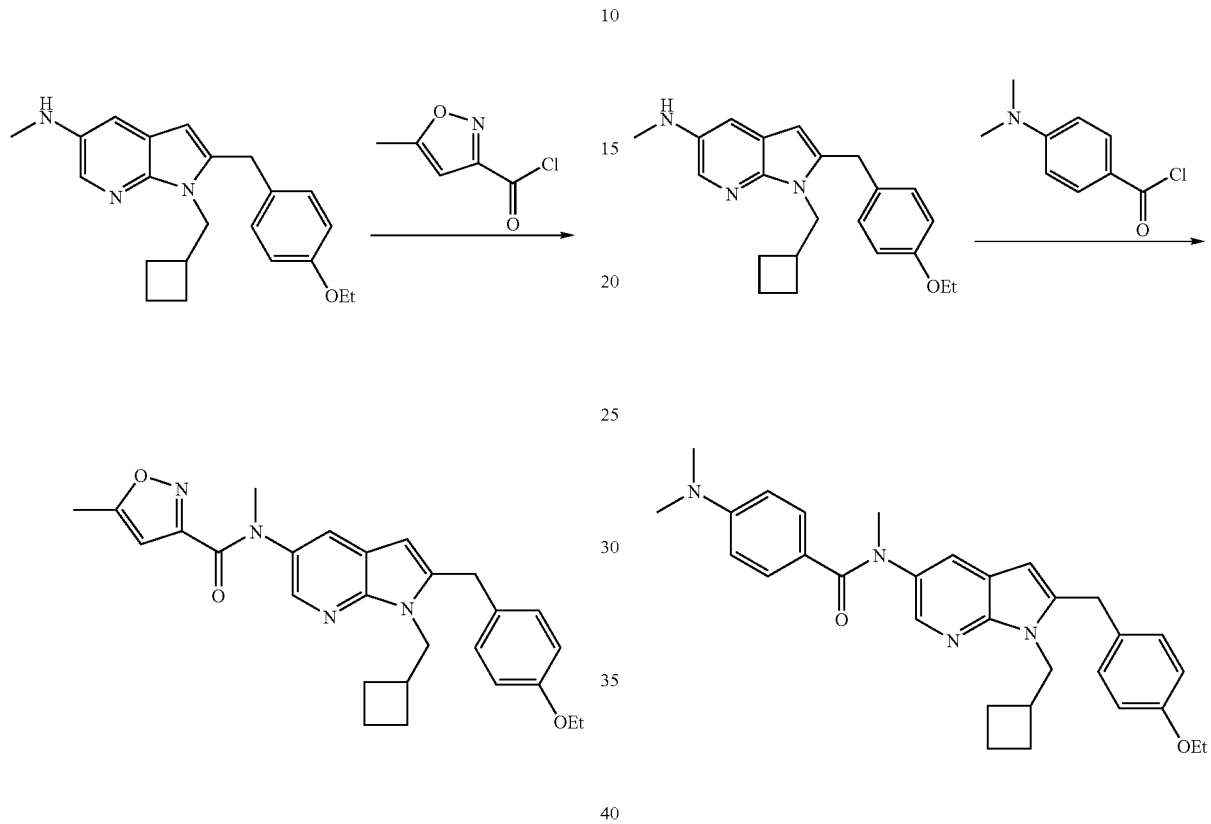

To a solution of 1-(cyclobutylmethyl)-2-[(4-ethoxyphenyl)methyl]-1H-pyrrolo[2,3-b]pyridin-5-amine (57 mg, 0.16 mmol) in dichloromethane (5 ml) at 0° C. was added diisopropylethylamine (84 μL, 0.48 mmol) followed by 5-methyl-3-isoxazolecarbonyl chloride (48 mg, 0.33 mmol). The mixture was stirred overnight at room temperature. The reaction was then quenched by 2M $Na_2CO_3$ aqueous solution (10 mL). The phases were separated and the aqueous phase was back-extracted with additional dichloromethane (10 mL). The organic phases were combined, dried with $MgSO_4$, filtered and concentrated in vacuo. The residue was purified using HPLC (10 to 70% [0.1% TFA in AcCN solution] in 0.1% TFA aqueous solution) to provide 25 mg of the TFA salt of 3-isoxazolecarboxamide N-[1-(cyclobutylmethyl)-2-[(4-ethoxyphenyl)methyl]-1H-pyrrolo[2,3-b]pyridin-5-yl]-N,5-dimethyl-3-isoxazolecarboxamide. $^1$H NMR (400 MHz, METHANOL-$D_4$) δ 1.26 (m, 3 H) 1.71 (m, 6 H) 2.12 (s, 3 H) 2.61 (m, 1 H) 3.37 (s, 3 H) 3.90 (q, J=6.96 Hz, 2 H) 3.99 (s, 2 H) 4.08 (d, J=7.23 Hz, 2 H) 5.84 (s, 1 H) 5.99 (s, 1 H) 6.75 (m, 2 H) 7.01 (d, J=8.59 Hz, 2 H) 7.63 (d, J=2.34 Hz, 1 H) 7.86 (d, J=2.34 Hz, 1 H). MS (ESI) (M+H)$^+$: 460

To a solution of 1-(cyclobutylmethyl)-2-[(4-ethoxyphenyl)methyl]-1-H-pyrrolo[2,3-b]pyridin-5-amine (52 mg, 0.15 mmol) in dichloromethane (5 ml) at 0° C. was added diisopropylethylamine (78 μL, 0.45 mmol) followed by 4-(dimethylamino)-benzoyl chloride (55 mg, 0.30 mmol). The mixture was stirred overnight at room temperature. The reaction was then quenched by 2M $Na_2CO_3$ aqueous solution (10 mL). The phases were separated and the aqueous phase was back-extracted with additional dichloromethane (10 mL). The organic phases were combined, dried with $MgSO_4$, filtered and concentrated in vacuo. The residue was purified using HPLC (10 to 70% [0.1% TFA in AcCN solution] in 0.1% TFA aqueous solution) to provide 19 mg of the TFA salt of N-[1-(cyclobutylmethyl)-2-[(4-ethoxyphenyl)methyl]-1H-pyrrolo[2,3-b]pyridin-5-yl]-4-(dimethylamino)-N-methyl-benzamide. $^1$H NMR (400 MHz, METHANOL-$D_4$) δ 1.25 (t, J=6.93 Hz, 3 H) 1.68 (m, 6 H) 2.58 (m, 1 H) 2.76 (s, 6 H) 3.36 (s, 3 H) 3.89 (q, J=6.93 Hz, 2 H) 3.96 (s, 2 H) 4.03 (d, J=7.22 Hz, 2 H) 5.95 (s, 1 H) 6.40 (d, J=8.79 Hz, 2 H) 6.74 (d, J=8.59 Hz, 2 H) 7.00 (d, J=8.59 Hz, 2 H) 7.06 (d, J=8.79 Hz, 2 H) 7.62 (d, J=2.34 Hz, 1 H) 7.71 (d, J=2.34 Hz, 1 H). MS (ESI) (M+H)$^+$: 498

Example 33

4-[[[1-(cyclobutylmethyl)-2-[(4-ethoxyphenyl)methyl]-1H-pyrrolo[2,3-b]pyridin-5-yl]methylamino]sulfonyl]-benzoic acid

Example 34

N-[1-(cyclobutylmethyl)-2-[(4-ethoxyphenyl)methyl]-1H-pyrrolo[2,3-b]pyridin-5-yl]-N-methyl-2-nitro-benzenesulfonamide

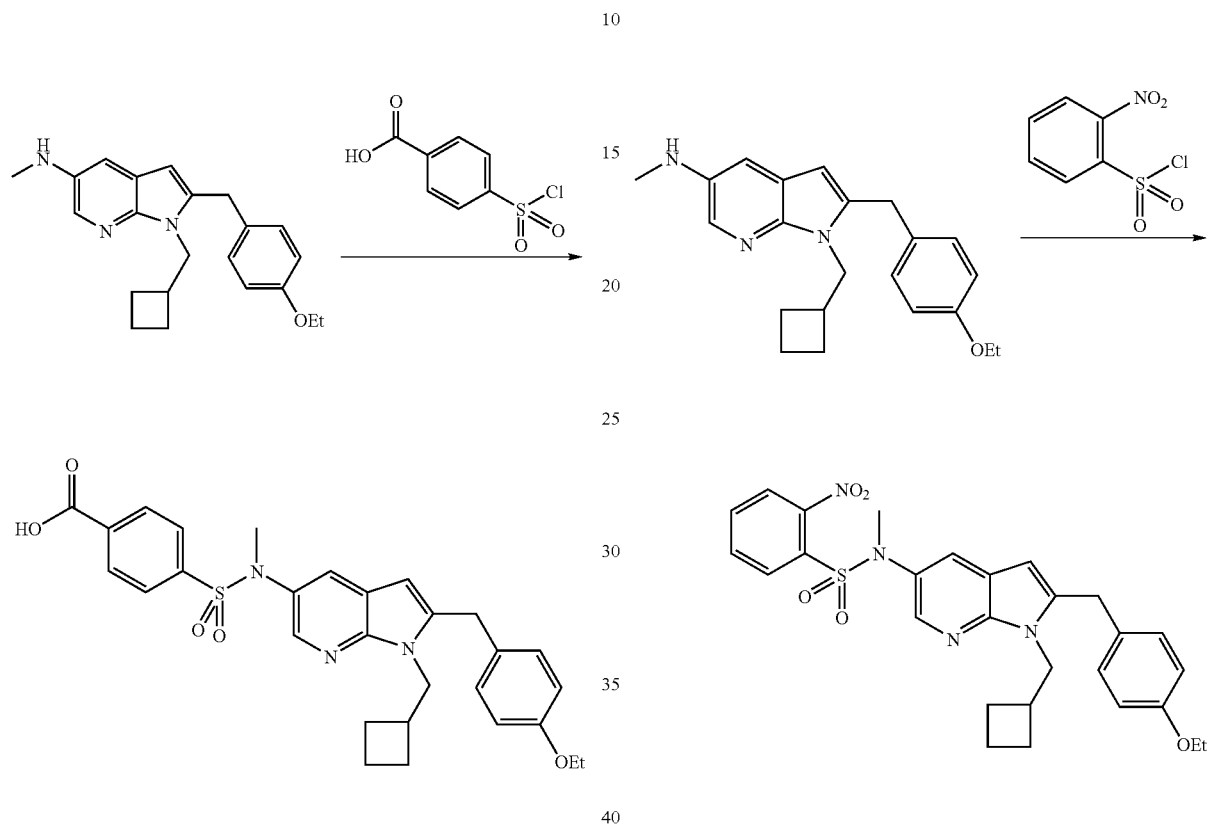

To a solution of 1-(cyclobutylmethyl)-2-[(4-ethoxyphenyl)methyl]-1H-pyrrolo[2,3-b]pyridin-5-amine (60 mg, 0.17 mmol) in dichloromethane (5 mL) at 0° C. was added diisopropylethylamine (118 μL, 0.68 mmol) followed by 4-(chlorosulfonyl)-benzoic acid (76 mg, 0.34 mmol). The mixture was stirred overnight at room temperature. The reaction was then quenched by 2M Na$_2$CO$_3$ aqueous solution (10 mL). The phases were separated and the aqueous phase was back-extracted with additional dichloromethane (10 mL). The organic phases were combined, dried with MgSO$_4$, filtered and concentrated in vacuo. The residue was purified using HPLC (10 to 70% [0.1% TFA in AcCN solution] in 0.1% TFA aqueous solution) to provide 12 mg of the TFA salt of 4-[[[1-(cyclobutylmethyl)-2-[(4-ethoxyphenyl)methyl]-1H-pyrrolo[2,3-b]pyridin-5-yl]methylamino]sulfonyl]-benzoic acid. $^1$H NMR (400 MHz, METHANOL-D$_4$) δ 1.25 (t, J=7.03 Hz, 3 H) 1.72 (m, 6 H) 2.60 (m, 1 H) 3.41 (s, 3 H) 3.90 (q, J=7.03 Hz, 2 H) 4.03 (s, 2 H) 4.10 (m, 2 H) 5.98 (s, 1 H) 6.77 (d, J=8.59 Hz, 2 H) 7.03 (d, J=8.59 Hz, 2 H) 7.28 (m, 2 H) 7.54 (m, 2 H) 8.08 (s, 1 H) 8.19 (s, 1 H). MS (ESI) (M+H)$^+$: 535

To a solution of 1-(cyclobutylmethyl)-2-[(4-ethoxyphenyl)methyl]-1H-pyrrolo[2,3-b]pyridin-5-amine (52 mg, 0.15 mmol) in dichloromethane (5 mL) at 0° C. was added diisopropylethylamine (78 μL, 0.45 mmol) followed by 2-nitrobenzenesulfonyl chloride (65 mg, 0.30 mmol). The mixture was stirred overnight at room temperature. The reaction was then quenched by 2M Na$_2$CO$_3$ aqueous solution (10 mL). The phases were separated and the aqueous phase was back-extracted with additional dichloromethane (10 mL). The organic phases were combined, dried with MgSO$_4$, filtered and concentrated in vacuo. The residue was purified using HPLC (10 to 70% [0.1% TFA in AcCN solution] in 0.1% TFA aqueous solution) to provide 21 mg of the TFA salt of N-[1-(cyclobutylmethyl)-2-[(4-ethoxyphenyl)methyl]-1H-pyrrolo[2,3-b]pyridin-5-yl]-N-methyl-2-nitro-benzenesulfonamide. $^1$H NMR (400 MHz, METHANOL-D$_4$) δ 1.25 (t, J=6.93 Hz, 3 H) 1.72 (m, 6 H) 2.61 (m, 1 H) 3.28 (s, 3 H) 3.88 (q, J=6.93 Hz, 2 H) 3.98 (s, 2 H) 4,07 (d, J=7.23 Hz, 2 H) 5.97 (s, 1 H) 6.73 (d, J=8.79 Hz, 2 H) 6.99 (d, J=8.79 Hz, 2 H) 7.47 (m, 2 H) 7.53 (d, J=2.34 Hz, 1 H) 7.65 (m, 2 H) 7.82 (d, J=2.34 Hz, 1 H). MS (ESI) (M+H)$^+$: 536

What is claimed is:

1. A compound of formula I or a pharmaceutically acceptable salt thereof:

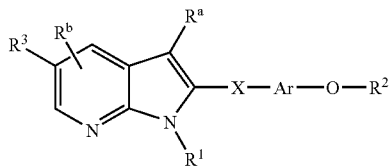

wherein

R¹ is optionally substituted $C_{1-10}$ hydrocarbyl; optionally substituted $C_{1-10}$acyl; optionally substituted $C_{4-8}$heteroaryl-C(=O)—; $R^4R^5N$—$C_{1-6}$alkyl; $R^4R^5NC$(=O)—$C_{1-6}$alkyl; $R^4O$—$C_{1-6}$alkyl; $R^4OC$(=O)—$C_{1-6}$alkyl; $R^4C$(=O)—$C_{1-6}$alkyl; $R^4C$(=O)$NR^4$—$C_{1-6}$alkyl; $R^4R^5NSO_2$—$C_{1-6}$alkyl; $R^4CSO_2N(R^5)$—$C_{1-6}$alkyl; $R^4R^5NC$(=O)$N(R^6)$—$C_{1-6}$alkyl; $R^4R^5NSO_2N$($R^6$)—$C_{1-6}$alkyl; optionally substituted aryl-$C_{1-6}$alkyl; optionally substituted aryl-C(=O)—$C_{1-6}$alkyl; optionally substituted heterocyclyl-$C_{1-6}$alkyl; optionally substituted heterocyclyl-C(=O)—$C_{1-6}$alkyl; and $C_{1-10}$hydrocarbylamino;

wherein $R^4$, $R^5$ and $R^6$ are independently selected from —H, $C_{1-6}$alkyl, $C_{2-6}$alkenyl, $C_{2-6}$alkynyl, or a divalent $C_{1-6}$group that together with another divalent $C_{1-6}$group forms a portion of a ring;

X is selected from the group consisting of —NR⁶—, —CH₂—CH₂—, —CH=CH—, —O—, —C(R⁸)(R⁹)—, and —S(O)$_q$—, wherein a is 0, 1 or 2, wherein $R^8$ and $R^9$ are independently $C_{1-6}$alkyl, $C_{2-6}$alkenyl, $C_{2-6}$alkynyl, $C_{1-6}$alkoxy, —OH, or —H; at most one of $R^8$ and $R^9$ is —OH;

Ar is a $C_{4-12}$ divalent aromatic group;

R² is optionally substituted $C_{1-6}$hydrocarbyl, optionally substituted $C_{6-10}$aryl, or optionally substituted $C_{3-6}$heteroaryl;

R³ is selected from:

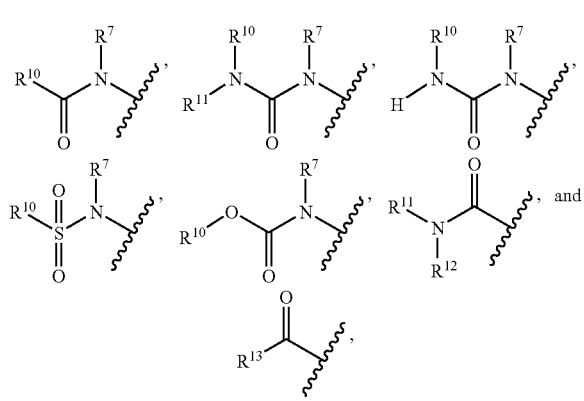

wherein

R⁷ is selected from —H, optionally substituted $C_{1-6}$alkyl, optionally substituted $C_{2-6}$alkenyl, optionally substituted $C_{2-6}$alkynyl, optionally substituted $C_{3-6}$cycloalkyl, optionally substituted $C_{6-10}$ aryl, or optionally substituted $C_{3-6}$heteroaryl;

R¹⁰, R¹¹, R¹² and R¹³ are independently selected from optionally substituted $C_{1-6}$alkyl, optionally substituted $C_{2-6}$alkenyl, optionally substituted $C_{2-6}$alkynyl, optionally substituted $C_{3-6}$cycloalkyl, optionally substituted $C_{6-10}$ aryl, or optionally substituted $C_{3-6}$heteroaryl; and $R^a$ and $R^b$ are —R, —NO₂, —OR, —Cl, —Br, —I, —F, —OF₃, —C(=O)R, —C(=O)OH, —NH₂, —SH, —NHR, —NR², —SR, —SO₃H, —SO₂R, —S(=O)R, —CN, —OH, —C(=O)OR, or —NRC(=O)R, wherein R is independently —H or $C_{1-6}$ hydrocarbyl.

2. A compound as claimed in claim 1, wherein $R^a$ and $R^b$ are hydrogen.

3. A compound as claimed claim 1,
wherein R¹ is selected from $C_{1-8}$alkyl; $C_{2-8}$alkenyl; $C_{2-8}$ alkynyl; optionally substituted aryl-$C_{1-6}$alkyl; $R^4R^5NC_{1-6}$alkyl; $R^4OC_{1-6}$alkyl; $C_{3-6}$cycloalkyl-$C_{1-6}$alkyl; optionally substituted $C_{3-6}$heterocycloalkyl-$C_{1-6}$alkyl; $C_{1-6}$alkyl $C_{6-8}$aryl; $C_{1-6}$alkyl-C(=O)—; $C_{6-8}$aryl-C(=O)—; $C_{3-8}$heteroaryl-C(=O)—; or optionally substituted $C_{3-6}$heteroaryl-$C_{1-6}$alkyl;

wherein R² is selected from $C_{1-6}$alkyl, $C_{1-6}$alkyl substituted by at least one fluorine, $C_{2-6}$alkenyl, $C_{2-6}$alkenyl substituted by at least one fluorine, $C_{2-6}$alkynyl, $C_{2-6}$alkynyl substituted by at least one fluorine, optionally substituted $C_{3-6}$cycloalkyl, optionally substituted $C_{6-10}$aryl, and optionally substituted $C_{3-6}$heteroaryl;

R⁴, R⁵ and R⁶ are independently selected from the group consisting of —H, $C_{1-6}$alkyl, $C_{2-6}$alkenyl, $C_{2-6}$alkynyl, and a divalent $C_{1-6}$group that together with another divalent $C_{1-6}$group forms a portion of a ring;

R³ is selected from;

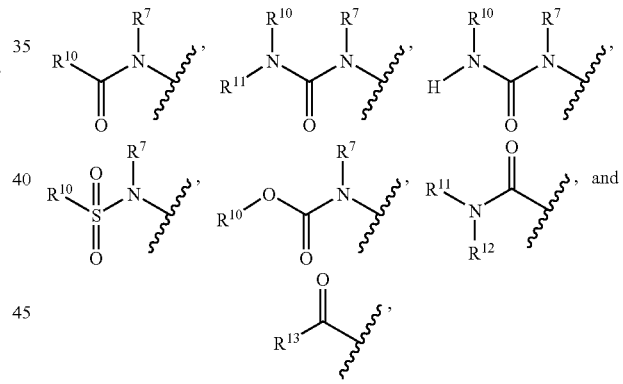

wherein

R⁷ is selected from —H, optionally substituted $C_{1-6}$alkyl, optionally substituted $C_{2-6}$alkenyl, optionally substituted $C_{2-6}$alkynyl, optionally substituted $C_{3-6}$cycloalkyl, optionally substituted $C_{6-10}$aryl, or optionally substituted $C_{3-6}$heteroaryl;

R¹⁰, R¹¹, R¹² and R¹³ are independently selected from optionally substituted $C_{1-6}$alkyl, optionally substituted $C_{2-6}$alkenyl, optionally substituted $C_{2-6}$alkynyl, optionally substituted $C_{3-6}$cycloalkyl, optionally substituted $C_{6-10}$ aryl, or optionally substituted $C_{3-6}$heteroaryl; and $R^a$ and $R^b$ are hydrogen.

4. A compound as claimed in claim 3, wherein
R¹ is selected from $C_{1-6}$alkyl; $C_{2-6}$alkenyl; $C_{2-6}$ alkynyl; optionally substituted $C_{3-6}$cycloalkylmethyl; optionally substituted $C_{3-6}$heterocycloalkylmethyl;

X is —CH₂—;

Ar is phenylene or pyridylene;

R² is selected from —CH₃, —CH₂CH₃, —CH(CH₃)₂, —CH₂CF₃, CF₃, cyclopropyl, cyclobutyl, cyclopentyl, cyclohexyl, pyridyl and phenyl; and R³ is selected from

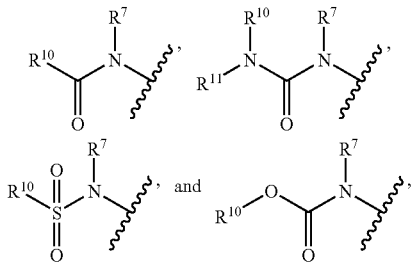

wherein, R⁷ is selected from —H and methyl; R¹⁰ and R¹¹ are independently selected from optionally substituted $C_{1-6}$alkyl, optionally substituted $C_{2-6}$alkenyl, optionally substituted $C_{2-6}$alkynyl, optionally substituted $C_{3-6}$cycloalkyl, optionally substituted $C_{6-10}$ aryl, or optionally substituted $C_{3-6}$heteroaryl.

5. A compound as claimed in claim 3, wherein

R¹ is selected from $C_{1-6}$alkyl; $C_{2-6}$alkenyl; $C_{2-6}$ alkynyl; optionally substituted $C_{3-6}$cycloalkylmethyl; optionally substituted $C_{3-6}$heterocycloalkylmethyl;

X is —CH₂—;

Ar is selected from the group consisting of an optionally substituted para-arylene; an optionally substituted a six-membered para-heteroarylene;

R² is selected from —CH₃, —CH₂CH₃, —CH(CH₃)₂, —CH₂CF₃, CF₃, cyclopropyl, cyclobutyl, cyclopentyl, cyclohexyl, pyridyl and phenyl; and R³ is selected from;

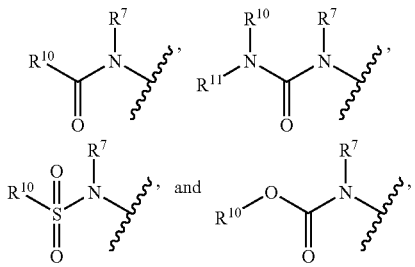

wherein, R⁷ is selected from —H and methyl; R¹⁰ and R¹¹ are selected from optionally substituted $C_{1-6}$alkyl, optionally substituted $C_{2-6}$alkenyl, optionally substituted $C_{2-6}$alkynyl, optionally substituted $C_{3-6}$cycloalkyl, optionally substituted $C_{6-10}$ aryl, or optionally substituted $C_{3-6}$heteroaryl.

6. A compound as claimed in claim 3, wherein

R¹ is selected from optionally substituted $C_{3-6}$cycloalkylmethyl; and optionally substituted $C_{3-6}$heterocycloalkylmethyl;

X is —CH₂—;

Ar is para-phenylene or para-pyridylene;

R² is methyl, or ethyl; and

R³ is selected from

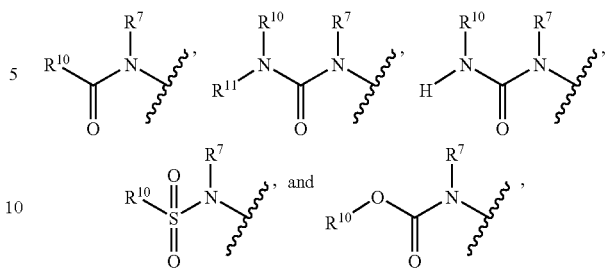

wherein, R⁷ is selected from —H and methyl; R¹⁰ and R¹¹ are selected from $C_{1-6}$alkyl, $C_{3-6}$cycloalkyl, phenyl optionally substituted with halogen, nitro, $C_{1-3}$alkyl, —COOR¹⁴, —OH, cyano, trifluormethyl, $C_{1-3}$alkyloxy; $C_{3-6}$heteroaryl optionally substituted with halogen, nitro, $C_{1-3}$alkyl, —COOR¹⁴, —OH, cyano, trifluormethyl, $C_{1-3}$alkyloxy, wherein R¹⁴ is a $C_{1-3}$alkyl.

7. A compound selected from:
1) N-[1-(cyclohexylmethyl)-2-[(4-ethoxyphenyl)methyl]-1H-pyrrolo[2,3-b]pyridin-5-yl]-2,2-dimethyl-propanamide;
2) N-[1-(cyclohexylmethyl)-2-[(3-methoxyphenyl)methyl]-1H-pyrrolo[2,3-b]pyridin-5-yl]-2,2-dimethyl-propanamide;
3) N-[1-(cyclohexylmethyl)-2-[(4-ethoxyphenyl)methyl]-1H-pyrrolo[2,3-b]pyridin-5-yl]-N-methyl-N-(1-methylethyl)-urea;
4) N-[1-(cyclohexylmethyl)-2-[(4-ethoxyphenyl)methyl]-1H-pyrrolo[2,3-b]pyridin-5-yl]-N,3-dimethyl-butanamide;
5) N-[1-(cyclohexylmethyl)-2-[(4-ethoxyphenyl)methyl]-1H-pyrrolo[2,3-b]pyridin-5-yl]-N,2-dimethyl-propanamide;
6) N-[1-(cyclohexylmethyl)-2-[(4-ethoxyphenyl)methyl]-1H-pyrrolo[2,3-b]pyridin-5-yl]-N-methyl-cyclopropanecarboxamide;
7) N-[1-(cyclohexylmethyl)-2-[(4-ethoxyphenyl)methyl]-1H-pyrrolo[2,3-b]pyridin-5-yl]-N,2,2-trimethyl-propanamide;
8) N-[1-(cyclohexylmethyl)-2-[(4-ethoxyphenyl)methyl]-1H-pyrrolo[2,3-b]pyridin-5-yl]-N',N'-diethyl-N-methyl-urea;
9) N-[1-(cyclohexylmethyl)-2-[(4-ethoxyphenyl)methyl]-1H-pyrrolo[2,3-b]pyridin-5-yl]-N,5-dimethyl-3-isoxazolecarboxamide;
10) N-[1-(cyclohexylmethyl)-2-[(4-ethoxyphenyl)methyl]-1H-pyrrolo[2,3-b]pyridin-5-yl]-2-fluoro-N-methyl-benzamide;
11) N-[1-(cyclohexylmethyl)-2-[(5-ethoxy-2-pyridinyl)methyl]-1H-pyrrolo[2,3-b]pyridin-5-yl]-2,2-dimethyl-propanamide;
12) [1-(cyclohexylmethyl)-2-[(5-ethoxy-2-pyridinyl)methyl]-1H-pyrrolo[2,3-b]pyridin-5-yl]-, 1-methylethyl ester carbamic acid;
13) N-[1-(cyclohexylmethyl)-2-[(5-ethoxy-2-pyridinyl)methyl]-1H-pyrrolo[2,3-b]pyridin-5-yl]-N,2,2-trimethyl-propanamide;
14) N-[1-(cyclohexylmethyl)-2-[(5-ethoxy-2-pyridinyl)methyl]-1H-pyrrolo[2,3-b]pyridin-5-yl]-N,3-dimethyl-butanamide;
15) N-[1-(cyclohexylmethyl)-2-[(5-ethoxy-2-pyridinyl)methyl]-1H-pyrrolo[2,3-b]pyridin-5-yl]-N-methyl-N'-(1-methylethyl)-urea;

16) N-[2-[(4-ethoxyphenyl)methyl]-1-[(tetrahydro-2H-pyran-4-yl)methyl]-1H-pyrrolo[2,3-b]pyridin-5-yl]-2,2-dimethyl-propanamide;

17) N-[2-[(4-ethoxyphenyl)methyl]-1-[(tetrahydro-2H-pyran-4-yl)methyl]-1H-pyrrolo[2,3-b]pyridin-5-yl]-2,6-difluoro-N-methyl-benzenesulfonamide;

18) N-[2-[(4-ethoxyphenyl)methyl]-1-[(tetrahydro-2H-pyran-4-yl)methyl]-1H-pyrrolo[2,3-b]pyridin-5-yl]-N-methyl-cyclobutanecarboxamide;

19) N-[2-[(4-ethoxyphenyl)methyl]-1-[(tetrahydro-2H-pyran-4-yl)methyl]-1H-pyrrolo[2,3-b]pyridin-5-yl]-2,5-difluoro-N-methyl-benzamide;

20) N-[2-[(4-ethoxyphenyl)methyl]-1-[(tetrahydro-2H-pyran-4-yl)methyl]-1H-pyrrolo[2,3-b]pyridin-5-yl]-N,2-dimethyl-propanamide;

21) N-[2-[(4-ethoxyphenyl)methyl]-1-[(tetrahydro-2H-pyran-4-yl)methyl]-1H-pyrrolo[2,3-b]pyridin-5-yl]-N,2,2-trimethyl-propanamide;

22) N-[2-[(4-ethoxyphenyl)methyl]-1-[(tetrahydro-2H-pyran-4-yl)methyl]-1H-pyrrolo[2,3-b]pyridin-5-yl]-N-methyl-N'-(1-methylethyl)-urea;

23) N-[2-[(4-ethoxyphenyl)methyl]-1-[(tetrahydro-2H-pyran-4-yl)methyl]-1H-pyrrolo[2,3-b]pyridin-5-yl]-N,3-dimethyl-butanamide;

24) N-[1-(cyclobutylmethyl)-2-[(4-ethoxyphenyl)methyl]-1H-pyrrolo[2,3-b]pyridin-5-yl]-2,2-dimethyl-propanamide;

25) [1-(cyclobutylmethyl)-2-[(4-ethoxyphenyl)methyl]-1H-pyrrolo[2,3-b]pyridin-5-yl]-, methyl ester carbamic acid;

26) N-[1-(cyclobutylmethyl)-2-[(4-ethoxyphenyl)methyl]-1H-pyrrolo[2,3-b]pyridin-5-yl]-2,6-difluoro-N-methyl-benzenesulfonamide;

27) N-[1-(cyclobutylmethyl)-2-[(4-ethoxyphenyl)methyl]-1H-pyrrolo[2,3-b]pyridin-5-yl]-N-methyl-2-pyridinecarboxamide;

28) N-[1-(cyclobutylmethyl)-2-[(4-ethoxyphenyl)methyl]-1H-pyrrolo[2,3-b]pyridin-5-yl]-N,3-dimethyl-butanamide;

29) N-[1-(cyclobutylmethyl)-2-[(4-ethoxyphenyl)methyl]-1H-pyrrolo[2,3-b]pyridin-5-yl]-N-methyl-N'-(1-methylethyl)-urea;

30) N-[1-(cyclobutylmethyl)-2-[(4-ethoxyphenyl)methyl]-1H-pyrrolo[2,3-b]pyridin-5-yl]-N,1-dimethyl-1H-imidazole-5-sulfonamide;

31) N-[1-(cyclobutylmethyl)-2-[(4-ethoxyphenyl)methyl]-1H-pyrrolo[2,3-b]pyridin-5-yl]-4-(dimethylamino)-N-methyl-benzamide;

32) N-[1-(cyclobutylmethyl)-2-[(4-ethoxyphenyl)methyl]-1H-pyrrolo[2,3-b]pyridin-5-yl]-N,5-dimethyl-3-isoxazolecarboxamide;

33) 4-[[[1-(cyclobutylmethyl)-2-[(4-ethoxyphenyl)methyl]-1H-pyrrolo[2,3-b]pyridin-5-yl]methylamino]sulfonyl]-benzoic acid;

34) N-[1-(cyclobutylmethyl)-2-[(4-ethoxyphenyl)methyl]-1H-pyrrolo[2,3-b]pyridin-5-yl]-N-methyl-2-nitro-benzenesulfonamide; and pharmaceutically acceptable salts thereof.

8. A pharmaceutical composition comprising a compound according to claim 1 and a pharmaceutically acceptable carrier.

9. A method for preparing a compound of formula II,

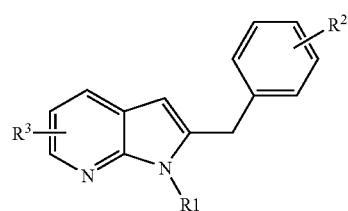

comprising the steps of
a) reacting a compound of formula III,

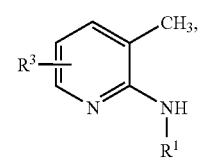

with a base having a pKa more than 20;
b) reacting a product formed in step a) with a compound of formula IV,

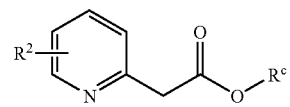

to form the compound of formula II,
wherein
$R^1$ is optionally substituted $C_{1-10}$ hydrocarbyl; optionally substituted $C_{1-10}$acyl; optionally substituted $C_{4-8}$heteroaryl-C(=O)—; $R^4R^5N$—$C_{1-6}$alkyl; $R^4R^5NC(=O)$—$C_{1-6}$alkyl; $R^4O$—$C_{1-6}$ alkyl; $R^4OC(=O)$—$C_{1-6}$alkyl; $R^4C(=O)$—$C_{1-6}$alkyl; $R^4C(=O)NR^4$—$C_{1-6}$alkyl; $R^4R^5NSO_2$—$C_{1-6}$alkyl; $R^4CSO_2N(R^5)$—$C_{1-6}$alkyl; $R^4R^5NC(=O)N(R^6)$—$C_{1-6}$alkyl; $R^4R^5NSO_2N(R^6)$—$C_{1-6}$alkyl; optionally substituted aryl-$C_{1-6}$alkyl; optionally substituted aryl-C(=O)—$C_{1-6}$alkyl; optionally substituted heterocyclyl-$C_{1-6}$alkyl; optionally substituted heterocyclyl-C(=O)—$C_{1-6}$alkyl; and $C_{1-10}$hydrocarbylamino;

wherein $R^4$, $R^5$ and $R^6$ are independently selected from —H, $C_{1-6}$alkyl, $C_{2-6}$alkenyl, $C_{2-6}$alkynyl, or a divalent $C_{1-6}$group that together with another divalent $C_{1-6}$group forms a portion of a ring;

$R^2$ is optionally substituted $C_{1-6}$hydrocarbyl, optionally substituted $C_{6-10}$aryl, or optionally substituted $C_{3-6}$heteroaryl;

$R^3$ is selected from;

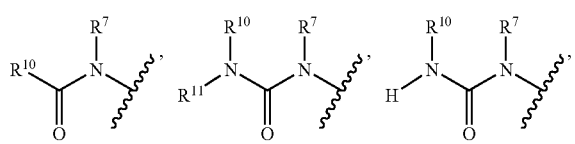

-continued

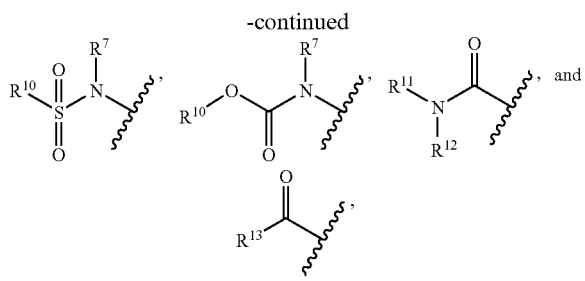

wherein
R[7] is selected from —H, optionally substituted C$_{1-6}$alkyl, optionally substituted C$_{2-6}$alkenyl, optionally substituted C$_{2-6}$alkynyl, optionally substituted C$_{3-6}$cycloalkyl, optionally substituted C$_{6-10}$aryl, or optionally substituted C$_{3-6}$heteroaryl;

R[10], R[11], R[12] and R[13] are independently selected from optionally substituted C$_{1-6}$alkyl, optionally substituted C$_{2-6}$alkenyl, optionally substituted C$_{2-6}$alkynyl, optionally substituted C$_{3-6}$cycloalkyl, optionally substituted C$_{6-10}$ aryl, or optionally substituted C$_{3-6}$heteroaryl; and R$^c$ is C$_{1-4}$alkyl.

10. A process as claimed in claim 9, wherein
the base is t-butyl lithium;
R[1] is selected from C$_{1-6}$alkyl; C$_{2-6}$alkenyl; C$_{2-6}$ alkynyl; optionally substituted C$_{3-6}$cycloalkylmethyl; optionally substituted C$_{3-6}$heterocycloalkylmethyl;
R[2] is selected from —CH$_3$, —CH$_2$CH$_3$, —CH(CH$_3$)$_2$, —CH$_2$CF$_3$, CF$_3$, cyclopropyl, cyclobutyl, cyclopentyl, cyclohexyl, pyridyl and phenyl; and
R[3] is selected from;

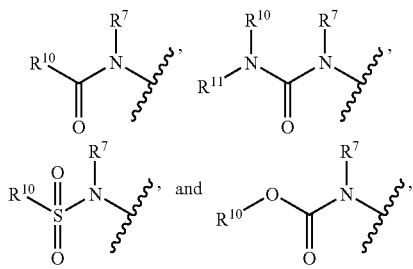

wherein, R[7] is selected from —H and methyl; R[10] and R[11] are independently selected from optionally substituted C$_{1-6}$alkyl, optionally substituted C$_{2-6}$alkenyl, optionally substituted C$_{2-6}$alkynyl, optionally substituted C$_{3-6}$cycloalkyl, optionally substituted C$_{6-10}$ aryl, or optionally substituted C$_{3-6}$heteroaryl.

11. A process for preparing a compound of formula V,

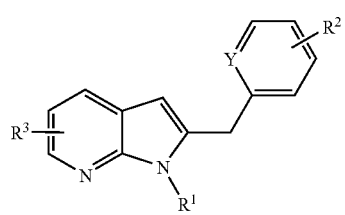

comprising the step of reacting a compound of formula VI,

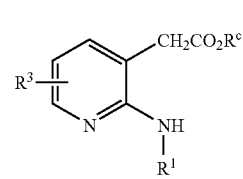

with a compound of formula VII,

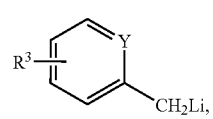

to form the compound of formula V,
wherein
R[1] is optionally substituted C$_{1-10}$ hydrocarbyl; optionally substituted C$_{1-10}$acyl; optionally substituted C$_{4-8}$heteroaryl-C(=O)—; R[4]R[5]N—C$_{1-6}$alkyl; R[4]R[5]NC(=O)—C$_{1-6}$alkyl; R[4]O—C$_{1-6}$ alkyl; R[4]OC(=O)—C$_{1-6}$alkyl; R[4]C(=O)—C$_{1-6}$alkyl; R[4]C(=O)NR[4]—C$_{1-6}$alkyl; R[4]R[5]NSO$_2$—C$_{1-6}$alkyl; R[4]CSO$_2$N(R[5])—C$_{1-6}$alkyl; R[4]R[5]NC(=O)N(R[6])—C$_{1-6}$alkyl; R[4]R[5]NSO$_2$N(R[6])—C$_{1-6}$alkyl; optionally substituted aryl-C$_{1-6}$alkyl; optionally substituted aryl-C(=O)—C$_{1-6}$alkyl; optionally substituted heterocyclyl-C$_{1-6}$ alkyl; optionally substituted heterocyclyl-C(=O)—C$_{1-6}$alkyl; and C$_{1-10}$hydrocarbylamino;
wherein R[4], R[5] and R[6] are independently selected from —H, C$_{1-6}$alkyl, C$_{2-6}$alkenyl, C$_{2-6}$alkynyl, or a divalent C$_{1-6}$group that together with another divalent C$_{1-6}$group forms a portion of a ring;
R[2] is optionally substituted C$_{1-6}$hydrocarbyl, optionally substituted C$_{6-10}$aryl, or optionally substituted C$_{3-6}$heteroaryl;
R[3] is selected from;

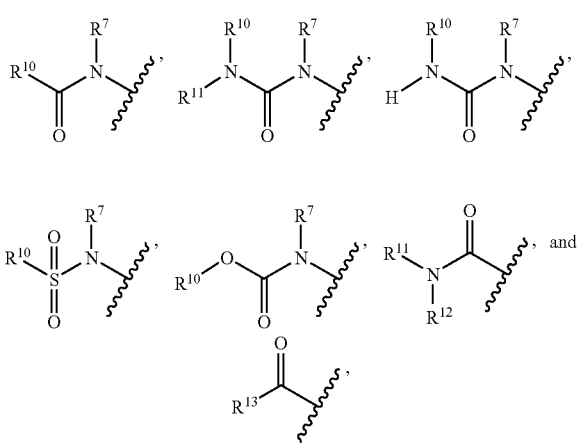

wherein
R[7] is selected from —H, optionally substituted C$_{1-6}$alkyl, optionally substituted C$_{2-6}$alkenyl, optionally substituted C$_{2-6}$alkynyl, optionally substituted $C_{3-6}$cycloalkyl, optionally substituted $C_{6-10}$ aryl, or optionally substituted $C_{3-6}$heteroaryl;

$R^{10}$, $R^{11}$, $R^{12}$ and $R^{13}$ are independently selected from optionally substituted $C_{1-6}$alkyl, optionally substituted $C_{2-6}$alkenyl, optionally substituted $C_{2-6}$alkynyl, optionally substituted $C_{3-6}$cycloalkyl, optionally substituted $C_{6-10}$ aryl, or optionally substituted $C_{3-6}$heteroaryl;

Y is CH or N; and $R^c$ is $C_{1-4}$alkyl.

12. A process as claimed in claim 11, wherein $R^1$ is selected from $C_{1-6}$alkyl; $C_{2-6}$alkenyl; $C_{2-6}$ alkynyl; optionally substituted $C_{3-6}$cycloalkylmethyl; optionally substituted $C_{3-6}$heterocycloalkylmethyl;

$R^2$ is selected from —$CH_3$, —$CH_2CH_3$, —$CH(CH_3)_2$, —$CH_2CF_3$, $CF_3$, cyclopropyl, cyclobutyl, cyclopentyl, cyclohexyl, pyridyl and phenyl; and $R^3$ is selected from;

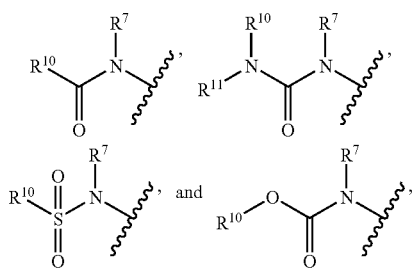

wherein, $R^7$ is selected from —H and methyl; $R^{10}$ and $R^{11}$ are independently selected from optionally substituted $C_{1-6}$alkyl, optionally substituted $C_{2-6}$alkenyl, optionally substituted $C_{2-6}$alkynyl, optionally substituted $C_{3-6}$cycloalkyl, optionally substituted $C_{6-10}$ aryl, or optionally substituted $C_{3-6}$heteroaryl.

\* \* \* \* \*